(12) United States Patent
Brunecky et al.

(10) Patent No.: US 10,538,753 B2
(45) Date of Patent: Jan. 21, 2020

(54) MULTIFUNCTIONAL MICROBIAL CELLULASES

(71) Applicant: Alliance for Sustainable Energy, LLC, Golden, CO (US)

(72) Inventors: Roman Brunecky, Arvada, CO (US); Venkataramanan Subramanian, Arvada, CO (US); Stephen Robert Decker, Berthoud, CO (US); Michael E. Himmel, Littleton, CO (US)

(73) Assignee: Alliance for Sustainably Enegry, LLC, Golden, CO (US)

( * ) Notice: Subject to any disclaimer, the term of this patent is extended or adjusted under 35 U.S.C. 154(b) by 0 days.

(21) Appl. No.: 15/913,620

(22) Filed: Mar. 6, 2018

(65) Prior Publication Data

US 2018/0273926 A1    Sep. 27, 2018

Related U.S. Application Data

(60) Provisional application No. 62/467,674, filed on Mar. 6, 2017.

(51) Int. Cl.
| | | |
|---|---|---|
| *C12N 9/42* | (2006.01) | |
| *C12N 15/63* | (2006.01) | |
| *C12N 1/15* | (2006.01) | |
| *C12N 15/62* | (2006.01) | |
| *C12P 19/02* | (2006.01) | |
| *C12P 19/14* | (2006.01) | |

(52) U.S. Cl.
CPC ............ *C12N 9/2437* (2013.01); *C12P 19/02* (2013.01); *C12P 19/14* (2013.01); *C12Y 302/01004* (2013.01); *Y02E 50/343* (2013.01)

(58) Field of Classification Search
CPC . C12N 9/42; C12N 15/63; C12N 1/15; C12N 15/62
See application file for complete search history.

(56) References Cited

U.S. PATENT DOCUMENTS

2012/0135499 A1* 5/2012 Bower ................. C12N 15/625
435/209

OTHER PUBLICATIONS

Tsai et al., "Surface Display of a Functional Minicellulosome by Intracellular Complementation Using a Synthetic Yeast Consortium and Its Application to Cellulose Hydrolysis and Ethanol Production", Applied and Environmental Microbiology, Nov. 2010, pp. 7514-7520.

* cited by examiner

*Primary Examiner* — Maryam Monshipouri
(74) *Attorney, Agent, or Firm* — Sam J. Barkley

(57) ABSTRACT

Disclosed herein are methods of making multifunctional microbial cellulases. The engineered multifunctional microbial cellulases disclosed herein exhibit improved activity over native cellulases.

11 Claims, 38 Drawing Sheets
Specification includes a Sequence Listing.

ATGTCTGCCTTGAACTCTTTCAATATGTACAAGAGCGCCCTCATCTTGGGCTCCTTGCTGGCAACAGCTG
GTGCTCAGCAAATTGGTACTTATACCGCTGAAACCCATCCCTCTCTGAGCTGGTCTACTTGCAAATCGGG
TGGTAGCTGCACCACAAACTCCGGTGCCATTACGTTAGATGCCAACTGGCGTTGGGTCCATGGTGTCAAT
ACCAGCACCAACTGCTACACTGGCAACACTTGGAATAGCGCCATCTGCGACACTGATGCATCCTGTGCCC
AGGACTGTGCTCTCGATGGTGCTGACTACTCTGGCACGTACGGTATCACTACCTCCGGCAACTCATTGCG
CCTGAACTTCGTTACCGGTTCCAACGTCGGATCTCGTACTTACCTGATGGCCGATAACACCCACTACCAA
ATCTTCGATCTGTTGAACCAGGAGTTCACCTTCACCGTCGATGTCTCCCACCTCCCTTGCGGTTTGAACG
GTGCCCTCTACTTCGTGACCATGGATGCCGACGGTGGCGTCTCCAAGTACCCCAACAACAAGGCCGGTGC
TCAGTACGGTGTTGGATACTGTGACTCTCAATGCCCTCGTGACTTGAAGTTCATCGCTGGTCAGGCCAAC
GTTGAGGGCTGGACGCCCTCCGCCAACAACGCCAACACTGGAATTGGCAATCACGGAGCTTGCTGCGCGG
AGCTTGATATCTGGGAGGCAAACAGCATCTCAGAGGCCTTGACTCCTCACCCTTGCGATACACCCGGTCT
ATCTGTTTGCACTACTGATGCCTGCGGTGGTACCTACAGCTCTGATCGTTACGCCGGTACCTGCGACCCT
GATGGATGTGACTTCAACCCTTACCGCCTTGGTGTCACTGACTTCTACGGCTCCGGCAAGACCGTTGACA
CCACCAAGCCCTTTACCGTTGTGACTCAATTCGTCACTAACGACGGTACCTCCACCGGTTCCCTCTCCGA
GATCAGACGTTACTACGTTCAGAACGGCGTTGTCATCCCCCAGCCTTCCTCCAAGATCTCCGGAATCAGC
GGAAATGTCATCAACTCCGACTACTGCGCTGCTGAAATTTCCACCTTTGGCGGGACTGCCTCCTTCAGCA
AACACGGTGGCTTGACAAACATGGCCGCTGGTATGGAAGCTGGTATGGTCTTGGTCATGAGTTTGTGGGA
CGACTACGCCGTCAACATGCTCTGGCTCGACAGCACCTACCCTACAAACGCGACTGGTACCCCGGTGCC
GCTCGTGGTACCTGCGCTACCACTTCTGGGGACCCCAAGACCGTTGAATCACAATCCGGCAGCTCCTATG
TCACCTTCTCTGACATTCGGGTTGGTCCTTTCAATTCTACGTTCAGCGGTGGTTCTAGCACCGGTGGCAG
CACTACTACTACCGCCAGCCGCACCACCACCACCTCGGCCTCTTCCACCTCTACTTCCAGCACCTCTACT
GGCACTGGATAAGGATCCAAGCTGGCTGGCGGCGGCTACTGGCACACCTCCGGTCGCGAGATACTCGACG
CAAATAATGTTCCTGTCCGAATCGCGGGGATTAACTGGTTCGGATTCGAGACGTGCAATTACGTTGTCCA
TGGCCTTTGGTCCCGAGATTACCGCTCAATGCTCGACCAGATCAAGTCGCTCGGTTACAACACGATTCGT
CTACCGTATTCTGACGACATCCTTAAGCCCGGCACCATGCCAAATAGCATCAATTTTTACCAAATGAACC
AAGACCTGCAGGGGCTTACTTCCCTGCAGGTGATGGACAAGATCGTTGCCTACGCCGGCCAGATCGGACT
GCGTATCATCCTGGACCGCCACCGGCCGGACTGCAGCGGCCAGTCGGCCTTGTGGTACACGAGCAGCGTT
TCGGAGGCCACATGGATTTCCGACCTGCAGGCTTTGGCCCAGCGCTACAAGGGAAACCCAACTGTCGTAG
GCTTCGACCTCCACAACGAGCCCCACGACCCCGCATGCTGGGGATGCGGCGATCCGTCGATTGACTGGAG
GCTCGCTGCCGAACGTGCTGGTAACGCTGTCTTGTCCGTGAACCCAAACCTTCTGATCTTCGTCGAAGGC
GTTCAGTCTTACAATGGAGATTCGTACTGGTGGGCGGAAACCTTCAGGGCGCTGGCCAATACCCGGTCG
TTCTCAACGTTCCGAACCGGCTTGTTTACAGCGCACACGACTACGCCACGAGCGTCGGCCCTCAAACCTG
GTTCTCCGACCCTACATTCCCCAACAACATGCCAGGAATCTGGAACAAGAATTGGGGCTACCTTTTCAAC
CAGAACATCGCTCCCGTTTGGCTGGGCGAGTTTGGCACAACGTTGCAGTCTACGACGGACCAAACATGGC
TGAAGACCCTCGTCCAGTATCTCAGGCCCACCGCGCAGTATGGTGCGGACAGCTTTCAGTGGACCTTCTG
GTCTTGGAACCCCGATTCTGGCGACACAGGCGGTATCCTGAAGGATGATTGGCAGACGGTTGACACAGTC
AAGGACGGTTATCTGGCACCTATCAAGTCCAGCATCTTCGACCCCGTT

MSALNSFNMYKSALILGSLLATAGAQQIGTYTAETHPSLSWSTCKSGGSCTTNSGAITLDANWR
WVHGVNTSTNCYTGNTWNSAICDTDASCAQDCALDGADYSGTYGITTSGNSLRLNFVTGSNVGS
RTYLMADNTHYQIFDLLNQEFTFTVDVSHLPCGLNGALYFVTMDADGGVSKYPNNKAGAQYGVG
YCDSQCPRDLKFIAGQANVEGWTPSANNANTGIGNHGACCAELDIWEANSISEALTPHPCDTPG
LSVCTTDACGGTYSSDRYAGTCDPDGCDFNPYRLGVTDFYGSGKTVDTTKPFTVVTQFVTNDGT
STGSLSEIRRYYVQNGVVIPQPSSKISGISGNVINSDYCAAEISTFGGTASFSKHGGLTNMAAG
MEAGMVLVMSLWDDYAVNMLWLDSTYPTNATGTPGAARGTCATTSGDPKTVESQSGSSYVTFSD
IRVGPFNSTFSGGSSTGGSTTTTASRTTTTSASSTSTSSTSTGTGGSKLAGGGYWHTSGREILD
ANNVPVRIAGINWFGFETCNYVVHGLWSRDYRSMLDQIKSLGYNTIRLPYSDDILKPGTMPNSI
NFYQMNQDLQGLTSLQVMDKIVAYAGQIGLRIILDRHRPDCSGQSALWYTSSVSEATWISDLQA
LAQRYKGNPTVVGFDLHNEPHDPACWGCGDPSIDWRLAAERAGNAVLSVNPNLLIFVEGVQSYN
GDSYWWGGNLQGAGQYPVVLNVPNRLVYSAHDYATSVGPQTWFSDPTFPNNMPGIWNKNWGYLF
NQNIAPVWLGEFGTTLQSTTDQTWLKTLVQYLRPTAQYGADSFQWTFWSWNPDSGDTGGILKDD
WQTVDTVKDGYLAPIKSSIFDPV

```
ATGTCTGCCTTGAACTCTTTCAATATGTACAAGAGCGCCCTCATCTTGGGCTCCTTGCTGGCAACAGCTG
GTGCTCAGCAAATTGGTACTTATACCGCTGAAACCCATCCCTCTCTGAGCTGGTCTACTTGCAAATCGGG
TGGTAGCTGCACCACAAACTCCGGTGCCATTACGTTAGATGCCAACTGGCGTTGGGTCCATGGTGTCAAT
ACCAGCACCAACTGCTACACTGGCAACACTTGGAATAGCGCCATCTGCGACACTGATGCATCCTGTGCCC
AGGACTGTGCTCTCGATGGTGCTGACTACTCTGGCACGTACGGTATCACTACCTCCGGCAACTCATTGCG
CCTGAACTTCGTTACCGGTTCCAACGTCGGATCTCGTACTTACCTGATGGCCGATAACACCCACTACCAA
ATCTTCGATCTGTTGAACCAGGAGTTCACCTTCACCGTCGATGTCTCCCACCTCCCTTGCGGTTTGAACG
GTGCCCTCTACTTCGTGACCATGGATGCCGACGGTGGCGTCTCCAAGTACCCCAACAACAAGGCCGGTGC
TCAGTACGGTGTTGGATACTGTGACTCTCAATGCCCTCGTGACTTGAAGTTCATCGCTGGTCAGGCCAAC
GTTGAGGGCTGGACGCCCTCCGCCAACAACGCCAACACTGGAATTGGCAATCACGGAGCTTGCTGCGCGG
AGCTTGATATCTGGGAGGCAAACAGCATCTCAGAGGCCTTGACTCCTCACCCTTGCGATACACCCGGTCT
ATCTGTTTGCACTACTGATGCCTGCGGTGGTACCTACAGCTCTGATCGTTACGCCGGTACCTGCGACCCT
GATGGATGTGACTTCAACCCTTACCGCCTTGGTGTCACTGACTTCTACGGCTCCGGCAAGACCGTTGACA
CCACCAAGCCCTTTACCGTTGTGACTCAATTCGTCACTAACGACGGTACCTCCACCGGTTCCCTCTCCGA
GATCAGACGTTACTACGTTCAGAACGGCGTTGTCATCCCCCAGCCTTCCTCCAAGATCTCCGGAATCAGC
GGAAATGTCATCAACTCCGACTACTGCGCTGCTGAAATTTCCACCTTTGGCGGGACTGCCTCCTTCAGCA
AACACGGTGGCTTGACAAACATGGCCGCTGGTATGGAAGCTGGTATGGTCTTGGTCATGAGTTTGTGGGA
CGACTACGCCGTCAACATGCTCTGGCTCGACAGCACCTACCCTACAAACGCGACTGGTACCCCGGTGCC
GCTCGTGGTACCTGCGCTACCACTTCTGGGGACCCCAAGACCGTTGAATCACAATCCGGCAGCTCCTATG
TCACCTTCTCTGACATTCGGGTTGGTCCTTTCAATTCTACGTTCAGCGGTGGTTCTAGCACCGGTGGCAG
CACTACTACTACCGCCAGCCGCACCACCACCACCTCGGCCTCTTCCACCTCTACTTCCAGCACCTCTACT
GGCACTGGAGGATCCGGCGCTGCAAGCTCAAGCTCGTCCACGCGCGCCGCGTCGACGACTTCTCGAGTAT
CCCCCACAACATCCCGGTCGAGCTCCGCGACGCCTCCACCTGGTTCTACTACTACCAGAGTACCTCCAGT
CGGATCGGGAAAGCTGGCTGGCGGCGGCTACTGGCACACCTCCGGTCGCGAGATACTCGACGCAAATAAT
GTTCCTGTCCGAATCGCGGGGATTAACTGGTTCGGATTCGAGACGTGCAATTACGTTGTCCATGGCCTTT
GGTCCCGAGATTACCGCTCAATGCTCGACCAGATCAAGTCGCTCGGTTACAACACGATTCGTCTACCGTA
TTCTGACGACATCCTTAAGCCCGGCACCATGCCAAATAGCATCAATTTTTACCAAATGAACCAAGACCTG
CAGGGGCTTACTTCCCTGCAGGTGATGGACAAGATCGTTGCCTACGCCGGCCAGATCGGACTGCGTATCA
TCCTGGACCGCCACCGGCCGGACTGCAGCGGCCAGTCGGCCTTGTGGTACACGAGCAGCGTTTCGGAGGC
CACATGGATTTCCGACCTGCAGGCTTTGGCCCAGCGCTACAAGGGAAACCCAACTGTCGTAGGCTTCGAC
CTCCACAACGAGCCCCACGACCCCGCATGCTGGGGATGCGGCGATCCGTCGATTGACTGGAGGCTCGCTG
CCGAACGTGCTGGTAACGCTGTCTTGTCCGTGAACCCAAACCTTCTGATCTTCGTCGAAGGCGTTCAGTC
TTACAATGGAGATTCGTACTGGTGGGGCGGAAACCTTCAGGGCGCTGGCCAATACCCGGTCGTTCTCAAC
GTTCCGAACCGGCTTGTTTACAGCGCACACGACTACGCCACGAGCGTCGGCCCTCAAACCTGGTTCTCCG
ACCCTACATTCCCCAACAACATGCCAGGAATCTGGAACAAGAATTGGGGCTACCTTTTCAACCAGAACAT
CGCTCCCGTTTGGCTGGGCGAGTTTGGCACAACGTTGCAGTCTACGACGGACCAAACATGGCTGAAGACC
CTCGTCCAGTATCTCAGGCCCACCGCGCAGTATGGTGCGGACAGCTTTCAGTGGACCTTCTGGTCTTGGA
ACCCCGATTCTGGCGACACAGGCGGTATCCTGAAGGATGATTGGCAGACGGTTGACACAGTCAAGGACGG
TTATCTGGCACCTATCAAGTCCAGCATCTTCGACCCCGTT
```

MSALNSFNMYKSALILGSLLATAGAQQIGTYTAETHPSLSWSTCKSGGSCTTNSGAITLDANWR
WVHGVNTSTNCYTGNTWNSAICDTDASCAQDCALDGADYSGTYGITTSGNSLRLNFVTGSNVGS
RTYLMADNTHYQIFDLLNQEFTFTVDVSHLPCGLNGALYFVTMDADGGVSKYPNNKAGAQYGVG
YCDSQCPRDLKFIAGQANVEGWTPSANNANTGIGNHGACCAELDIWEANSISEALTPHPCDTPG
LSVCTTDACGGTYSSDRYAGTCDPDGCDFNPYRLGVTDFYGSGKTVDTTKPFTVVTQFVTNDGT
STGSLSEIRRYYVQNGVVIPQPSSKISGISGNVINSDYCAAEISTFGGTASFSKHGGLTNMAAG
MEAGMVLVMSLWDDYAVNMLWLDSTYPTNATGTPGAARGTCATTSGDPKTVESQSGSSYVTFSD
IRVGPFNSTF**SGGSSTGGSTTTTASRTTTTSASSTSTSSTSTGTGGSGAASSSSSTRAASTTSR
VSPTTSRSSSATPPPGSTTTRVPPVGSG**KLAGGGYWHTSGREILDANNVPVRIAGINWFGFETC
NYVVHGLWSRDYRSMLDQIKSLGYNTIRLPYSDDILKPGTMPNSINFYQMNQDLQGLTSLQVMD
KIVAYAGQIGLRIILDRHRPDCSGQSALWYTSSVSEATWISDLQALAQRYKGNPTVVGFDLHNE
PHDPACWGCGDPSIDWRLAAERAGNAVLSVNPNLLIFVEGVQSYNGDSYWWGGNLQGAGQYPVV
LNVPNRLVYSAHDYATSVGPQTWFSDPTFPNNMPGIWNKNWGYLFNQNIAPVWLGEFGTTLQST
TDQTWLKTLVQYLRPTAQYGADSFQWTFWSWNPDSGDTGGILKDDWQTVDTVKDGYLAPIKSSI
FDPV

```
ATGTCTGCCTTGAACTCTTTCAATATGTACAAGAGCGCCCTCATCTTGGGCTCCTTGCTGGCAACAGCTGGTGCTCA
GCAAATTGGTACTTATACCGCTGAAACCCATCCCTCTCTGAGCTGGTCTACTTGCAAATCGGGTGGTAGCTGCACCA
CAAACTCCGGTGCCATTACGTTAGATGCCAACTGGCGTTGGGTCCATGGTGTCAATACCAGCACCAACTGCTACACT
GGCAACACTTGGAATAGCGCCATCTGCGACACTGATGCATCCTGTGCCCAGGACTGTGCTCTCGATGGTGCTGACTA
CTCTGGCACGTACGGTATCACTACCTCCGGCAACTCATTGCGCCTGAACTTCGTTACCGGTTCCAACGTCGGATCTC
GTACTTACCTGATGGCCGATAACACCCACTACCAAATCTTCGATCTGTTGAACCAGGAGTTCACCTTCACCGTCGAT
GTCTCCCACCTCCCTTGCGGTTTGAACGGTGCCCTCTACTTCGTGACCATGGATGCCGACGGTGGCGTCTCCAAGTA
CCCCAACAACAAGGCCGGTGCTCAGTACGGTGTTGGATACTGTGACTCTCAATGCCCTCGTGACTTGAAGTTCATCG
CTGGTCAGGCCAACGTTGAGGGCTGGACGCCCTCCGCCAACAACGCCAACACTGGAATTGGCAATCACGGAGCTTGC
TGCGCGGAGCTTGATATCTGGGAGGCAAACAGCATCTCAGAGGCCTTGACTCCTCACCCTTGCGATACACCCGGTCT
ATCTGTTTGCACTACTGATGCCTGCGGTGGTACCTACAGCTCTGATCGTTACGCCGGTACCTGCGACCCTGATGGAT
GTGACTTCAACCCTTACCGCCTTGGTGTCACTGACTTCTACGGCTCCGGCAAGACCGTTGACACCACCAAGCCCTTT
ACCGTTGTGACTCAATTCGTCACTAACGACGGTACCTCCACCGGTTCCCTCTCCGAGATCAGACGTTACTACGTTCA
GAACGGCGTTGTCATCCCCCAGCCTTCCTCCAAGATCTCCGGAATCAGCGGAAATGTCATCAACTCCGACTACTGCG
CTGCTGAAATTTCCACCTTTGGCGGGACTGCCTCCTTCAGCAAACACGGTGGCTTGACAAACATGGCCGCTGGTATG
GAAGCTGGTATGGTCTTGGTCATGAGTTTGTGGGACGACTACGCCGTCAACATGCTCTGGCTCGACAGCACCTACCC
TACAAACGCGACTGGTACCCCGGTGCCGCTCGTGGTACCTGCGCTACCACTTCTGGGGACCCCAAGACCGTTGAAT
CACAATCCGGCAGCTCCTATGTCACCTTCTCTGACATTCGGGTTGGTCCTTTCAATTCTACGTTCAGCGGTGGTTCT
AGCACCGGTGGCAGCACTACTACTACCGCCAGCCGCACCACCACCACCTCGGCCTCTTCCACCTCTACTTCCAGCAC
CTCTACTGGCACTGGAGGATCCGTTGCAGGTGGACAGATTAAAGTGCTCTATGCAAATAAGGAAACCAATTCAACAA
CGAACACGATTCGCCCGTGGCTGAAAGTCGTGAATACGGGGTCCAGTTCAATCGATCTCTCCCGCGTCACTATCCGC
TACTGGTACACCGTAGATGGCGATAAAGCACAATCCGCAATTTCGGATTGGGCCCAGATCGGTGCTAGCAACGTAAC
TTTTAAATTTGTCAAGCTGAGTAGCTCGGTTAGTGGGGCCGACTATTATCTGGAGATCGGTTTCAAAAGTGGAGCCG
GCCAGCTCCAGGCCGGTAAAGACACGGGAGAAATACAGATCCGCTTTAATAAATCCGACTGGAGCAATTATAACCAG
GGGAACGATTGGAGCTGGATGCAATCCATGACCTCTTACGGTGAAAATGTAAAGGTCACCGCATATATAGATGGCGT
ACTCGTCTGGGGCCAAGAACCTTCCGGAGCGGGCGCTGCAAGCTCAAGCTCGTCCACGCGCGCCGCGTCGACGACTT
CTCGAGTATCCCCCACAACATCCCGGTCGAGCTCCGCGACGCCTCCACCTGGTTCTACTACTACCAGAGTACCTCCA
GTCGGATCGGGAAAGCTGGCTGGCGGCGGCTACTGGCACACCTCCGGTCGCGAGATACTCGACGCAAATAATGTTCC
TGTCCGAATCGCGGGGATTAACTGGTTCGGATTCGAGACGTGCAATTACGTTGTCCATGGCCTTTGGTCCCGAGATT
ACCGCTCAATGCTCGACCAGATCAAGTCGCTCGGTTACAACACGATTCGTCTACCGTATTCTGACGACATCCTTAAG
CCCGGCACCATGCCAAATAGCATCAATTTTTACCAAATGAACCAAGACCTGCAGGGGCTTACTTCCCTGCAGGTGAT
GGACAAGATCGTTGCCTACGCCGGCCAGATCGGACTGCGTATCATCCTGGACCGCCACCGGCCGGACTGCAGCGGCC
AGTCGGCCTTGTGGTACACGAGCAGCGTTTCGGAGGCCACATGGATTTCCGACCTGCAGGCTTTGGCCCAGCGCTAC
AAGGGAAACCCAACTGTCGTAGGCTTCGACCTCCACAACGAGCCCCACGACCCCGCATGCTGGGGATGCGGCGATCC
GTCGATTGACTGGAGGCTCGCTGCCGAACGTGCTGGTAACGCTGTCTTGTCCGTGAACCCAAACCTTCTGATCTTCG
TCGAAGGCGTTCAGTCTTACAATGGAGATTCGTACTGGTGGGCGGAAACCTTCAGGGCGCTGGCCAATACCCGGTC
GTTCTCAACGTTCCGAACCGGCTTGTTTACAGCGCACACGACTACGCCACGAGCGTCGGCCCTCAAACCTGGTTCTC
CGACCCTACATTCCCCAACAACATGCCAGGAATCTGGAACAAGAATTGGGGCTACCTTTTCAACCAGAACATCGCTC
CCGTTTGGCTGGGCGAGTTTGGCACAACGTTGCAGTCTACGACGGACCAAACATGGCTGAAGACCCTCGTCCAGTAT
CTCAGGCCCACCGCGCAGTATGGTGCGGACAGCTTTCAGTGGACCTTCTGGTCTTGGAACCCCGATTCTGGCGACAC
AGGCGGTATCCTGAAGGATGATTGGCAGACGGTTGACACAGTCAAGGACGGTTATCTGGCACCTATCAAGTCCAGCA
TCTTCGACCCCGTT
```

MSALNSFNMYKSALILGSLLATAGAQQIGTYTAETHPSLSWSTCKSGGSCTTNSGAITLDANWR
WVHGVNTSTNCYTGNTWNSAICDTDASCAQDCALDGADYSGTYGITTSGNSLRLNFVTGSNVGS
RTYLMADNTHYQIFDLLNQEFTFTVDVSHLPCGLNGALYFVTMDADGGVSKYPNNKAGAQYGVG
YCDSQCPRDLKFIAGQANVEGWTPSANNANTGIGNHGACCAELDIWEANSISEALTPHPCDTPG
LSVCTTDACGGTYSSDRYAGTCDPDGCDFNPYRLGVTDFYGSGKTVDTTKPFTVVTQFVTNDGT
STGSLSEIRRYYVQNGVVIPQPSSKISGISGNVINSDYCAAEISTFGGTASFSKHGGLTNMAAG
MEAGMVLVMSLWDDYAVNMLWLDSTYPTNATGTPGAARGTCATTSGDPKTVESQSGSSYVTFSD
IRVGPFNSTFSGGSSTGGSTTTTASRTTTTSASSTSTSSTSTGTGGSVAGGQIKVLYANKETNS
TTNTIRPWLKVVNTGSSSIDLSRVTIRYWYTVDGDKAQSAISDWAQIGASNVTFKFVKLSSSVS
GADYYLEIGFKSGAGQLQAGKDTGEIQIRFNKSDWSNYNQGNDWSWMQSMTSYGENVKVTAYID
GVLVWGQEPSGAGAASSSSSTRAASTTSRVSPTTSRSSSATPPPGSTTTRVPPVGSGKLAGGGY
WHTSGREILDANNVPVRIAGINWFGFETCNYVVHGLWSRDYRSMLDQIKSLGYNTIRLPYSDDI
LKPGTMPNSINFYQMNQDLQGLTSLQVMDKIVAYAGQIGLRIILDRHRPDCSGQSALWYTSSVS
EATWISDLQALAQRYKGNPTVVGFDLHNEPHDPACWGCGDPSIDWRLAAERAGNAVLSVNPNLL
IFVEGVQSYNGDSYWWGGNLQGAGQYPVVLNVPNRLVYSAHDYATSVGPQTWFSDPTFPNNMPG
IWNKNWGYLFNQNIAPVWLGEFGTTLQSTTDQTWLKTLVQYLRPTAQYGADSFQWTFWSWNPDS
GDTGGILKDDWQTVDTVKDGYLAPIKSSIFDPV

ATGTATCGGAAGTTGGCCGTCATCTCGGCCTTCTTGGCCACAGCTCGTGCTCAGTCGGCCTGCACTCTCC
AATCGGAGACTCACCCGCCTCTGACATGGCAGAAATGCTCGTCTGGTGGCACGTGCACTCAACAGACAGG
CTCCGTGGTCATCGACGCCAACTGGCGCTGGACTCACGCTACGAACAGCAGCACGAACTGCTACGATGGC
AACACTTGGAGCTCGACCCTATGTCCTGACAACGAGACCTGCGCGAAGAACTGCTGTCTGGACGGTGCCG
CCTACGCGTCCACGTACGGAGTTACCACGAGCGGTAACAGCCTCTCCATTGGCTTTGTCACCCAGTCTGC
GCAGAAGAACGTTGGCGCTCGCCTTTACCTTATGGCGAGCGACACGACCTACCAGGAATTCACCCTGCTT
GGCAACGAGTTCTCTTTCGATGTTGATGTTTCGCAGCTGCCGTGCGGCTTGAACGGAGCTCTCTACTTCG
TGTCCATGGACGCGGATGGTGGCGTGAGCAAGTATCCCACCAACACCGCTGGCGCCAAGTACGGCACGGG
GTACTGTGACAGCCAGTGTCCCCGCGATCTGAAGTTCATCAATGGCCAGGCCAACGTTGAGGGCTGGGAG
CCGTCATCCAACAACGCGAACACGGGCATTGGAGGACACGGAAGCTGCTGCTCTGAGATGGATATCTGGG
AGGCCAACTCCATCTCCGAGGCTCTTACCCCCCACCCTTGCACGACTGTCGGCCAGGAGATCTGCGAGGG
TGATGGGTGCGGCGGAACTTACTCCGATAACAGATATGGCGGCACTTGCGATCCCGATGGCTGCGACTGG
AACCCATACCGCCTGGGCAACACCAGCTTCTACGGCCCTGGCTCAAGCTTTACCCTCGATACCACCAAGA
AATTGACCGTTGTCACCCAGTTCGAGACGTCGGGTGCCATCAACCGATACTATGTCCAGAATGGCGTCAC
TTTCCAGCAGCCCAACGCCGAGCTTGGTAGTTACTCTGGCAACGAGCTCAACGATGATTACTGCACAGCT
GAGGAGGCAGAATTCGGCGGCTCCTCTTTCTCAGACAAGGGCGGCCTGACTCAGTTCAAGAAGGCTACCT
CTGGCGGCATGGTTCTGGTCATGAGTCTGTGGGATGATTACTACGCCAACATGCTGTGGCTGGACTCCAC
CTACCCGACAAACGAGACCTCCTCCACACCCGGTGCCGTGCGCGGAAGCTGCTCCACCAGCTCCGGTGTC
CCTGCTCAGGTCGAATCTCAGTCTCCCAACGCCAAGGTCACCTTCTCCAACATCAAGTTCGGACCCATTG
GCAGCACCGGTTCTAGCACCGGTGGCAGCACTACTACTACCGCCAGCCGCACCACCACCACCTCGGCCTC
TTCCACCTCTACTTCCAGCACCTCTACTGGCACTGGAGGATCCAAGCTGGCTGGCGGCGGCTACTGGCAC
ACCTCCGGTCGCGAGATACTCGACGCAAATAATGTTCCTGTCCGAATCGCGGGGATTAACTGGTTCGGAT
TCGAGACGTGCAATTACGTTGTCCATGGCCTTTGGTCCCGAGATTACCGCTCAATGCTCGACCAGATCAA
GTCGCTCGGTTACAACACGATTCGTCTACCGTATTCTGACGACATCCTTAAGCCCGGCACCATGCCAAAT
AGCATCAATTTTTACCAAATGAACCAAGACCTGCAGGGGCTTACTTCCCTGCAGGTGATGGACAAGATCG
TTGCCTACGCCGGCCAGATCGGACTGCGTATCATCCTGGACCGCCACCGGCCGGACTGCAGCGGCCAGTC
GGCCTTGTGGTACACGAGCAGCGTTTCGGAGGCCACATGGATTTCCGACCTGCAGGCTTTGGCCCAGCGC
TACAAGGGAAACCCAACTGTCGTAGGCTTCGACCTCCACAACGAGCCCCACGACCCCGCATGCTGGGGAT
GCGGCGATCCGTCGATTGACTGGAGGCTCGCTGCCGAACGTGCTGGTAACGCTGTCTTGTCCGTGAACCC
AAACCTTCTGATCTTCGTCGAAGGCGTTCAGTCTTACAATGGAGATTCGTACTGGTGGGCGGAAACCTT
CAGGGCGCTGGCCAATACCCGGTCGTTCTCAACGTTCCGAACCGGCTTGTTTACAGCGCACACGACTACG
CCACGAGCGTCGGCCCTCAAACCTGGTTCTCCGACCCTACATTCCCAACAACATGCCAGGAATCTGGAA
CAAGAATTGGGGCTACCTTTTCAACCAGAACATCGCTCCCGTTTGGCTGGGCGAGTTTGGCACAACGTTG
CAGTCTACGACGGACCAAACATGGCTGAAGACCCTCGTCCAGTATCTCAGGCCCACCGCGCAGTATGGTG
CGGACAGCTTTCAGTGGACCTTCTGGTCTTGGAACCCCGATTCTGGCGACACAGGCGGTATCCTGAAGGA
TGATTGGCAGACGGTTGACACAGTCAAGGACGGTTATCTGGCACCTATCAAGTCCAGCATCTTCGACCCC
GTT

MYRKLAVISAFLATARAQSACTLQSETHPPLTWQKCSSGGTCTQQTGSVVIDANWRWTHATNSS
TNCYDGNTWSSTLCPDNETCAKNCCLDGAAYASTYGVTTSGNSLSIGFVTQSAQKNVGARLYLM
ASDTTYQEFTLLGNEFSFDVDVSQLPCGLNGALYFVSMDADGGVSKYPTNTAGAKYGTGYCDSQ
CPRDLKFINGQANVEGWEPSSNNANTGIGGHGSCCSEMDIWEANSISEALTPHPCTTVGQEICE
GDGCGGTYSDNRYGGTCDPDGCDWNPYRLGNTSFYGPGSSFTLDTTKKLTVVTQFETSGAINRY
YVQNGVTFQQPNAELGSYSGNELNDDYCTAEEAEFGGSSFSDKGGLTQFKKATSGGMVLVMSLW
DDYYANMLWLDSTYPTNETSSTPGAVRGSCSTSSGVPAQVESQSPNAKVTFSNIKFGPIGSTGS
STGGSTTTTASRTTTTSASSTSTSSTSTGTGGSKLAGGGYWHTSGREILDANNVPVRIAGINWF
GFETCNYVVHGLWSRDYRSMLDQIKSLGYNTIRLPYSDDILKPGTMPNSINFYQMNQDLQGLTS
LQVMDKIVAYAGQIGLRIILDRHRPDCSGQSALWYTSSVSEATWISDLQALAQRYKGNPTVVGF
DLHNEPHDPACWGCGDPSIDWRLAAERAGNAVLSVNPNLLIFVEGVQSYNGDSYWWGGNLQGAG
QYPVVLNVPNRLVYSAHDYATSVGPQTWFSDPTFPNNMPGIWNKNWGYLFNQNIAPVWLGEFGT
TLQSTTDQTWLKTLVQYLRPTAQYGADSFQWTFWSWNPDSGDTGGILKDDWQTVDTVKDGYLAP
IKSSIFDPV

ATGTCTGCCTTGAACTCTTTCAATATGTACAAGAGCGCCCTCATCTTGGGCTCCTTGCTGGCAACAGCTGGTGCTCA
GCAAATTGGTACTTATACCGCTGAAACCCATCCCTCTCTGAGCTGGTCTACTTGCAAATCGGGTGGTAGCTGCACCA
CAAACTCCGGTGCCATTACGTTAGATGCCAACTGGCGTTGGGTCCATGGTGTCAATACCAGCACCAACTGCTACACT
GGCAACACTTGGAATAGCGCCATCTGCGACACTGATGCATCCTGTGCCCAGGACTGTGCTCTCGATGGTGCTGACTA
CTCTGGCACGTACGGTATCACTACCTCCGGCAACTCATTGCGCCTGAACTTCGTTACCGGTTCCAACGTCGGATCTC
GTACTTACCTGATGGCCGATAACACCCACTACCAAATCTTCGATCTGTTGAACCAGGAGTTCACCTTCACCGTCGAT
GTCTCCCACCTCCCTTGCGGTTTGAACGGTGCCCTCTACTTCGTGACCATGGATGCCGACGGTGGCGTCTCCAAGTA
CCCCAACAACAAGGCCGGTGCTCAGTACGGTGTTGGATACTGTGACTCTCAATGCCCTCGTGACTTGAAGTTCATCG
CTGGTCAGGCCAACGTTGAGGGCTGGACGCCCTCCGCCAACAACGCCAACACTGGAATTGGCAATCACGGAGCTTGC
TGCGCGGAGCTTGATATCTGGGAGGCAAACAGCATCTCAGAGGCCTTGACTCCTCACCCTTGCGATACACCCGGTCT
ATCTGTTTGCACTACTGATGCCTGCGGTGGTACCTACAGCTCTGATCGTTACGCCGGTACCTGCGACCCTGATGGAT
GTGACTTCAACCCTTACCGCCTTGGTGTCACTGACTTCTACGGCTCCGGCAAGACCGTTGACACCACCAAGCCCTTT
ACCGTTGTGACTCAATTCGTCACTAACGACGGTACCTCCACCGGTTCCCTCTCCGAGATCAGACGTTACTACGTTCA
GAACGGCGTTGTCATCCCCCAGCCTTCCTCCAAGATCTCCGGAATCAGCGGAAATGTCATCAACTCCGACTACTGCG
CTGCTGAAATTTCCACCTTTGGCGGGACTGCCTCCTTCAGCAAACACGGTGGCTTGACAAACATGGCCGCTGGTATG
GAAGCTGGTATGGTCTTGGTCATGAGTTTGTGGGACGACTACGCCGTCAACATGCTCTGGCTCGACAGCACCTACCC
TACAAACGCGACTGGTACCCCGGTGCCGCTCGTGGTACCTGCGCTACCACTTCTGGGGACCCCAAGACCGTTGAAT
CACAATCCGGCAGCTCCTATGTCACCTTCTCTGACATTCGGGTTGGTCCTTTCAATTCTACGTTCAGCGGTGGTTCT
AGCACCGGTGGCAGCACTACTACTACCGCCAGCCGCACCACCACCACCTCGGCCTCTTCCACCTCTACTTCCAGCAC
CTCTACTGGCACTGGAGGATCCGGCGCTGCAAGCTCAAGCTCGTCCACGCGCGCCGCGTCGACGACTTCTCGAGTAT
CCCCCACAACATCCCGGTCGAGCTCCGCGACGCCTCCACCTGGTTCTACTACTACCAGAGTACCTCCAGTCGGATCG
GGATACAACTACGGCGAGGCCCTCCAGAAGTCCATTATGTTTTACGAGTTTCAGCGCAGCGGCAAGCTCCCCTCCAC
CATTCGCAACAACTGGCGCGGCGACTCGGGCCTCACCGACGGCGCCGACGTCGGCCTGGACCTCACCGGCGGCTGGT
ACGACGCCGGCGACCACGTCAAGTTCAACCTGCCCCTCGCCTACACCGTCACCATGCTGGCCTGGGCCGTCTACGAG
GAAGAGGCCACCCTGAGCAAGGCCGGCCAGCTCTCCTACCTCCTGGACGAGATCAAGTGGAGCAGCGACTACCTCAT
CAAGTGCCACCCCCAGGCCAACGTCTTCTACTACCAGGTCGGCAACGGCAACACCGACCACAGCTGGTGGGGCCCCG
CCGAGGTCATGCAGATGGCCCGCCCTAGCTACAAGGTGGACCTCAACAACCCCGGCTCCACCGTCGTCGGCGAGGCC
GCCGCCGCCCTCGCCGCCACCGCCCTCATCTACAAGACCAAGGACCCCACCTACTCGGCCACCTGCCTGCGCCACGC
CAAGGAGCTGTTCAACTTCGCCGACACCACCAAGTCGGACGCCGGCTACACCGCCGCCTCCGGCTTCTACACCAGCT
ACTCCGGCTTCTACGACGAGCTGAGCTGGGCCGCCACCTGGATCTACCTGGCCTCCGGCGAGGCCACCTACCTCGAC
AAGGCCGAGAGGTACGTCGCCAAGTGGGGCACCGAGCCCCAGAGCAGCACCCTCTCCTACAAGTGGGCCCAGAACTG
GGACGACGTCCACTACGGCGCCGCCCTCCTGCTCGCCCGCATCACCAACAAGGCCATCTACAAGAACAACATCGAGA
TGCACCTGGACTACTGGACCACCGGCTACAACGGCAGCCGCATCACCTACACCCCCAAGGGCCTGGCCTGGCTGGAC
TCCTGGGGCGCCCTGCGCTACGCCACCACCACCGCCTTCCTCGCCAGCGTCTACGCCGACTGGTCGGGCTGCTCCGC
CGGCAAGGTCAGCACCTACAACGCCTTCGCCAAGCAGCAGGTGGACTACGCCCTCGGCAGCACCGGCCGCTCCTTCG
TCGTCGGCTACGGCGTCAACAGCCCCACCCGCCCCACCACCGCACCGCCCACAGCTCCTGGGCCGACTCCCAGACC
GAGCCCAACTACCACCGCCACACCATCTACGGCGCCCTGGTCGGCGGCCCCGGCAACAACGACTCCTACGAGGACAA
CATCAACAACTACGTCAACAACGAGATCGCCTGCGACTACAACGCCGGCTTCGTCGGCGCCCTGGCCAAGGTCTACA
AGACCTACGGCGGCACCCCCATCGCCAACTTCAAGGCCATCGAGACGGTCACCAACGACGAGCTGTTCATCCAGGCC
GGCATCAACGCCAGCGGCCCCTCCTTCATCGAGGTCAAGGCCCTGGTCTTCAACGAGACGGGCTGGCCCGCCCGCGT
CACCGACAAGCTCAGCTTCAAGTACTTCATCGACATCTCCGAGTACGTCGCCAAGGGCTACACCAAGAACGACTTCA
CCGTCAGCACCAACTACAACAACGGCGCCACCACCTCCGCCCTGCTCCCTGGGACGCCGCCAACAACATCTACTAC
GTCAACGTGGACTTCAGCGGCACCAAGATTTACCCCGGCGGCCAGTCCGCCTACAAGAAGGAAGTCCAGTTCCGCAT
CGCCGGCCCCAGAACGTCAACATCTGGGACAACAGCAACGACTACTCCTTCACCCAGATCGCCAACGTCAGCTCCG
GCAACACCGTCAAGACGACCTACATCCCCCTCTACGACAACGGCAAGCTGGTCTTCGGCAACGAGCCC

MSALNSFNMYKSALILGSLLATAGAQQIGTYTAETHPSLSWSTCKSGGSCTTNSGAITLDANWR
WVHGVNTSTNCYTGNTWNSAICDTDASCAQDCALDGADYSGTYGITTSGNSLRLNFVTGSNVGS
RTYLMADNTHYQIFDLLNQEFTFTVDVSHLPCGLNGALYFVTMDADGGVSKYPNNKAGAQYGVG
YCDSQCPRDLKFIAGQANVEGWTPSANNANTGIGNHGACCAELDIWEANSISEALTPHPCDTPG
LSVCTTDACGGTYSSDRYAGTCDPDGCDFNPYRLGVTDFYGSGKTVDTTKPFTVVTQFVTNDGT
STGSLSEIRRYYVQNGVVIPQPSSKISGISGNVINSDYCAAEISTFGGTASFSKHGGLTNMAAG
MEAGMVLVMSLWDDYAVNMLWLDSTYPTNATGTPGAARGTCATTSGDPKTVESQSGSSYVTFSD
IRVGPFNSTF**SGGSSTGGSTTTTASRTTTTSASSTSTSSTSTGTGGSGAASSSSSTRAASTTSR
VSPTTSRSSSATPPPGSTTTRVPPVGSG**YNYGEALQKSIMFYEFQRSGKLPSTIRNNWRGDSGL
TDGADVGLDLTGGWYDAGDHVKFNLPLAYTVTMLAWAVYEEEATLSKAGQLSYLLDEIKWSSDY
LIKCHPQANVFYYQVGNGNTDHSWWGPAEVMQMARPSYKVDLNNPGSTVVGEAAAALAATALIY
KTKDPTYSATCLRHAKELFNFADTTKSDAGYTAASGFYTSYSGFYDELSWAATWIYLASGEATY
LDKAESYVAKWGTEPQSSTLSYKWAQNWDDVHYGAALLARITNKAIYKNNIEMHLDYWTTGYN
GSRITYTPKGLAWLDSWGALRYATTTAFLASVYADWSGCSAGKVSTYNAFAKQQVDYALGSTGR
SFVVGYGVNSPTRPHHRTAHSSWADSQTEPNYHRHTIYGALVGGPGNNDSYEDNINNYVNNEIA
CDYNAGFVGALAKVYKTYGGTPIANFKAIETVTNDELFIQAGINASGPSFIEVKALVFNETGWP
ARVTDKLSFKYFIDISEYVAKGYTKNDFTVSTNYNNGATTSALLPWDAANNIYYVNVDFSGTKI
YPGGQSAYKKEVQFRIAGPQNVNIWDNSNDYSFTQIANVSSGNTVKTTYIPLYDNGKLVFGNEP

ATGTCTGCCTTGAACTCTTTCAATATGTACAAGAGCGCCCTCATCTTGGGCTCCTTGCTGGCAACAGCTG
GTGCTCAGCAAATTGGTACTTATACCGCTGAAACCCATCCCTCTCTGAGCTGGTCTACTTGCAAATCGGG
TGGTAGCTGCACCACAAACTCCGGTGCCATTACGTTAGATGCCAACTGGCGTTGGGTCCATGGTGTCAAT
ACCAGCACCAACTGCTACACTGGCAACACTTGGAATAGCGCCATCTGCGACACTGATGCATCCTGTGCCC
AGGACTGTGCTCTCGATGGTGCTGACTACTCTGGCACGTACGGTATCACTACCTCCGGCAACTCATTGCG
CCTGAACTTCGTTACCGGTTCCAACGTCGGATCTCGTACTTACCTGATGGCCGATAACACCCACTACCAA
ATCTTCGATCTGTTGAACCAGGAGTTCACCTTCACCGTCGATGTCTCCCACCTCCCTTGCGGTTTGAACG
GTGCCCTCTACTTCGTGACCATGGATGCCGACGGTGGCGTCTCCAAGTACCCAACAACAAGGCCGGTGC
TCAGTACGGTGTTGGATACTGTGACTCTCAATGCCCTCGTGACTTGAAGTTCATCGCTGGTCAGGCCAAC
GTTGAGGGCTGGACGCCCTCCGCCAACAACGCCAACACTGGAATTGGCAATCACGGAGCTTGCTGCGCGG
AGCTTGATATCTGGGAGGCAAACAGCATCTCAGAGGCCTTGACTCCTCACCCTTGCGATACACCCGGTCT
ATCTGTTTGCACTACTGATGCCTGCGGTGGTACCTACAGCTCTGATCGTTACGCCGGTACCTGCGACCCT
GATGGATGTGACTTCAACCCTTACCGCCTTGGTGTCACTGACTTCTACGGCTCCGGCAAGACCGTTGACA
CCACCAAGCCCTTTACCGTTGTGACTCAATTCGTCACTAACGACGGTACCTCCACCGGTTCCCTCTCCGA
GATCAGACGTTACTACGTTCAGAACGGCGTTGTCATCCCCCAGCCTTCCTCCAAGATCTCCGGAATCAGC
GGAAATGTCATCAACTCCGACTACTGCGCTGCTGAAATTTCCACCTTTGGCGGGACTGCCTCCTTCAGCA
AACACGGTGGCTTGACAAACATGGCCGCTGGTATGGAAGCTGGTATGGTCTTGGTCATGAGTTTGTGGGA
CGACTACGCCGTCAACATGCTCTGGCTCGACAGCACCTACCCTACAAACGCGACTGGTACCCCGGTGCC
GCTCGTGGTACCTGCGCTACCACTTCTGGGGACCCCAAGACCGTTGAATCACAATCCGGCAGCTCCTATG
TCACCTTCTCTGACATTCGGGTTGGTCCTTTCAATTCTACGTTCAGCGGTGGTTCTAGCACCGGTGGCAG
CACTACTACTACCGCCAGCCGCACCACCACCACCTCGGCCTCTTCCACCTCTACTTCCAGCACCTCTACT
GGCACTGGAGGATCCGTCGCTGGTCACTGGGGTCAGTGTGGTGGCCAGGGCTGGACTGGCCCTACCACCT
GTGTTAGTGGAACCACATGCACCGTCGTGAACCCTTACTACTCTCAATGTTTGGGCGCTGCAAGCTCAAG
CTCGTCCACGCGCGCCGCGTCGACGACTTCTCGAGTATCCCCCACAACATCCCGGTCGAGCTCCGCGACG
CCTCCACCTGGTTCTACTACTACCAGAGTACCTCCAGTCGGATCGGGAAAGCTGGCTGGCGGCGGCTACT
GGCACACCTCCGGTCGCGAGATACTCGACGCAAATAATGTTCCTGTCCGAATCGCGGGGATTAACTGGTT
CGGATTCGAGACGTGCAATTACGTTGTCCATGGCCTTTGGTCCCGAGATTACCGCTCAATGCTCGACCAG
ATCAAGTCGCTCGGTTACAACACGATTCGTCTACCGTATTCTGACGACATCCTTAAGCCCGGCACCATGC
CAAATAGCATCAATTTTTACCAAATGAACCAAGACCTGCAGGGGCTTACTTCCCTGCAGGTGATGGACAA
GATCGTTGCCTACGCCGGCCAGATCGGACTGCGTATCATCCTGGACCGCCACCGGCCGGACTGCAGCGGC
CAGTCGGCCTTGTGGTACACGAGCAGCGTTTCGGAGGCCACATGGATTTCCGACCTGCAGGCTTTGGCCC
AGCGCTACAAGGGAAACCCAACTGTCGTAGGCTTCGACCTCCACAACGAGCCCACGACCCCGCATGCTG
GGGATGCGGCGATCCGTCGATTGACTGGAGGCTCGCTGCCGAACGTGCTGGTAACGCTGTCTTGTCCGTG
AACCCAAACCTTCTGATCTTCGTCGAAGGCGTTCAGTCTTACAATGGAGATTCGTACTGGTGGGGCGGAA
ACCTTCAGGGCGCTGGCCAATACCCGGTCGTTCTCAACGTTCCGAACCGGCTTGTTTACAGCGCACACGA
CTACGCCACGAGCGTCGGCCCTCAAACCTGGTTCTCCGACCCTACATTCCCCAACAACATGCCAGGAATC
TGGAACAAGAATTGGGGCTACCTTTTCAACCAGAACATCGCTCCCGTTTGCTGGGCGAGTTTGGCACAA
CGTTGCAGTCTACGACGGACCAAACATGGCTGAAGACCCTCGTCCAGTATCTCAGGCCCACCGCGCAGTA
TGGTGCGGACAGCTTTCAGTGGACCTTCTGGTCTTGGAACCCCGATTCTGGCGACACAGGCGGTATCCTG
AAGGATGATTGGCAGACGGTTGACACAGTCAAGGACGGTTATCTGGCACCTATCAAGTCCAGCATCTTCG
ACCCCGTT

MSALNSFNMYKSALILGSLLATAGAQQIGTYTAETHPSLSWSTCKSGGSCTTNSGAITLDANWR
WVHGVNTSTNCYTGNTWNSAICDTDASCAQDCALDGADYSGTYGITTSGNSLRLNFVTGSNVGS
RTYLMADNTHYQIFDLLNQEFTFTVDVSHLPCGLNGALYFVTMDADGGVSKYPNNKAGAQYGVG
YCDSQCPRDLKFIAGQANVEGWTPSANNANTGIGNHGACCAELDIWEANSISEALTPHPCDTPG
LSVCTTDACGGTYSSDRYAGTCDPDGCDFNPYRLGVTDFYGSGKTVDTTKPFTVVTQFVTNDGT
STGSLSEIRRYYVQNGVVIPQPSSKISGISGNVINSDYCAAEISTFGGTASFSKHGGLTNMAAG
MEAGMVLVMSLWDDYAVNMLWLDSTYPTNATGTPGAARGTCATTSGDPKTVESQSGSSYVTFSD
IRVGPFNSTFSGGSSTGGSTTTTASRTTTTSASSTSTSSTSTGTGGSVAGHWGQCGGQGWTGPT
TCVSGTTCTVVNPYYSQCLGAASSSSSTRAASTTSRVSPTTSRSSSATPPPGSTTTRVPPVGSG
KLAGGGYWHTSGREILDANNVPVRIAGINWFGFETCNYVVHGLWSRDYRSMLDQIKSLGYNTIR
LPYSDDILKPGTMPNSINFYQMNQDLQGLTSLQVMDKIVAYAGQIGLRIILDRHRPDCSGQSAL
WYTSSVSEATWISDLQALAQRYKGNPTVVGFDLHNEPHDPACWGCGDPSIDWRLAAERAGNAVL
SVNPNLLIFVEGVQSYNGDSYWWGGNLQGAGQYPVVLNVPNRLVYSAHDYATSVGPQTWFSDPT
FPNNMPGIWNKNWGYLFNQNIAPVWLGEFGTTLQSTTDQTWLKTLVQYLRPTAQYGADSFQWTF
WSWNPDSGDTGGILKDDWQTVDTVKDGYLAPIKSSIFDPV

FIGURE 21
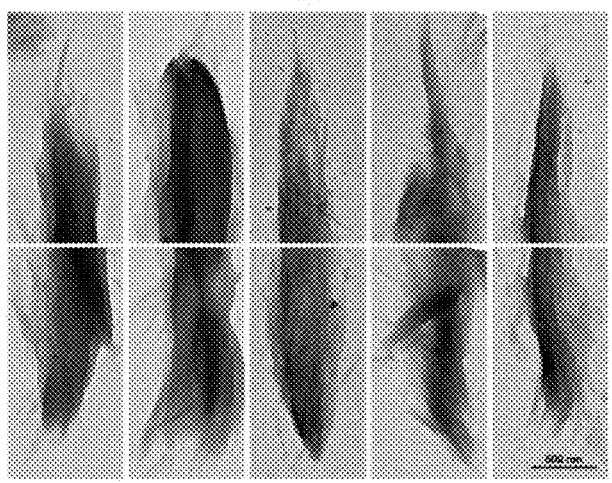
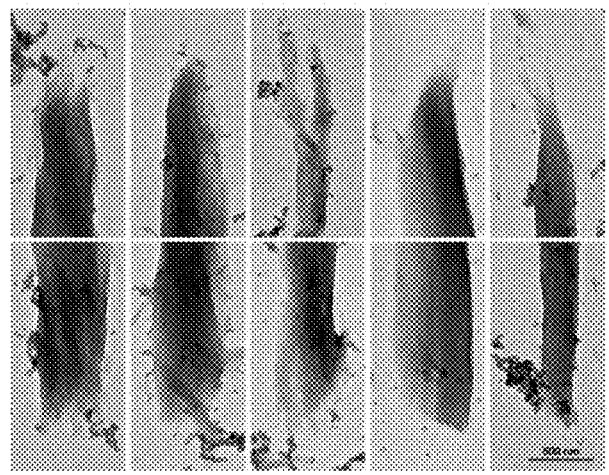
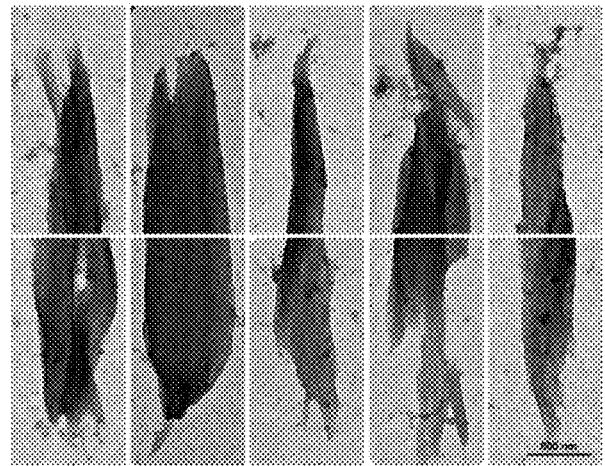

FIGURE 24A

HC10-CBM1-E1 (cDNA sequence)

ATGTCTGCCTTGAACTCTTTCAATATGTACAAGAGCGCCCTCATCTTGGGCTCCTTGCTGGCAACAGCTGGTGCTCA
GCAAATTGGTACTTATACCGCTGAAACCCATCCCTCTCTGAGCTGGTCTACTTGCAAATCGGGTGGTAGCTGCACC
ACAAACTCCGGTGCCATTACGTTAGATGCCAACTGGCGTTGGGTCCATGGTGTCAATACCAGCACCAACTGCTACA
CTGGCAACACTTGGAATAGCGCCATCTGCGACACTGATGCATCCTGTGCCCAGGACTGTGCTCTCGATGGTGCTGA
CTACTCTGGCACGTACGGTATCACTACCTCCGGCAACTCATTGCGCCTGAACTTCGTTACCGGTTCCAACGTCGGAT
CTCGTACTTACCTGATGGCCGATAACACCCACTACCAAATCTTCGATCTGTTGAACCAGGAGTTCACCTTCACCGTC
GATGTCTCCCACCTCCCTTGCGGTTTGAACGGTGCCCTCTACTTCGTGACCATGGATGCCGACGGTGGCGTCTCCA
AGTACCCCAACAACAAGGCCGGTGCTCAGTACGGTGTTGGATACTGTGACTCTCAATGCCCTCGTGACTTGAAGTT
CATCGCTGGTCAGGCCAACGTTGAGGGCTGGACGCCCTCCGCCAACAACGCCAACACTGGAATTGGCAATCACGG
AGCTTGCTGCGCGGAGCTTGATATCTGGGAGGCAAACAGCATCTCAGAGGCCTTGACTCCTCACCCTTGCGATACA
CCCGGTCTATCTGTTTGCACTACTGATGCCTGCGGTGGTACCTACAGCTCTGATCGTTACGCCGGTACCTGCGACCC
TGATGGATGTGACTTCAACCCTTACCGCCTTGGTGTCACTGACTTCTACGGCTCCGGCAAGACCGTTGACACCACC
AAGCCCTTTACCGTTGTGACTCAATTCGTCACTAACGACGGTACCTCCACCGGTTCCCTCTCCGAGATCAGACGTTA
CTACGTTCAGAACGGCGTTGTCATCCCCCAGCCTTCCTCCAAGATCTCCGGAATCAGCGGAAATGTCATCAACTCC
GACTACTGCGCTGCTGAAATTTCCACCTTTGGCGGGACTGCCTCCTTCAGCAAACACGGTGGCTTGACAAACATGG
CCGCTGGTATGGAAGCTGGTATGGTCTTGGTCATGAGTTTGTGGGACGACTACGCCGTCAACATGCTCTGGCTCG
ACAGCACCTACCCTACAAACGCGACTGGTACCCCCGGTGCCGCTCGTGGTACCTGCGCTACCACTTCTGGGGACCC
CAAGACCGTTGAATCACAATCCGGCAGCTCCTATGTCACCTTCTCTGACATTCGGGTTGGTCCTTTCAATTCTACGTT
CAGCGGTGGTTCTAGCACCGGTGGCAGCACTACTACTACCGCCAGCCGCACCACCACCACCTCGGCCTCTTCCACC
TCTACTTCCAGCACCTCTACTGGCACTGGAGGATCCGTCGCTGGTCACTGGGGTCAGTGTGGTGGCCAGGGCTGG
ACTGGCCCTACCACCTGTGTTAGTGGAACCACATGCACCGTCGTGAACCCTTACTACTCTCAATGTTTGGGCGCTGC
AAGCTCAAGCTCGTCCACGCGCGCCGCGTCGACGACTTCTCGAGTATCCCCCACAACATCCCGGTCGAGCTCCGCG
ACGCCTCCACCTGGTTCTACTACTACCAGAGTACCTCCAGTCGGATCGGGAAAGCTGGCTGGCGGCGGCTACTGG
CACACCTCCGGTCGCGAGATACTCGACGCAAATAATGTTCCTGTCCGAATCGCGGGGATTAACTGGTTCGGATTCG
AGACGTGCAATTACGTTGTCCATGGCCTTTGGTCCCGAGATTACCGCTCAATGCTCGACCAGATCAAGTCGCTCGG
TTACAACACGATTCGTCTACCGTATTCTGACGACATCCTTAAGCCCGGCACCATGCCAAATAGCATCAATTTTTACC
AAATGAACCAAGACCTGCAGGGGCTTACTTCCCTGCAGGTGATGGACAAGATCGTTGCCTACGCCGGCCAGATCG
GACTGCGTATCATCCTGGACCGCCACCGGCCGGACTGCAGCGGCCAGTCGGCCTTGTGGTACACGAGCAGCGTTT
CGGAGGCCACATGGATTTCCGACCTGCAGGCTTTGGCCCAGCGCTACAAGGGAAACCCAACTGTCGTAGGCTTCG
ACCTCCACAACGAGCCCCACGACCCCGCATGCTGGGGATGCGGCGATCCGTCGATTGACTGGAGGCTCGCTGCCG
AACGTGCTGGTAACGCTGTCTTGTCCGTGAACCCAAACCTTCTGATCTTCGTCGAAGGCGTTCAGTCTTACAATGG
AGATTCGTACTGGTGGGGCGGAAACCTTCAGGGCGCTGGCCAATACCCGGTCGTTCTCAACGTTCCGAACCGGCT
TGTTTACAGCGCACACGACTACGCCACGAGCGTCGGCCCTCAAACCTGGTTCTCCGACCCTACATTCCCCAACAAC
ATGCCAGGAATCTGGAACAAGAATTGGGGCTACCTTTTCAACCAGAACATCGCTCCCGTTTGGCTGGGCGAGTTTG
GCACAACGTTGCAGTCTACGACGGACCAAACATGGCTGAAGACCCTCGTCCAGTATCTCAGGCCCACCGCGCAGT
ATGGTGCGGACAGCTTTCAGTGGACCTTCTGGTCTTGGAACCCCGATTCTGGCGACACAGGCGGTATCCTGAAGG
ATGATTGGCAGACGGTTGACACAGTCAAGGACGGTTATCTGGCACCTATCAAGTCCAGCATCTTCGACCCCGTTTA
A

FIGURE 24B

HC10-CBM1-E1 (Protein sequence)

MSALNSFNMYKSALILGSLLATAGAQQIGTYTAETHPSLSWSTCKSGGSCTTNSGAITLDANWRWVHGVNTSTNCYTG
NTWNSAICDTDASCAQDCALDGADYSGTYGITTSGNSLRLNFVTGSNVGSRTYLMADNTHYQIFDLLNQEFTFTVDVS
HLPCGLNGALYFVTMDADGGVSKYPNNKAGAQYGVGYCDSQCPRDLKFIAGQANVEGWTPSANNANTGIGNHGAC
CAELDIWEANSISEALTPHPCDTPGLSVCTTDACGGTYSSDRYAGTCDPDGCDFNPYRLGVTDFYGSGKTVDTTKPFTV
VTQFVTNDGTSTGSLSEIRRYYVQNGVVIPQPSSKISGISGNVINSDYCAAEISTFGGTASFSKHGGLTNMAAGMEAGM
VLVMSLWDDYAVNMLWLDSTYPTNATGTPGAARGTCATTSGDPKTVESQSGSSYVTFSDIRVGPFNSTFSGGSSTGG
STTTTASRTTTTSASSTSTSSTSTGTGGSVAGHWGQCGGQGWTGPTTCVSGTTCTVVNPYYSQCLGAASSSSSTRAAST
TSRVSPTTSRSSSATPPPGSTTTRVPPVGSGKLAGGGYWHTSGREILDANNVPVRIAGINWFGFETCNYVVHGLWSRD
YRSMLDQIKSLGYNTIRLPYSDDILKPGTMPNSINFYQMNQDLQGLTSLQVMDKIVAYAGQIGLRIILDRHRPDCSGQSA
LWYTSSVSEATWISDLQALAQRYKGNPTVVGFDLHNEPHDPACWGCGDPSIDWRLAAERAGNAVLSVNPNLLIFVEG
VQSYNGDSYWWGGNLQGAGQYPVVLNVPNRLVYSAHDYATSVGPQTWFSDPTFPNNMPGIWNKNWGYLFNQNI
APVWLGEFGTTLQSTTDQTWLKTLVQYLRPTAQYGADSFQWTFWSWNPDSGDTGGILKDDWQTVDTVKDGYLAPI
KSSIFDPV

FIGURE 25A

HC10-2Link-E1 (cDNA sequence)

ATGTCTGCCTTGAACTCTTTCAATATGTACAAGAGCGCCCTCATCTTGGGCTCCTTGCTGGCAACAGCTGGTGCTCA
GCAAATTGGTACTTATACCGCTGAAACCCATCCCTCTCTGAGCTGGTCTACTTGCAAATCGGGTGGTAGCTGCACC
ACAAACTCCGGTGCCATTACGTTAGATGCCAACTGGCGTTGGGTCCATGGTGTCAATACCAGCACCAACTGCTACA
CTGGCAACACTTGGAATAGCGCCATCTGCGACACTGATGCATCCTGTGCCCAGGACTGTGCTCTCGATGGTGCTGA
CTACTCTGGCACGTACGGTATCACTACCTCCGGCAACTCATTGCGCCTGAACTTCGTTACCGGTTCCAACGTCGGAT
CTCGTACTTACCTGATGGCCGATAACACCCACTACCAAATCTTCGATCTGTTGAACCAGGAGTTCACCTTCACCGTC
GATGTCTCCCACCTCCCTTGCGGTTTGAACGGTGCCCTCTACTTCGTGACCATGGATGCCGACGGTGGCGTCTCCA
AGTACCCCAACAACAAGGCCGGTGCTCAGTACGGTGTTGGATACTGTGACTCTCAATGCCCTCGTGACTTGAAGTT
CATCGCTGGTCAGGCCAACGTTGAGGGCTGGACGCCCTCCGCCAACAACGCCAACACTGGAATTGGCAATCACGG
AGCTTGCTGCGCGGAGCTTGATATCTGGGAGGCAAACAGCATCTCAGAGGCCTTGACTCCTCACCCTTGCGATACA
CCCGGTCTATCTGTTTGCACTACTGATGCCTGCGGTGGTACCTACAGCTCTGATCGTTACGCCGGTACCTGCGACCC
TGATGGATGTGACTTCAACCCTTACCGCCTTGGTGTCACTGACTTCTACGGCTCCGGCAAGACCGTTGACACCACC
AAGCCCTTTACCGTTGTGACTCAATTCGTCACTAACGACGGTACCTCCACCGGTTCCCTCTCCGAGATCAGACGTTA
CTACGTTCAGAACGGCGTTGTCATCCCCCAGCCTTCCTCCAAGATCTCCGGAATCAGCGGAAATGTCATCAACTCC
GACTACTGCGCTGCTGAAATTTCCACCTTTGGCGGGACTGCCTCCTTCAGCAAACACGGTGGCTTGACAAACATGG
CCGCTGGTATGGAAGCTGGTATGGTCTTGGTCATGAGTTTGTGGGACGACTACGCCGTCAACATGCTCTGGCTCG
ACAGCACCTACCCTACAAACGCGACTGGTACCCCGGTGCCGCTCGTGGTACCTGCGCTACCACTTCTGGGGACCC
CAAGACCGTTGAATCACAATCCGGCAGCTCCTATGTCACCTTCTCTGACATTCGGGTTGGTCCTTTCAATTCTACGTT
CAGCGGTGGTTCTAGCACCGGTGGCAGCACTACTACTACCGCCAGCCGCACCACCACCACCTCGGCCTCTTCCACC
TCTACTTCCAGCACCTCTACTGGCACTGGAGGATCCGGCGCTGCAAGCTCAAGCTCGTCCACGCGCGCCGCGTCGA
CGACTTCTCGAGTATCCCCCACAACATCCCGGTCGAGCTCCGCGACGCCTCCACCTGGTTCTACTACTACCAGAGTA
CCTCCAGTCGGATCGGGAAAGCTGGCTGGCGGCGGCTACTGGCACACCTCCGGTCGCGAGATACTCGACGCAAAT
AATGTTCCTGTCCGAATCGCGGGGATTAACTGGTTCGGATTCGAGACGTGCAATTACGTTGTCCATGGCCTTTGGT
CCCGAGATTACCGCTCAATGCTCGACCAGATCAAGTCGCTCGGTTACAACACGATTCGTCTACCGTATTCTGACGA
CATCCTTAAGCCCGGCACCATGCCAAATAGCATCAATTTTTACCAAATGAACCAAGACCTGCAGGGGCTTACTTCCC
TGCAGGTGATGGACAAGATCGTTGCCTACGCCGGCCAGATCGGACTGCGTATCATCCTGGACCGCCACCGGCCGG
ACTGCAGCGGCCAGTCGGCCTTGTGGTACACGAGCAGCGTTTCGGAGGCCACATGGATTTCCGACCTGCAGGCTT
TGGCCCAGCGCTACAAGGGAAACCCAACTGTCGTAGGCTTCGACCTCCACAACGAGCCCCACGACCCCGCATGCT
GGGGATGCGGCGATCCGTCGATTGACTGGAGGCTCGCTGCCGAACGTGCTGGTAACGCTGTCTTGTCCGTGAACC
CAAACCTTCTGATCTTCGTCGAAGGCGTTCAGTCTTACAATGGAGATTCGTACTGGTGGGCGGAAACCTTCAGGG
CGCTGGCCAATACCCGGTCGTTCTCAACGTTCCGAACCGGCTTGTTTACAGCGCACACGACTACGCCACGAGCGTC
GGCCCTCAAACCTGGTTCTCCGACCCTACATTCCCCAACAACATGCCAGGAATCTGGAACAAGAATTGGGGCTACC
TTTTCAACCAGAACATCGCTCCCGTTTGGCTGGGCGAGTTTGGCACAACGTTGCAGTCTACGACGGACCAAACATG
GCTGAAGACCCTCGTCCAGTATCTCAGGCCCACCGCGCAGTATGGTGCGGACAGCTTTCAGTGGACCTTCTGGTCT
TGGAACCCCGATTCTGGCGACACAGGCGGTATCCTGAAGGATGATTGGCAGACGGTTGACACAGTCAAGGACGG
TTATCTGGCACCTATCAAGTCCAGCATCTTCGACCCCGTTTAA

FIGURE 25B

HC10-2Link-E1 (Protein sequence)

MSALNSFNMYKSALILGSLLATAGAQQIGTYTAETHPSLSWSTCKSGGSCTTNSGAITLDANWRWVHGVNTSTNCYTG
NTWNSAICDTDASCAQDCALDGADYSGTYGITTSGNSLRLNFVTGSNVGSRTYLMADNTHYQIFDLLNQEFTFTVDVS
HLPCGLNGALYFVTMDADGGVSKYPNNKAGAQYGVGYCDSQCPRDLKFIAGQANVEGWTPSANNANTGIGNHGAC
CAELDIWEANSISEALTPHPCDTPGLSVCTTDACGGTYSSDRYAGTCDPDGCDFNPYRLGVTDFYGSGKTVDTTKPFTV
VTQFVTNDGTSTGSLSEIRRYYVQNGVVIPQPSSKISGISGNVINSDYCAAEISTFGGTASFSKHGGLTNMAAGMEAGM
VLVMSLWDDYAVNMLWLDSTYPTNATGTPGAARGTCATTSGDPKTVESQSGSSYVTFSDIRVGPFNSTFSGGSSTGG
STTTTASRTTTTSASSTSTSSTSTGTGGSGAASSSSSTRAASTTSRVSPTTSRSSSATPPPGSTTTRVPPVGSGKLAGGGYW
HTSGREILDANNVPVRIAGINWFGFETCNYVVHGLWSRDYRSMLDQIKSLGYNTIRLPYSDDILKPGTMPNSINFYQMN
QDLQGLTSLQVMDKIVAYAGQIGLRIILDRHRPDCSGQSALWYTSSVSEATWISDLQALAQRYKGNPTVVGFDLHNEP
HDPACWGCGDPSIDWRLAAERAGNAVLSVNPNLLIFVEGVQSYNGDSYWWGGNLQGAGQYPVVLNVPNRLVYSAH
DYATSVGPQTWFSDPTFPNNMPGIWNKNWGYLFNQNIAPVWLGEFGTTLQSTTDQTWLKTLVQYLRPTAQYGADS
FQWTFWSWNPDSGDTGGILKDDWQTVDTVKDGYLAPIKSSIFDPV

FIGURE 26A

HC10-CBM3-E1 (cDNA sequence)

ATGTCTGCCTTGAACTCTTTCAATATGTACAAGAGCGCCCTCATCTTGGGCTCCTTGCTGGCAACAGCTGGTGCTCA
GCAAATTGGTACTTATACCGCTGAAACCCATCCCTCTCTGAGCTGGTCTACTTGCAAATCGGGTGGTAGCTGCACC
ACAAACTCCGGTGCCATTACGTTAGATGCCAACTGGCGTTGGGTCCATGGTGTCAATACCAGCACCAACTGCTACA
CTGGCAACACTTGGAATAGCGCCATCTGCGACACTGATGCATCCTGTGCCCAGGACTGTGCTCTCGATGGTGCTGA
CTACTCTGGCACGTACGGTATCACTACCTCCGGCAACTCATTGCGCCTGAACTTCGTTACCGGTTCCAACGTCGGAT
CTCGTACTTACCTGATGGCCGATAACACCCACTACCAAATCTTCGATCTGTTGAACCAGGAGTTCACCTTCACCGTC
GATGTCTCCCACCTCCCTTGCGGTTTGAACGGTGCCCTCTACTTCGTGACCATGGATGCCGACGGTGGCGTCTCCA
AGTACCCCAACAACAAGGCCGGTGCTCAGTACGGTGTTGGATACTGTGACTCTCAATGCCCTCGTGACTTGAAGTT
CATCGCTGGTCAGGCCAACGTTGAGGGCTGGACGCCCTCCGCCAACAACGCCAACACTGGAATTGGCAATCACGG
AGCTTGCTGCGCGGAGCTTGATATCTGGGAGGCAAACAGCATCTCAGAGGCCTTGACTCCTCACCCTTGCGATACA
CCCGGTCTATCTGTTTGCACTACTGATGCCTGCGGTGGTACCTACAGCTCTGATCGTTACGCCGGTACCTGCGACCC
TGATGGATGTGACTTCAACCCTTACCGCCTTGGTGTCACTGACTTCTACGGCTCCGGCAAGACCGTTGACACCACC
AAGCCCTTTACCGTTGTGACTCAATTCGTCACTAACGACGGTACCTCCACCGGTTCCCTCTCCGAGATCAGACGTTA
CTACGTTCAGAACGGCGTTGTCATCCCCCAGCCTTCCTCCAAGATCTCCGGAATCAGCGGAAATGTCATCAACTCC
GACTACTGCGCTGCTGAAATTTCCACCTTTGGCGGGACTGCCTCCTTCAGCAAACACGGTGGCTTGACAAACATGG
CCGCTGGTATGGAAGCTGGTATGGTCTTGGTCATGAGTTTGTGGGACGACTACGCCGTCAACATGCTCTGGCTCG
ACAGCACCTACCCTACAAACGCGACTGGTACCCCGGTGCCGCTCGTGGTACCTGCGCTACCACTTCTGGGGACCC
CAAGACCGTTGAATCACAATCCGGCAGCTCCTATGTCACCTTCTCTGACATTCGGGTTGGTCCTTTCAATTCTACGTT
CAGCGGTGGTTCTAGCACCGGTGGCAGCACTACTACTACCGCCAGCCGCACCACCACCACCTCGGCCTCTTCCACC
TCTACTTCCAGCACCTCTACTGGCACTGGAGGATCCGTTGCAGGTGGACAGATTAAAGTGCTCTATGCAAATAAGG
AAACCAATTCAACAACGAACACGATTCGCCCGTGGCTGAAAGTCGTGAATACGGGGTCCAGTTCAATCGATCTCTC
CCGCGTCACTATCCGCTACTGGTACACCGTAGATGGCGATAAAGCACAATCCGCAATTTCGGATTGGGCCCAGATC
GGTGCTAGCAACGTAACTTTTAAATTTGTCAAGCTGAGTAGCTCGGTTAGTGGGGCCGACTATTATCTGGAGATCG
GTTTCAAAAGTGGAGCCGGCCAGCTCCAGGCCGGTAAAGACACGGGAGAAATACAGATCCGCTTTAATAAATCCG
ACTGGAGCAATTATAACCAGGGGAACGATTGGAGCTGGATGCAATCCATGACCTCTTACGGTGAAAATGTAAAGG
TCACCGCATATATAGATGGCGTACTCGTCTGGGGCCAAGAACCTTCCGGAGCGGGCGCTGCAAGCTCAAGCTCGT
CCACGCGCGCCGCGTCGACGACTTCTCGAGTATCCCCCACAACATCCCGGTCGAGCTCCGCGACGCCTCCACCTGG
TTCTACTACTACCAGAGTACCTCCAGTCGGATCGGGAAAGCTGGCTGGCGGCGGCTACTGGCACACCTCCGGTCG
CGAGATACTCGACGCAAATAATGTTCCTGTCCGAATCGCGGGGATTAACTGGTTCGGATTCGAGACGTGCAATTAC
GTTGTCCATGGCCTTTGGTCCCGAGATTACCGCTCAATGCTCGACCAGATCAAGTCGCTCGGTTACAACACGATTC
GTCTACCGTATTCTGACGACATCCTTAAGCCCGGCACCATGCCAAATAGCATCAATTTTTACCAAATGAACCAAGAC
CTGCAGGGGCTTACTTCCCTGCAGGTGATGGACAAGATCGTTGCCTACGCCGGCCAGATCGGACTGCGTATCATCC
TGGACCGCCACCGGCCGGACTGCAGCGGCCAGTCGGCCTTGTGGTACACGAGCAGCGTTTCGGAGGCCACATGG
ATTTCCGACCTGCAGGCTTTGGCCCAGCGCTACAAGGGAAACCCAACTGTCGTAGGCTTCGACCTCCACAACGAGC
CCACGACCCCGCATGCTGGGGATGCGGCGATCCGTCGATTGACTGGAGGCTCGCTGCCGAACGTGCTGGTAACG
CTGTCTTGTCCGTGAACCCAAACCTTCTGATCTTCGTCGAAGGCGTTCAGTCTTACAATGGAGATTCGTACTGGTGG
GGCGGAAACCTTCAGGGCGCTGGCCAATACCCGGTCGTTCTCAACGTTCCGAACCGGCTTGTTTACAGCGCACAC
GACTACGCCACGAGCGTCGGCCCTCAAACCTGGTTCTCCGACCCTACATTCCCCAACAACATGCCAGGAATCTGGA
ACAAGAATTGGGGCTACCTTTTCAACCAGAACATCGCTCCCGTTTGGCTGGGCGAGTTTGGCACAACGTTGCAGTC
TACGACGGACCAAACATGGCTGAAGACCCTCGTCCAGTATCTCAGGCCCACCGCGCAGTATGGTGCGGACAGCTT
TCAGTGGACCTTCTGGTCTTGGAACCCCGATTCTGGCGACACAGGCGGTATCCTGAAGGATGATTGGCAGACGGT
TGACACAGTCAAGGACGGTTATCTGGCACCTATCAAGTCCAGCATCTTCGACCCCGTTTAA

FIGURE 26B

HC10-CBM3-E1 (Protein sequence)

MSALNSFNMYKSALILGSLLATAGAQQIGTYTAETHPSLSWSTCKSGGSCTTNSGAITLDANWRWVHGVNTSTNCYTG
NTWNSAICDTDASCAQDCALDGADYSGTYGITTSGNSLRLNFVTGSNVGSRTYLMADNTHYQIFDLLNQEFTFTVDVS
HLPCGLNGALYFVTMDADGGVSKYPNNKAGAQYGVGYCDSQCPRDLKFIAGQANVEGWTPSANNANTGIGNHGAC
CAELDIWEANSISEALTPHPCDTPGLSVCTTDACGGTYSSDRYAGTCDPDGCDFNPYRLGVTDFYGSGKTVDTTKPFTV
VTQFVTNDGTSTGSLSEIRRYYVQNGVVIPQPSSKISGISGNVINSDYCAAEISTFGGTASFSKHGGLTNMAAGMEAGM
VLVMSLWDDYAVNMLWLDSTYPTNATGTPGAARGTCATTSGDPKTVESQSGSSYVTFSDIRVGPFNSTFSGGSSTGG
STTTTASRTTTTSASSTSTSSTSTGTGGSVAGGQIKVLYANKETNSTTNTIRPWLKVVNTGSSSIDLSRVTIRYWYTVDGD
KAQSAISDWAQIGASNVTFKFVKLSSSVSGADYYLEIGFKSGAGQLQAGKDTGEIQIRFNKSDWSNYNQGNDWSWM
QSMTSYGENVKVTAYIDGVLVWGQEPSGAGAASSSSSTRAASTTSRVSPTTSRSSSATPPPGSTTTRVPPVGSGKLAGG
GYWHTSGREILDANNVPVRIAGINWFGFETCNYVVHGLWSRDYRSMLDQIKSLGYNTIRLPYSDDILKPGTMPNSINFY
QMNQDLQGLTSLQVMDKIVAYAGQIGLRIILDRHRPDCSGQSALWYTSSVSEATWISDLQALAQRYKGNPTVVGFDL
HNEPHDPACWGCGDPSIDWRLAAERAGNAVLSVNPNLLIFVEGVQSYNGDSYWWGGNLQGAGQYPVVLNVPNRL
VYSAHDYATSVGPQTWFSDPTFPNNMPGIWNKNWGYLFNQNIAPVWLGEFGTTLQSTTDQTWLKTLVQYLRPTAQ
YGADSFQWTFWSWNPDSGDTGGILKDDWQTVDTVKDGYLAPIKSSIFDPV

MULTIFUNCTIONAL MICROBIAL CELLULASES

CROSS-REFERENCE TO RELATED APPLICATION

This application claims priority from U.S. Provisional Application No. 62/467,674, filed Mar. 6, 2017, the disclosure of which is incorporated herein by reference in its entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

BACKGROUND

Enzymatic conversion of biomass to glucose and xylose is typically performed using a thermochemical pretreatment step followed by a saccharification step utilizing mixtures of mesophilic enzymes derived from fungi such as *Trichoderma reesei*. Both of these process steps have significant costs associated with them. Family 7 cellobiohydrolases (CBHs), such as Cel7A from *T. reesei*, are considered to be the most important enzymes for biomass conversion. Production of these enzymes represents a substantial portion of costs associated with biorefinery operations. Development of enzymes with increased activity or functionality can significantly impact the economics of the bioconversion process.

The foregoing examples of the related art and limitations related therewith are intended to be illustrative and not exclusive. Other limitations of the related art will become apparent to those of skill in the art upon a reading of the specification and a study of the drawings.

SUMMARY

In an aspect, disclosed is a non-naturally occurring multifunctional enzyme having greater than 60% identity to SEQ ID NO: 6. In an embodiment, disclosed is an isolated nucleic acid encoding a multifunctional enzyme and having greater than 70% identity to SEQ ID NO: 5. In another embodiment, the isolated nucleic acid molecule has a promoter operably linked to the nucleic acid molecule. In another embodiment, the isolated nucleic acid molecule has a promoter that allows expression of the nucleic acid in a filamentous fungal host cell. In an embodiment, an expression vector is disclosed that has a nucleic acid molecule of having greater than 70% identity to SEQ ID NO: 5. In an embodiment, disclosed is a host cell having an expression expressing a recombinant polypeptide encoded by a nucleic acid molecule having greater than 70% identity to SEQ ID NO: 5. In another embodiment, the host cell is a fungal cell. In an embodiment, an isolated multifunctional enzyme polypeptide is disclosed that is encoded by the nucleic acid molecule having greater than 70% identity to SEQ ID NO: 5.

In an aspect, a method is disclosed for degrading cellulose or lignocellulosic biomass, comprising contacting the cellulose or lignocellulosic biomass with a multifunctional enzyme having greater than 60% identity to SEQ ID NO: 6. In an embodiment, the cellulose is degraded by the multifunctional enzyme in about 50% of the time that it takes the isolated enzymes that comprise the multifunctional enzyme to degrade the cellulose.

In another aspect, a method for producing a biofuel from lignocellulosic biomass is disclosed that includes the steps of contacting the lignocellulosic biomass with a multifunctional enzyme having greater than 60% identity to SEQ ID NO: 6 to generate sugars; and converting the sugars to a biofuel by fermentation.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 1 shows the nucleotide (A) and amino acid (B) sequences of an exemplary multifunctional enzyme containing the catalytic domain from *P. funiculosum* Ce17 (underlined), the linker from *P. funiculosum* Ce17 (bold), and the catalytic domain from *A. cellulolyticus* E1 (double underlined).

FIG. 2 shows the nucleotide (A) and amino acid (B) sequences of an exemplary multifunctional enzyme containing the catalytic domain from *P. funiculosum* Ce17 (underlined), the linker from *P. funiculosum* Ce17 (bold), the linker from *T. reesei* Cel6A (bold and underlined), and the catalytic domain from *A. cellulolyticus* E1 (double underlined).

FIG. 3 shows the nucleotide (A) and amino acid (B) sequences of an exemplary multifunctional enzyme containing the catalytic domain from *P. funiculosum* Ce17 (underlined), the linker from *P. funiculosum* Ce17 (bold), the CBM3 domain from *C. bescii* (dotted underline), the linker from *T. reesei* Cel6A (bold and underlined), and the catalytic domain from *A. cellulolyticus* E1 (double underlined).

FIG. 4 shows the nucleotide (A) and amino acid (B) sequences of an exemplary multifunctional enzyme containing the catalytic domain from *T. reesei* CBH1 (underlined), the linker from *P. funiculosum* Ce17 (bold), and the catalytic domain from *A. cellulolyticus* E1 (double underlined).

FIG. 5 shows the nucleotide (A) and amino acid (B) sequences of an exemplary multifunctional enzyme containing the catalytic domain from *P. funiculosum* Ce17 (underlined), the linker from *P. funiculosum* Ce17 (bold), the linker from *T. reesei* Cel6A (bold and underlined), the GH9 domain from *C. phytofermentans* (double underlined; comprising a fusion of the GH9 domain, a short linker and the CBM3 domain).

FIG. 6 shows the nucleotide (A) and amino acid (B) sequences of an exemplary multifunctional enzyme containing the catalytic domain from *P. funiculosum* Ce17 (underlined), the linker from *P. funiculosum* Ce17 (bold), the CBM1 domain from *P. funiculosum* Ce17 (dotted underline), the linker from *T. reesei* Cel6A (bold and underlined), and the catalytic domain from *A. cellulolyticus* E1 (double underlined).

Figure 12:
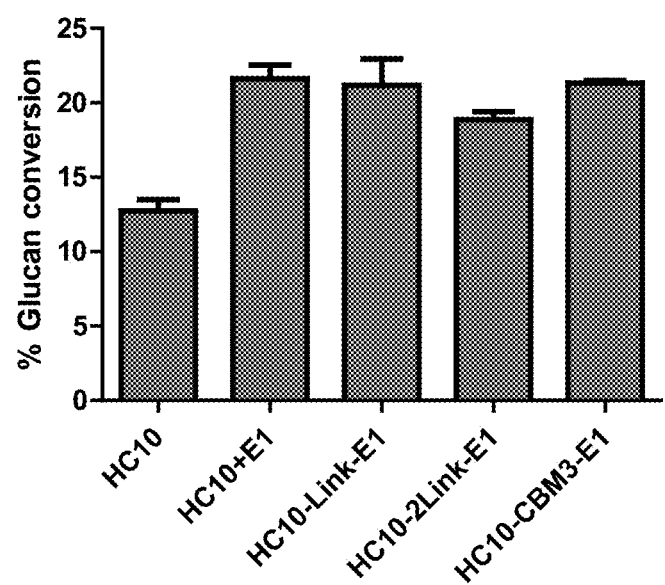

FIG. 12 shows the results of five day enzyme digestion of Avicel at high solids compared on an active site basis.

Figure 13:
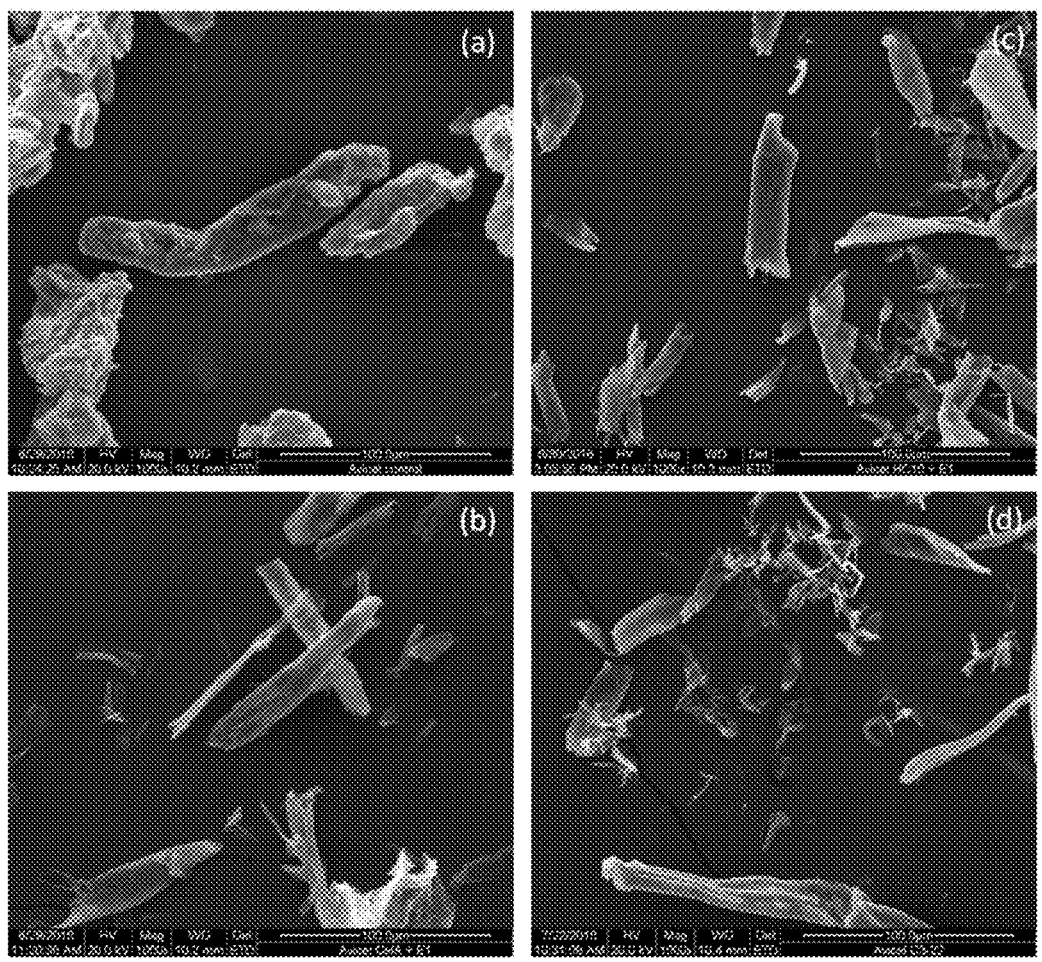

FIG. 13 shows low magnification SEM micrographs (1000×) of three enzymatic digestions of Avicel PH101 as compared to an Avicel control illustrating the resultant post reaction particle distribution. (a) Control (b) Cel A+E1 (c) HC10+E1 (d) HC10-CBM3-E1.

Figure 14:
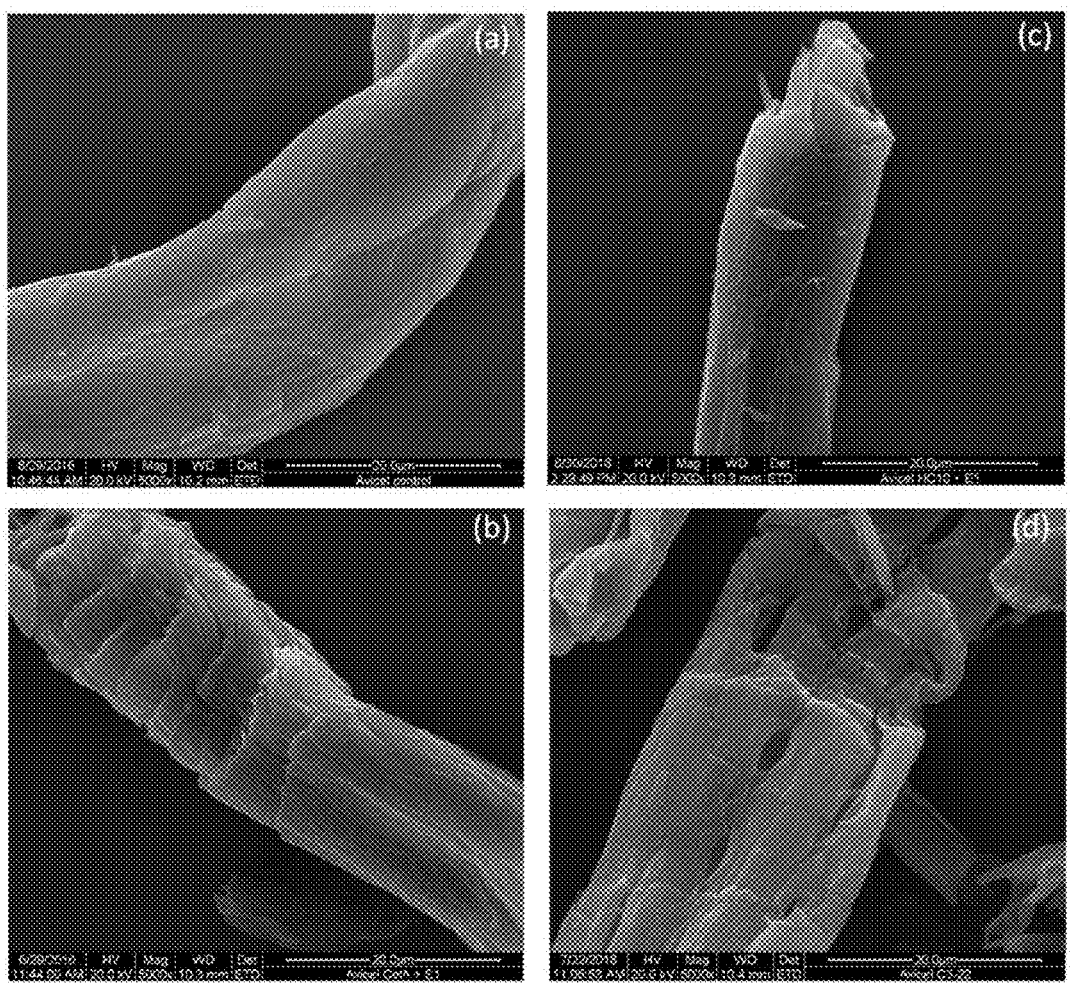

FIG. 14 shows 5000× magnification SEM micrographs of three enzymatic digestions of Avicel as compared to an Avicel control illustrates potential different enzymatic mechanisms. (a) Control (b) Cel A+E1 (c) HC10+E1 (d) HC10-CBM3-E1.

Figure 15:
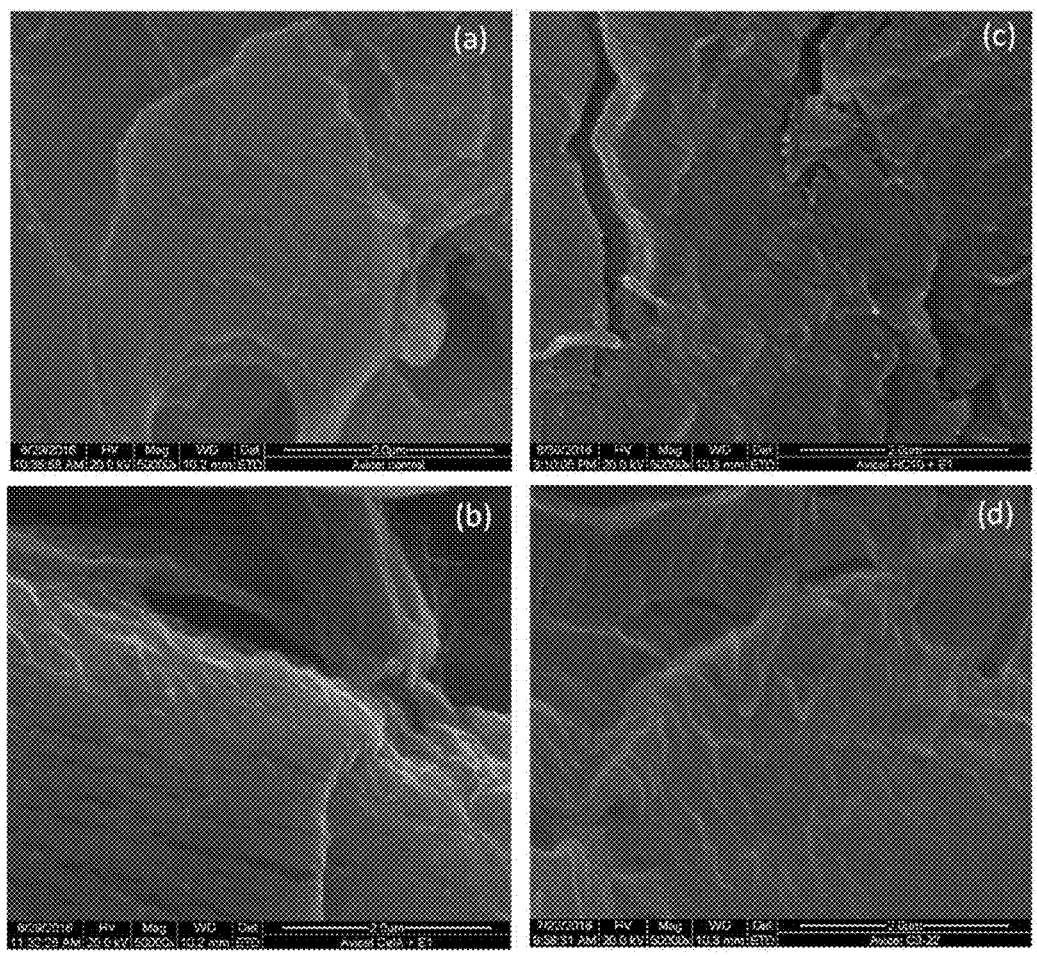

FIG. 15 shows 50,000× magnification SEM micrographs of three enzymatic digestions of Avicel as compared to an Avicel control, illustrating potential differences in enzymatic mechanisms and severities of micro-erosion patterns. (a) Control (b) Cel A+E1 (c) HC10+E1 (d) HC10-CBM3-E1.

Figure 16:
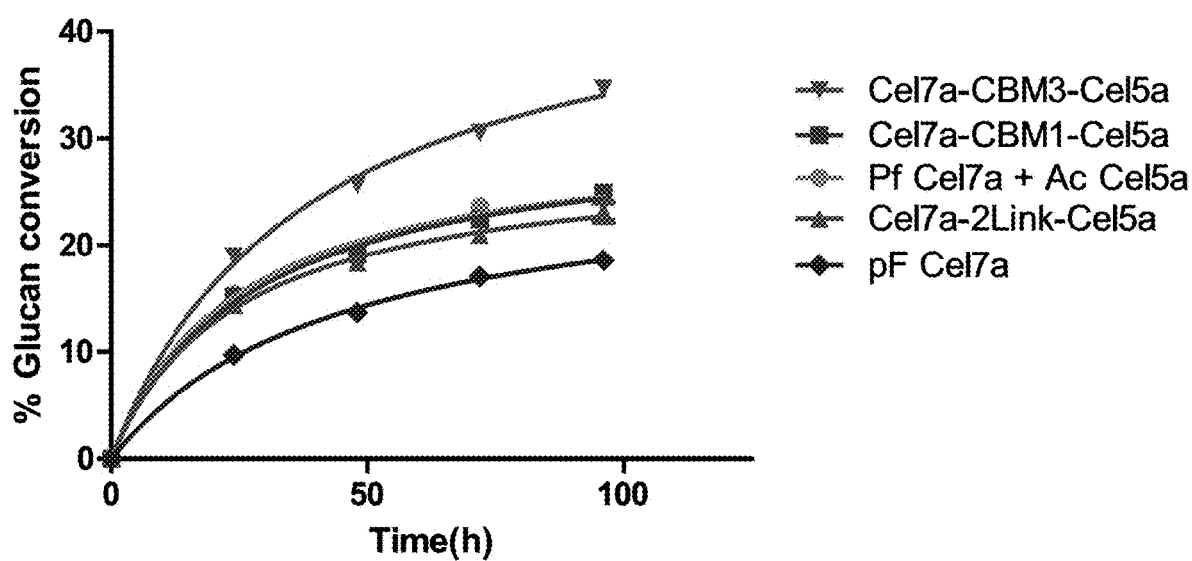

FIG. 16 depicts the percent conversion of Avicel for linked and free enzyme constructs.

Figure 17:
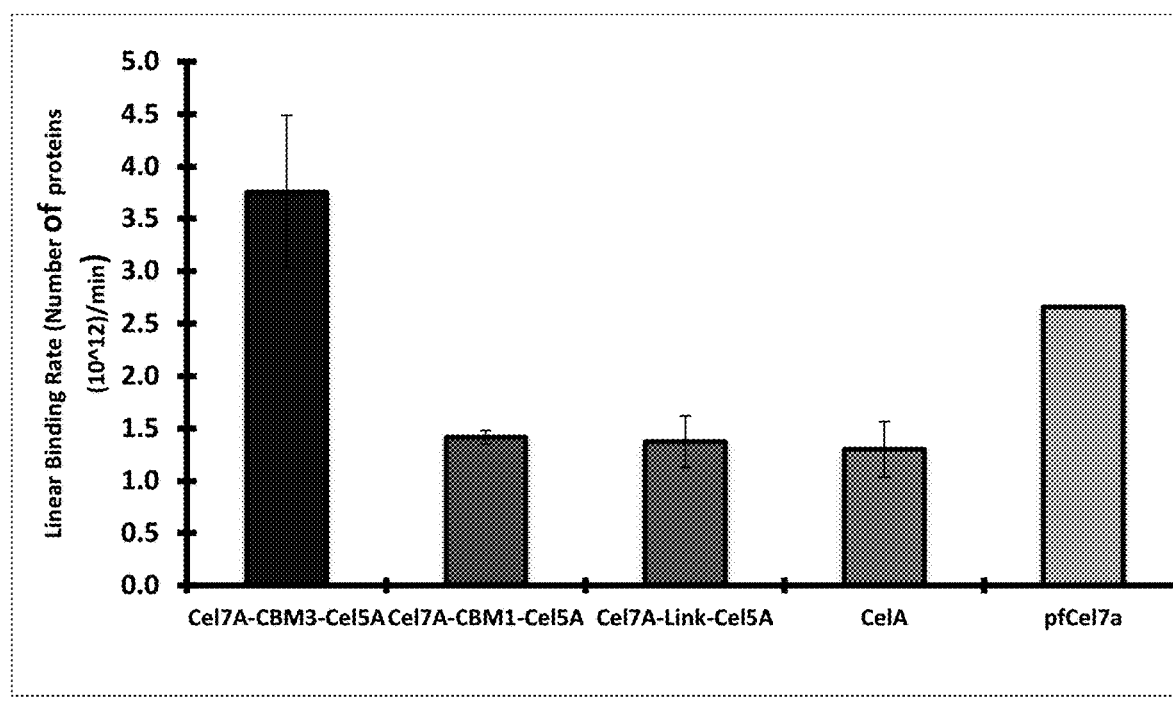

FIG. 17 depicts the linear binding rate for linked and free enzyme constructs using QCM-D.

Figure 18:
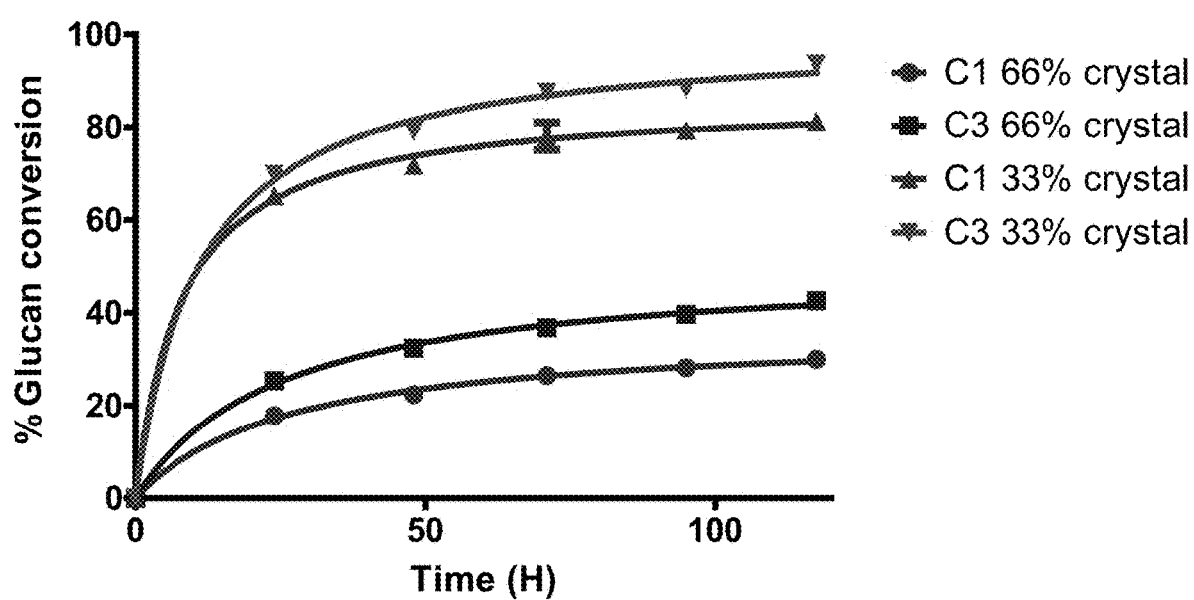

FIG. 18 depicts the percent glucan conversion of equal active site basis loading of Cel7a-CBM1-Cel5a and Cel7a-CBM3-Cel5a on differential crystallinity substrates.

Figure 19:
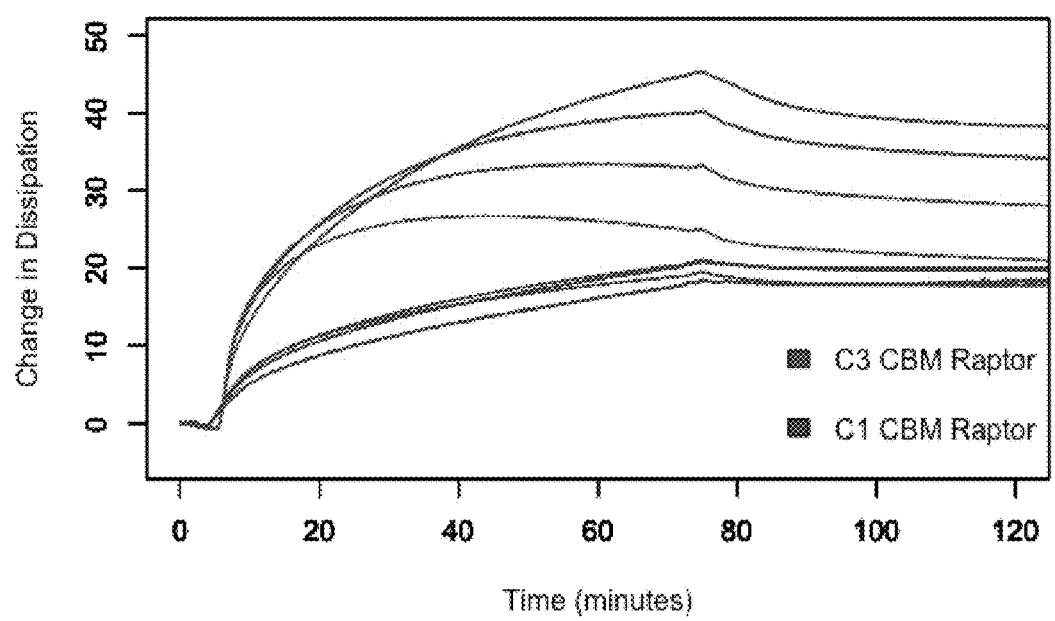

FIG. 19 depicts QCMD changes in dissipation for C3 and C1 constructs to a cellulose substrate in the presence of 10 mM cellobiose to inhibit cellulase action.

Figure 20:
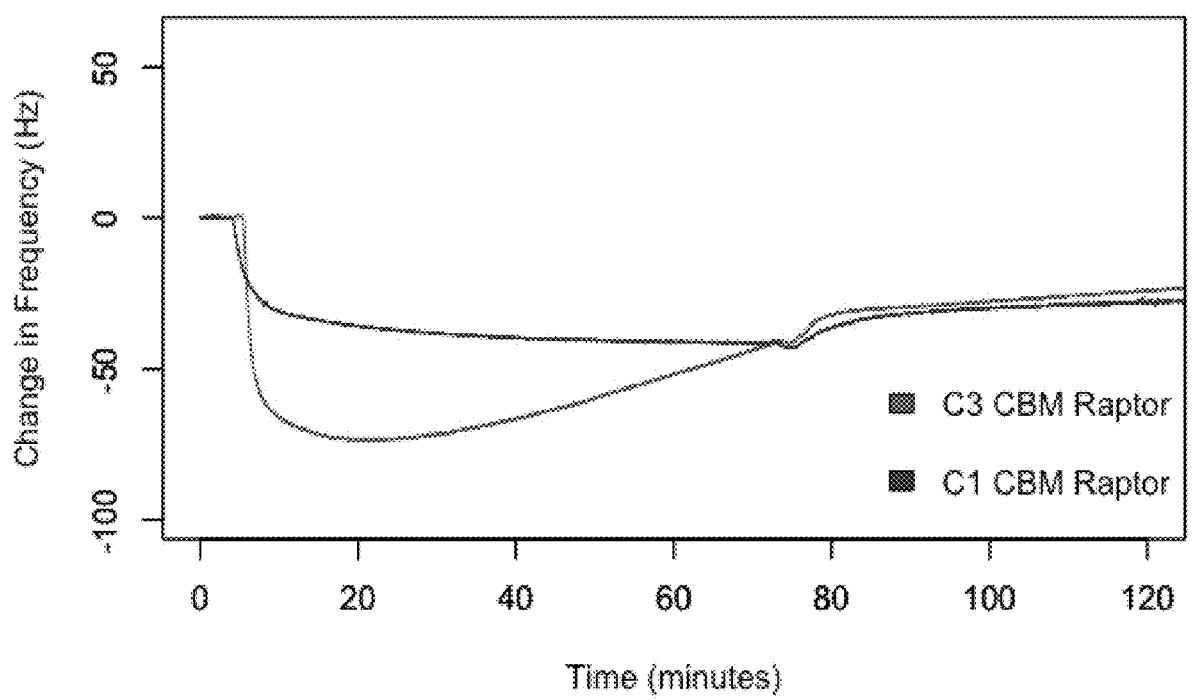

FIG. 20 depicts QCMD changes in frequency for C3 and C1 constructs to a cellulose substrate in the presence of 10 mM cellobiose to inhibit cellulase action.

FIG. 21 depicts TEM images for C1, C2 and C3 digestions.

Figure 22:
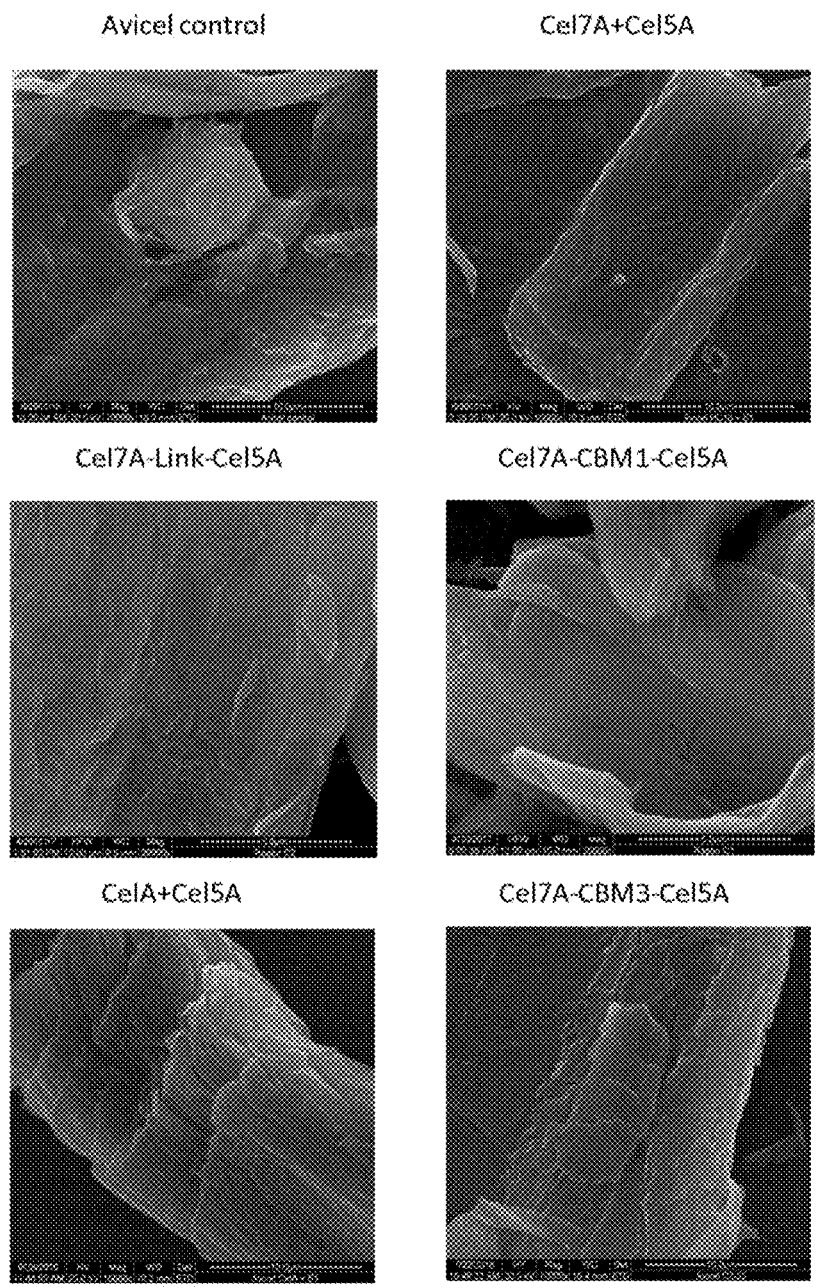

FIG. 22 depicts SEM images for C1, C2 and C3 and other construct digestions.

Figure 23:
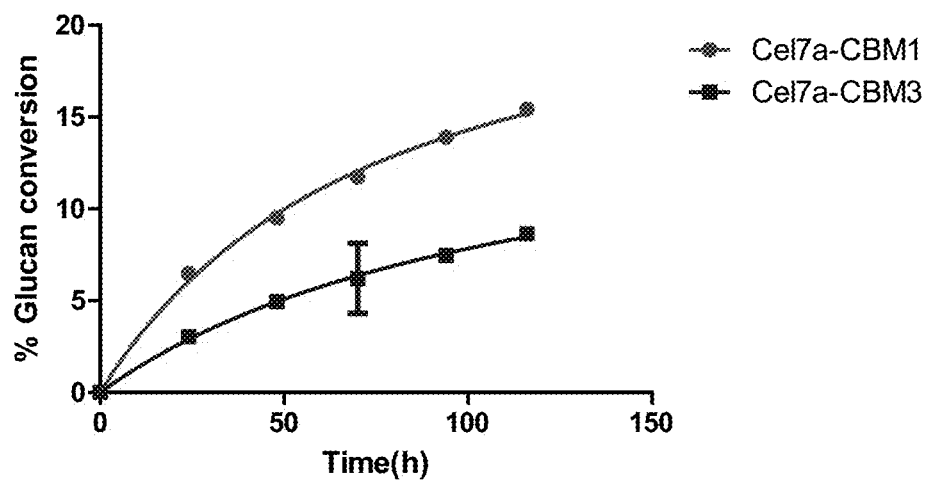

FIG. 23 depicts percent glucan conversion over time of a native Cel7a with its native CBM1 compared to the synthetic Cel7a-CBM3 construct at equal enzyme loading.

FIG. 24A depicts the cDNA sequence of C1 (SEQ ID NO: 1), also referred to as HC10-CBM1-E1. FIG. 24B depicts the amino acid sequence of C1 (SEQ ID NO: 2), also referred to as HC10-CBM1-E1.

FIG. 25A depicts the cDNA sequence of C2 (SEQ ID NO: 3), also referred to as HC10-2Link-E1. FIG. 25B depicts the amino acid sequence of C2 (SEQ ID NO: 4), also referred to as HC10-2Link-E1.

FIG. 26A depicts the cDNA sequence of C3 (SEQ ID NO: 5), also referred to as HC10-CBM3-E1. FIG. 26B depicts the amino acid sequence of C3 (SEQ ID NO: 6), also referred to as HC10-CBM3-E1.

Figure 27:
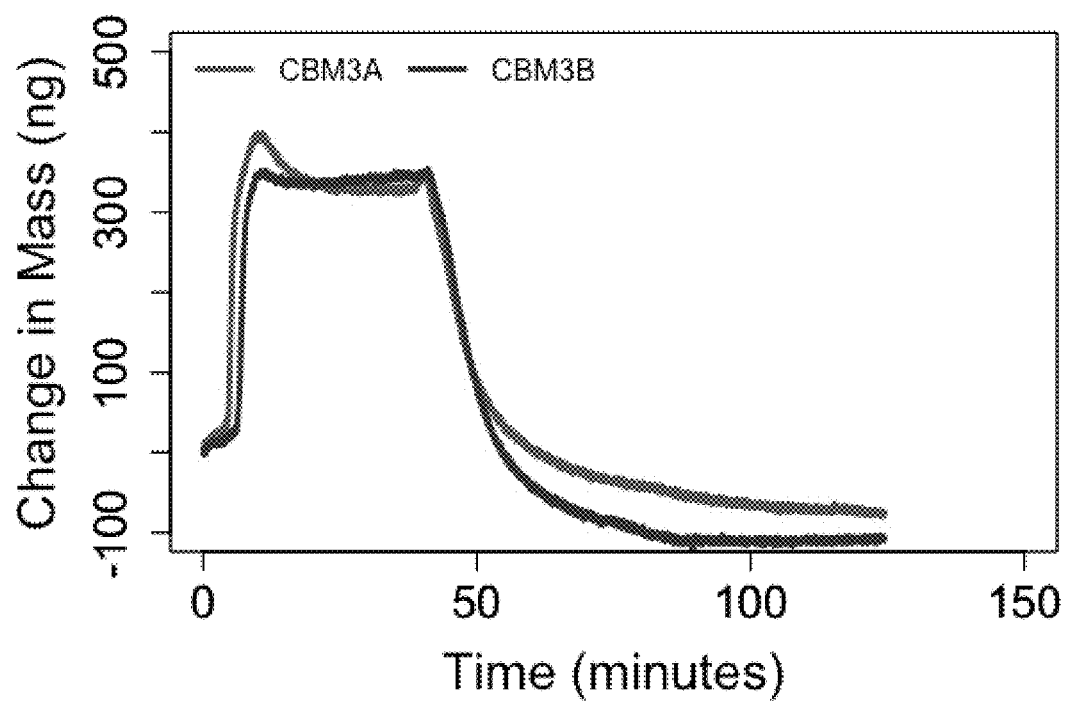

FIG. 27 depicts change in mass QCM data of CBM3 molecules.

Figure 28:
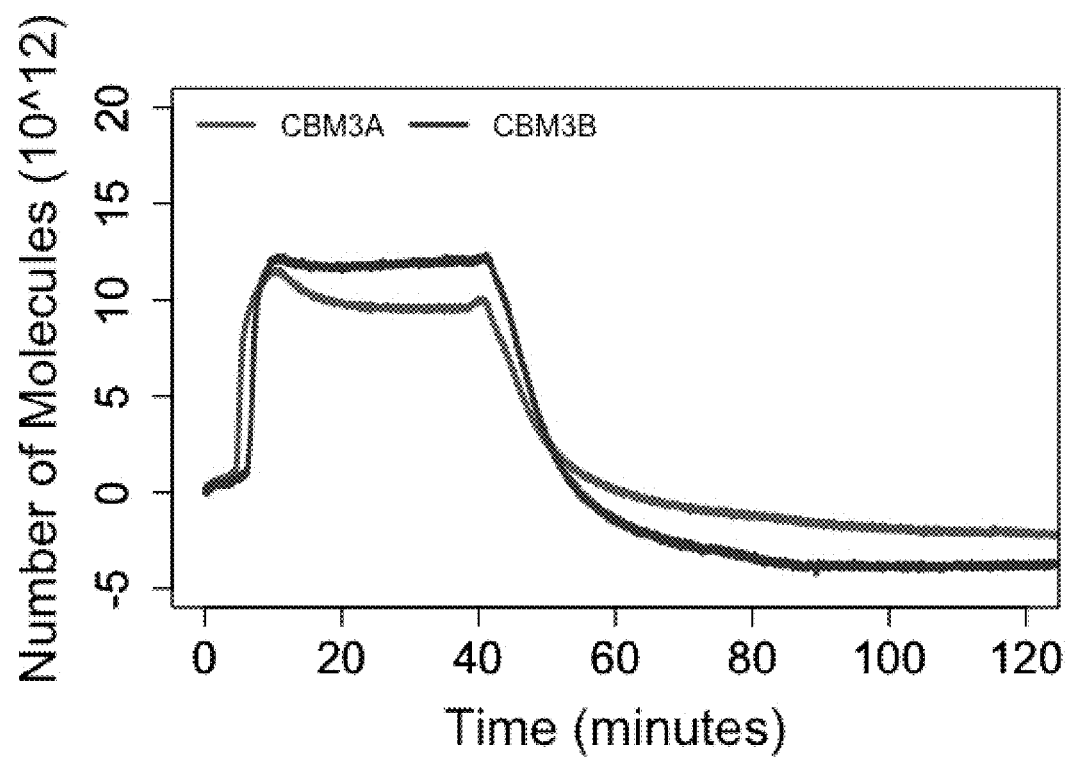

FIG. 28 depicts QCM data in the form of the change in the number of CBM3 molecules.

Figure 29:
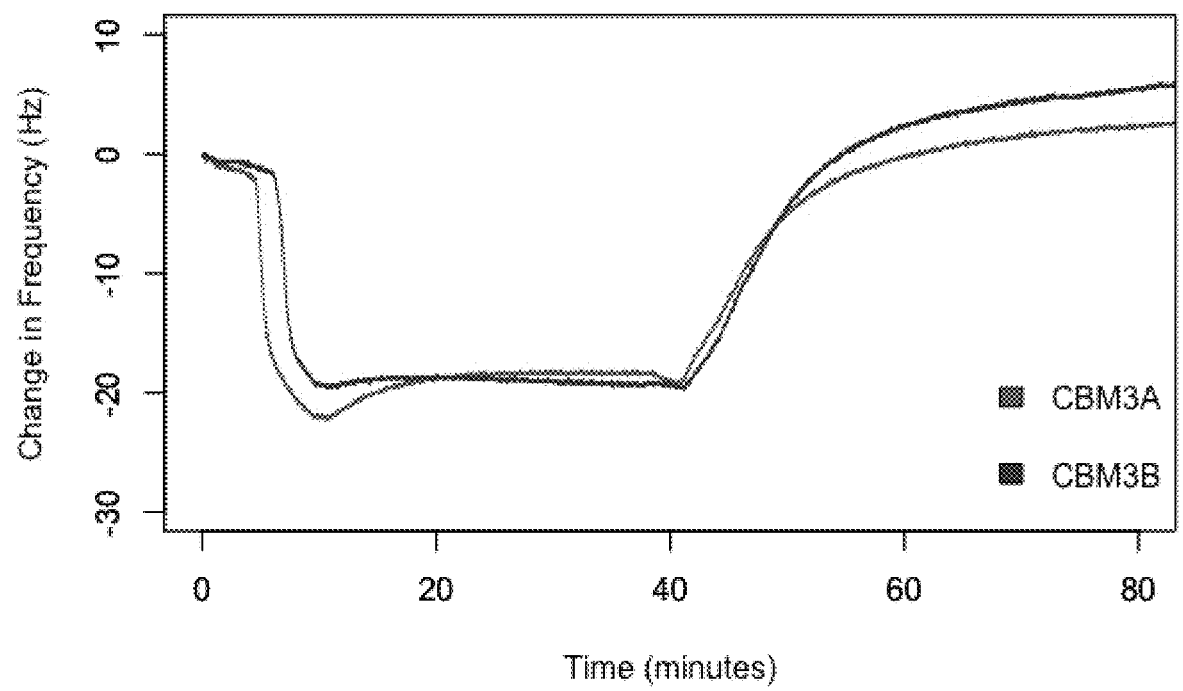

FIG. 29 depicts QCM data in the form of the change in frequency of CBM3 molecules.

DETAILED DESCRIPTION

Disclosed herein are engineered multifunctional enzymes that contain unique combinations of domains useful in the enzymatic conversion of biomass. The domain combinations are not found in native microbial cellulases, and the multifunctional enzymes encompassing the domain combinations exhibit enhanced cellulolytic activity on cellulose-containing substrates. In addition to outperforming native enzymes, the multifunctional enzymes can be expressed as one recombinant construct, eliminating the need for the production of multiple components of an enzyme cocktail for biomass conversion.

Enzymatic conversion of biomass to glucose and xylose is currently performed using a thermochemical pretreatment followed by a saccharification step utilizing mixtures of mesophilic enzymes derived from fungi such as *T. reesei*. Both of these process steps have significant costs associated with them. By utilizing an improved multifunctional Cel7A-based cellulase system, especially if in doing so a minimal gene set can be used to transform the host, the costs of both of these process steps can be reduced. In addition to showing improved performance over a native organism enzyme mix, the use of a single enzyme (versus two or more) is beneficial from a production as well as genetic engineering standpoint, both of which can significantly impact the economics of the bioconversion process.

The methods disclosed herein may be used to produce multifunctional enzymes in fungal host system, easing the need for heterologous enzyme expression in fungi such as *T. reesei* that has historically been difficult. The methods and constructs also allow the bulk properties such as extent of cellulose binding of multifunctional enzymes to be varied by their modular composition. The overall performance of multifunctional enzymes may also be tailored and improved by altering their domain architecture (for example, specifically tailoring enzymes to work on highly crystalline substrates). The meso-scale deconstruction mechanism of cellulose may also be altered by utilizing different combinations of catalytic domains as well as carbohydrate binding modules.

Fungi and bacteria utilize distinct mechanisms for cellulose deconstruction: the fungal free enzyme model exemplified by the GH family 7 CBH1 fungal exo-cellulase and an alternative multifunctional enzyme system exemplified by CelA from the hyperthermophilic bacterium *C. bescii*. CelA is a multifunctional multimodular enzyme, its architecture is designated as a GH9-CBM3-CBM3-CBM3-GH48. The GH9 module is an endo cellulase, while the GH48 module is an exo-cellulase. CelA is a very large bacterial enzyme that is difficult to express in fungal enzyme systems and due to its thermotolerance (85° C.) is incompatible to blend with existing fungal cellulases (50° C.). The present disclosure demonstrates it is possible to express novel fungal-based multifunctional enzymes in fungi such as *T. reesei* that exhibit equal or better performance compared to native free fungal cellulases. In an embodiment, novel multifunctional enzymes are expressed that exhibit unexpected improvements in their activity. In another embodiment, novel multifunctional enzymes are expressed that exhibit a synergistic improvement in activity over the sum of their various component activities.

Disclosed herein are active multi-modular cellulases similar designed and produced at significant titer in a fungal expression system. Table 1 describes some multifunctional enzymes exemplified herein:

TABLE 1

| Construct Name | Construct Structure |
| --- | --- |
| HC10-Link-E1 | FIG. 1A and B |
| HC10-2Link-E1 | FIG. 2A and B |
| HC10-CBM3-E1 | FIG. 3A and B |
| CBH1-Link-E1 | FIG. 4A and B |

TABLE 1-continued

| Construct Name | Construct Structure |
| --- | --- |
| HC10-2Link-GH9cbm3 | FIG. 5A and B |
| HC10-CBM1-E1 | FIG. 6A and B |

While Table 1 sets forth specific examples of multifunctional cellulases, many domain combinations from many enzymes are contemplated herein, based on catalytic domains (CDs), linker domains (linkers), carbohydrate binding modules (CBMs), and other domains from glycoside hydrolase (GH) family enzymes from microorganisms.

The exemplified constructs are based, for example, on the exoglucanase acting Cel7A enzyme coupled directly to an endoglucanase acting GH5 enzyme utilizing a short linker. Such constructs demonstrate that multifunctional enzymes can be successfully expressed at sufficient titer in fungal expression systems to be industrially relevant and that the enzymes are active at levels comparable or in excess to wild type produced cellulases. Further constructs explore different linker configurations and demonstrate the possibility of expressing non-*Trichoderma* CBM modules and additional bacterial cellulase domains in *T. reesei*.

The domains suitable for use in constructing multifunctional enzymes include catalytic domains, CBMs and linkers such as those from enzymes in the glycohydrolase (GH) family. In an embodiment, the GH families are 5, 6, 7, 9, 10, 11, 48, and 61, among others. Specific examples include the exo-glucanase Cel7 from *P. funiculosum* (HC10) the bacterial endo-glucanase E1 from *A. cellulolyticus*, Cel6A (CBH2) and Ce17 enzymes from *T. reesei*, as well as CBMs from *P. funiculosum* (e.g., CBM1) and from *C. bescii* (e.g., CBM3a, CBM3b, and CBM3c). In an embodiment, GH9 contains a CBM3c.

Enzymes may also include CBMs, linker domains, and CDs microbial cellulolytic enzymes other than those exemplified herein (e.g., from *A. cellulolyticus, P. funiculosum, T. reesei*, or *C. bescii*), including polypeptides from, for example, *Humicola insolens, Aspergillus niger, Chrysosporium lucknowense, Fusarium oxysporum, Hypocrea koningii, Melanocarpus albomyces, Neurospora crassa, Phanerochaete chrysosporium*, and *Thielavia terristris*, and others.

Multifunctional enzymes disclosed herein may exhibit enhanced activities over native enzymes, enhanced activity over combinations of native enzymes and even exhibit an unexpected synergistic enhanced activity when compared to the sum of the individual component enzyme activities. Such improvements may include increased cellulolytic activity, increased cellulose binding or increased thermostability.

Multifunctional cellulases are generally not known in eukaryotes, in part because of difficulties with processing and expressing multifunctional enzymes of any type in eukaryotic systems. However, from the standpoint of organism engineering, these enzymes are useful when expressed as single gene products, simplifying the production of enzyme cocktails and when genetically modifying organisms that lack native cellulolytic capability. In addition, these constructs may be easily tailored to different expression systems, both in eukaryote and prokaryote hosts, by selecting domains from appropriate sources and manipulating the expression control and post-translational modification motifs to the expression host. Enzymes with non-cellulase activities and binding domains (such as xylanases, mannanases, debranching, accessory, and others) can be used to alter the substrate specificity and activity.

In certain embodiments, a nucleic acid sequence presented in this disclosure may be identical to the sequence represented herein. In other embodiments, the nucleic acids may be least about 80%, 81%, 82%, 83%, 84%, 85%, 86%, 87%, 88%, 89%, 90%, 91%, 92%, 93%, 94%, 95%, 96%, 97%, 98% or 99% identical to a nucleic acid sequence presented herein, or 80%, 81%, 82%, 83%, 84%, 85%, 86%, 87%, 88%, 89%, 90%, 91%, 92%, 93%, 94%, 95%, 96%, 97%, 98% or 99% identical to a nucleic acid sequence presented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

The nucleic acid molecules exemplified herein encode polypeptides with amino acid sequences represented herein. In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the reference amino acid sequence while possessing the function. The present disclosure encompasses fungal cells that contain the nucleic acid molecules described herein, have genetic modifications to the nucleic acid molecules, or express the polypeptides described herein.

Suitable vectors for gene expression may include (or may be derived from) plasmid vectors that are known in the art, such as those commonly available from commercial sources, or exemplified herein. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including fungal, bacterial, yeast, and mammalian vectors, have been described for replication and/or expression in various host cells or cell-free systems, and may be used with genes encoding the enzymes described herein for simple cloning or protein expression.

Certain embodiments may employ promoters or regulatory operons. The efficiency of expression may be enhanced by the inclusion of enhancers that are appropriate for the particular cell system that is used, such as those described in the literature. Suitable promoters also include inducible promoters. Expression systems for constitutive expression in fungal cells are available from commercial sources. Inducible expression systems are also suitable for use.

In exemplary embodiments, the host cell may be a microbial cell, such as a fungal cell or a bacterial cell, and may be from any genera or species of fungi that is known to be genetically manipulable. Exemplary microorganisms include, but are not limited to, bacteria; fungi; archaea; protists; eukaryotes; and animals such as plankton, planarian, and amoeba.

Host cells may be cultured in an appropriate fermentation medium. An appropriate, or effective, fermentation medium refers to any medium in which a host cell, including a genetically modified microorganism, when cultured, is capable of growing and/or expressing recombinant proteins. Such a medium is typically an aqueous medium comprising assailable carbon, nitrogen and phosphate sources, but can also include appropriate salts, minerals, metals and other nutrients. Microorganisms and other cells can be cultured in conventional fermentation bioreactors or photobioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing fungal cells, for example, are available from ATCC.

Performance Testing Synthetic Multifunctional Enzymes

The synthetic multifunctional enzymes were compared to their parent components on a molar equal active site loading. A multifunctional enzyme with two active sites would be compared an equal number of active sites from its parent components. One hundred nmol of a multifunctional composed of Cel7a and Cel5a would have 200 nmol equivalents of active sites and would be compared to 100 nmol of Cel7a and 100 nmol of Cel5a (total 200 nmol).

The activity of the Cel7A-CBM1-Cel5A and Cel7a-Linker-Cel5a enzymes were roughly comparable or slightly inferior when compared to the binary component system of Cel7A-CBM1 and Cel5A. However, when the Cel7A-CBM3-Cel5A construct, also referred to herein as C3 and/or C3 raptor, was tested it dramatically outperformed the binary mixture of Cel7A-CBM1 and Cel5A enzymes by approximately 40% on the crystalline Avicel substrate, and dramatically outperformed Cel7a-CBM1 alone, see FIG. 16.

The hyperthermophilic CelA enzyme from *C. bescii* is agnostic to the crystalline content of cellulose. It converts high crystallinity (66% CI) cellulose at the same rate as low crystallinity cellulose (33% CI). In order to determine if the co-location of an exo and endo containing module could replicate this phenomena we tested the Cel7A-CBM1-Cel5A and Cel7A-CBM3-Cel5A multifunctional enzymes on both high and low crystallinity cellulose materials. The results shown in FIG. 18 indicate that while the Cel7A-CBM3-Cel5A construct performs better than the Cel7A-CBM1-Cel5A construct as previously observed, there is a distinct preference for the low crystallinity materials for both systems.

To evaluate whether our enzyme system could enhance a native cellulase preparation we once again added the three multifunctional enzymes to a commercial cellulase cocktail (ctec2) and compared the performance to the free binary enzyme system. The substrate tested was a dilute ammonia mechanically refined corn stover. As one can see in this case the Cel7A-CBM3-Cel5A and Cel7A-CBM1-Cel5A enzymes both improved the performance of the overall cocktail, however the Cel7A-Link-Cel5A enzyme performed only as well as the free enzyme system. While the overall extent of conversion at the endpoint is only somewhat elevated due to the overall high enzyme loadings used (10% improvement at endpoint) the actual rate of conversion is significantly faster for the Cel7A-CBM3-Cel5A and Cel7A-CBM1-Cel5A enzymes which achieve in 2 days what it takes the binary enzyme system to complete in 4 days, a 50% reduction in time to a targeted conversion (85%), see FIG. 11, for example.

Finally, we wanted to test the effect of the CBM3 module had on Cel7a and if this was responsible for the improved activity of the linked system. When compared on an equal active site basis to native pFun Cel7A with a CBM1, the CBM3 containing construct was shown to have inferior activity to the native enzyme. This is not a surprising result given that nature has optimized the Cel7 catalytic domain to perform well with CBM1 module, see FIG. 23, for example.

For enzymatic deconstruction, we tested a Cel7-CBM3 only construct to determine whether or not the increase in activity for the Cel7a-CBM3-Cel5a construct could be accounted for by adding a CBM3. This data is presented in FIG. 23. As one can see the WT Cel7a-CBM1 construct clearly outperforms the Cel7a-CBM3 construct which indicates that merely adding CBM3's to Cel7's is not beneficial. Rather that there is a novel emergent property in the Cel7a-CBM3-Cel5a construct.

A multifunctional (Cel5a-CBM1-CMB1-Cel6a) construct (EG) was cloned, expressed, and purified. The construct was expressed in QM9414 and grown in an 8 L batch fermenter. The construct was purified from the secreted broth using the same HIC purification strategy previously employed to purify the other multifunctional constructs.

Thus far the construct has been compared to our earlier multifunctional CBM containing enzymes. Its performance is comparable to our earlier C1 (Cel7a-CBM1-Cel5a) construct. However, when combined with the C3 multifunctional (Cel7a-CBM3-Cel5a) we see an unexpected and very significant synergistic effect.

Construct Generation

Multifunctional gene cassettes were designed in the parent vector HC10-Link-E1 to generate HC10-2Link-E1, HC10-CBM3-E1, HC10-CBM1-E1 and HC10-2Link-GH9cbm3 containing constructs. An additional construct, CBH1-Link-E1, was also designed.

For generation of HC10-2Link-E1, the *T. reesei* Cel6A linker sequence followed by an in-frame *A. cellulolyticus* E1 sequence were synthesized such that a BamHI site and an XbaI site were introduced at its 5' and 3' ends, respectively. This fusion Cel6A linker-E1 sequence was then introduced into the parent HC10-Link-E1 (pTreno-HC10-Link-E1 vector) at the BamHI-XbaI restriction sites to generate the final HC10-2Link-E1 plasmid.

The plasmid construct HC10-CBM3-E1 was generated as follows. A codon optimized cellulose binding domain 3 (CBM3) sequence from the cellulolytic bacterium *Caldicellulosiruptor bescii* was synthesized as a fusion with *T. reesei* Cel6A and *A. cellulolyticus* E1 sequence such that a BamHI and an XbaI site was introduced at its 5' and 3' ends, respectively. This synthesized sequence was introduced into the parent vector (HC10-Link-E1) at the BamHI-XbaI restriction sites to generate the desired vector.

The plasmid CBH1-Link-E1 was generated by synthesizing the CBH1-linker fusion after destroying an internal BamHI site present within the CBH1 sequence. Additionally, a PacI and a BamHI site was introduced at the 5' and 3' ends of the sequence, respectively. This synthesized sequence was then introduced into the PacI-BamHI sites of the parent vector HC10-Link-E1 to obtain the final plasmid.

The plasmid HC10-2Link-GH9cbm3 was generated by generating a fusion sequence of *T. reesei* Cel6a linker—*Lachnoclostridium phytofermentans*_T00619 cbm3 (GH9cbm3) sequence such that a BamHI and XbaI sites were introduced at their 5' and 3' ends, respectively. The GH9cbm3 sequence was codon optimized for expression in *T. reesei*. Each of these plasmid constructs were transformed into *T. reesei* AST1116 strain or the strain QM9414 and selected on media containing hygromycin at a concentration of 100 µg/ml.

The C1lnk-C3lnk construct is the abbreviated name for the PfunCBH1+lnk-cbm1-Trcbh2lnk-CBM3-Trcbh2lnk-E1 protein, wherein a cbcbm3-Trcbh2lnk sequence has been introduced immediately following the Pfcbm1-Trcbh2lnk sequence within the C1lnk construct. Briefly, the cbcbm3-Trcbh2linker insert sequence was amplified using primer SV291 (GTT GCA GGT GGA CAG ATT AAA GTG) and SV292 (TCC CGA TCC GAC TGG AGG TAC) from the original C3lnk vector. The vector fragment was amplified using primers SV-289 (GTC CAC CTG CAA CTC CCG ATC CGA CTG G) and SV-290 (CAG TCG GAT CGG GAA AGC TGG CTG GCG) so as to have overlapping sequences with the insert sequence. After DpnI treating the vector PCR product, both the insert and the vector fragments were ligated using Infusion cloning (Takara Bio, USA) master mix. After confirming for the correct nucleotide sequence, the plasmid was linearized with SbfI enzyme and transformed into AST1116 strain. We have screened one set of colonies for detection of the fusion protein, which has not yielded any positive transformants. We are currently carrying out additional transformation experiments to obtain more colonies for screening purposes.

The 2X-C3lnk construct is the abbreviated name for the PfunCBH1+lnk-2X cbcbm3-Trcbh2lnk-E1 protein, where in the cbcbm3-Trcbh2lnk sequence has been repeated twice in tandem. Briefly, the cbcbm3-Trcbh2linker was amplified from the original C3lnk construct with primers SV-287 (GAG GAT CCG TTG CAG GTG GAC AG) and SV-288 (CGG ATC CTC CCG ATC CGA CTG G) so as to introduce a BamHI site at either ends. This product was cloned into the temporary vector pJET1.2 (Thermofisher Scientific). In parallel, the C3lnk construct was linearized with BamHI enzyme. The BamHI restriction site was strategically placed in the original C3lnk construct immediately after the PfunCel7A linker sequence so as to be used for future modification purposes as done here. The cbcbm3-Trcbh2linker fragment was excised from the pJET1.2 clone using BamHI enzyme and then ligated with the linearized C3lnk vector to obtain the final plasmid. This plasmid was linearized with SbfI enzyme and transformed into AST1116. We are currently screening for identification of a 2X-C3lnk expressing transformant by western Construct Purification The multifunctional constructs had similar purification schema with only minor differences. Multifunctional enzymes were purified primarily utilizing hydrophobic interface chromatography. Briefly, fungal broth containing a multifunctional enzyme was run over a Source 15 Phe column with a pH 5 20 mM sodium acetate buffer containing 1M ammonium sulfate. The gradient was reduced to about 0% ammonium sulfate, and the construct was eluted. The construct was further purified by size exclusion chromatography.

Enzyme Activity Assays

As used herein, HC10 is synonymous with Cel7a from *P. funiculosum*. To determine if both the CBH1 and E1 domains of HC10-Link-E1 were active, a binary PNP assay was used. CBH1 has preferential activity on 4-Nitrophenyl β-D-lactopyranoside (PNP-L), and E1 has preferential activity on 4-Nitrophenyl β-D-cellobioside (PNP-C); a fully functional and intact HC10-Link-E1 would have high activity on both substrates. *P. funiculosum* HC10, *A. cellulolyticus* E1, and HC10-Link-E1 (each at about 0.36 mg/ml final concentration) were added to 1 mM PNP-C and PNP-L substrates buffered in 20 mM acetate pH 5 buffer and incubated at 50° C. for 10 minutes.

Figure 7:
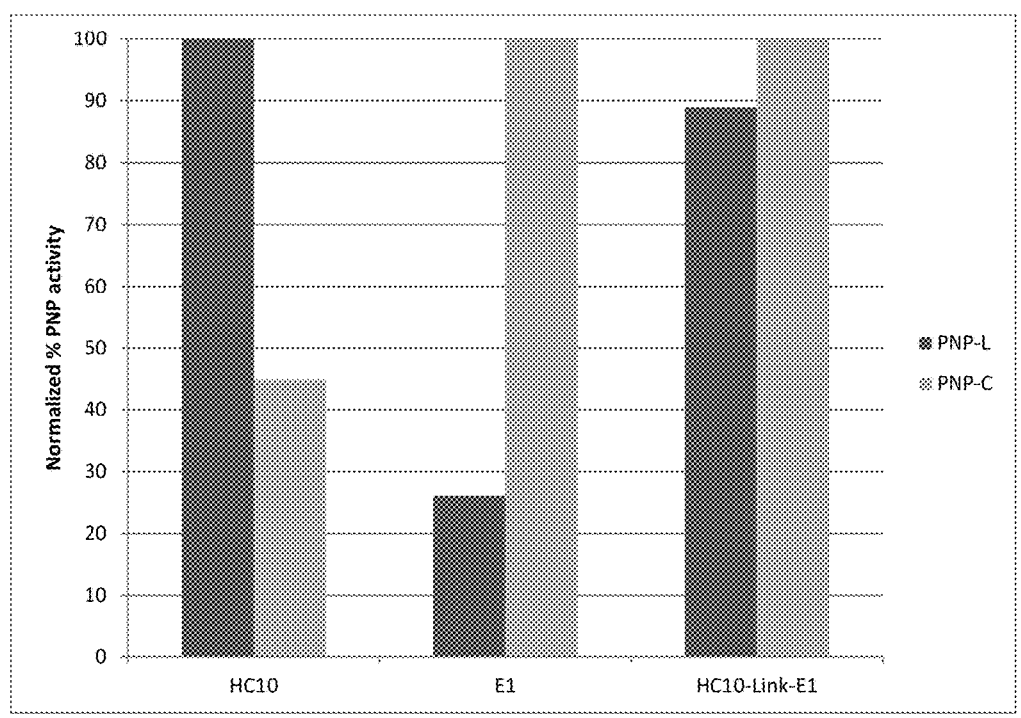
FIG. 7 shows normalized PNP response of HC10, E1 and the HC10-Link-E1 construct.

Testing on the soluble PNP substrates takes advantage of the differential enzyme responses to different PNP substrates, it can be seen that HC10 preferentially digests PNP-L, while having limited PNP-C activity. E1 on the other hand has a strong preference for cleaving the PNP-C substrate over PNP-L. To determine if both domains of the multifunctional were expressed correctly and were active, the enzymes were run on both PNP substrates. As shown in FIG. 7, the multifunctional works well on both PNP-L and PNP-C, see FIG. 7.

Binding and Biomass Interaction Data

To better understand the interaction of the enzymes with solid substrates we performed binding tests utilizing an Avicel pull down technique and quantitated the bound and unbound enzyme fractions. These results indicate that the Cel7A-CBM3-Cel5A enzyme is the most bound enzyme, the C1 and C2 enzymes are not quite as tightly bound. The C1 enzyme appears to be less bound to cellulose when compared to Cel7 alone. Without being bound by theory, this may suggest that the CBM1 module is not capable of binding cellulose as well when placed in the middle of a construct, rather than at the end.

QCM experiments were also conducted to evaluate the rate of binding. The initial linear binding rates indicate that the Cel7A-CBM3-Cel5A enzyme has the fastest binding rate of all enzymes tested, including CbCelA and PfCel7A, see FIG. 17. The other Cel7A-CBM1-Cel5A and Cel7A-Link-Cel5A have a comparable binding rate to CelA.

When compared to the other enzymes tested under inhibitory concentrations of cellobiose, the Cel7A-CBM3-Cel5A enzyme rapidly binds, but then also non-catalytically causes the cellulose surface to soften and lose mass. When compared to all of the bound enzymes they rapidly come to an equilibrium state, that is the flat portion of the curve seen in FIG. 20 until the wash step where they are removed, except for Cel7A-CBM3-Cel5A that immediately upon binding to the substrate starts to "soften" the biomass and causes mass loss can be seen in FIG. 20. Given that the major difference between Cel7A-CBM1-Cel5A, Cel7A-Link-Cel5A and Cel7A-CBM3-Cel5A is the CBM it is logical to assume that this may be the consequence of the CBM3, however when CelA (which contains 3 CBM3's) is tested, this phenomenon does not occur. Nor do we see this phenomenon when only a CBM3 is bound to the sensor surface, see, for example FIGS. 27, 28 and 29. FIGS. 27, 28 and 29 also depict QCM data of the CBM3(b) on cellulose and show that it is not responsible for the mass-loss effect that the C3 construct exhibits.

Solid Substrate Digestions

The ability of multifunctional enzymes to digest several substrates (crystalline Avicel; de-acetylated, disc refined corn stover; and alkaline peroxide treated corn stover) was tested using mixtures of free enzymes and multifunctional enzymes. Most loadings were near 10 mg/g glucan loading, but typically loaded on either an actual molar basis or "equal active sites basis" when compared to a mixture of free HC10 and E1 enzymes to evaluate improvements in synergistic performance on substrates. Digestions were performed at a 1-2% total solids loading and at 50° C., with time points taken every 24 hours. High solids digestions were performed at the same enzyme loadings and a 20% solids loading, in this case only a 5 day digestion time point was obtained. Specific loadings used were as follows HC10 at 10 mg/g, HC10 at 5.8 mg/g+E1 at 4.2 mg/g, HC10-link-E1 at 9.2 mg/g, HC10-2Link-E1 at 9.6 mg/g, and HC10-CBM3-E1 at 11.34 mg/g glucan. These loadings were calculated to give the exact same number of actual active sites on a molar basis, so valid comparisons could be made between constructs. The actual molar loading of the multifunctional enzymes is approximately one-half of the non-linked enzyme systems, but since the multifunctional enzymes contain two active domains, the overall comparison is valid.

Figure 8:
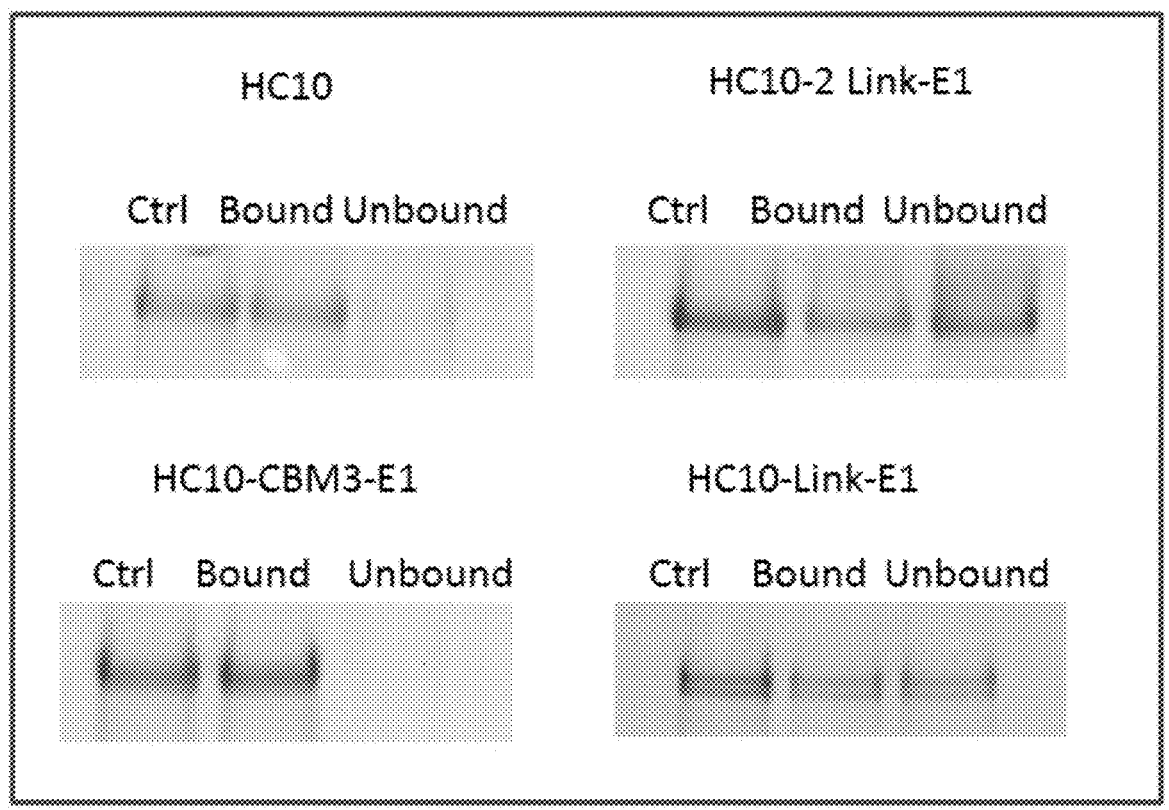
FIG. 8 shows a Coomassie stained gel of bound and unbound fractions of the indicated enzymes to Avicel.
Figure 9:
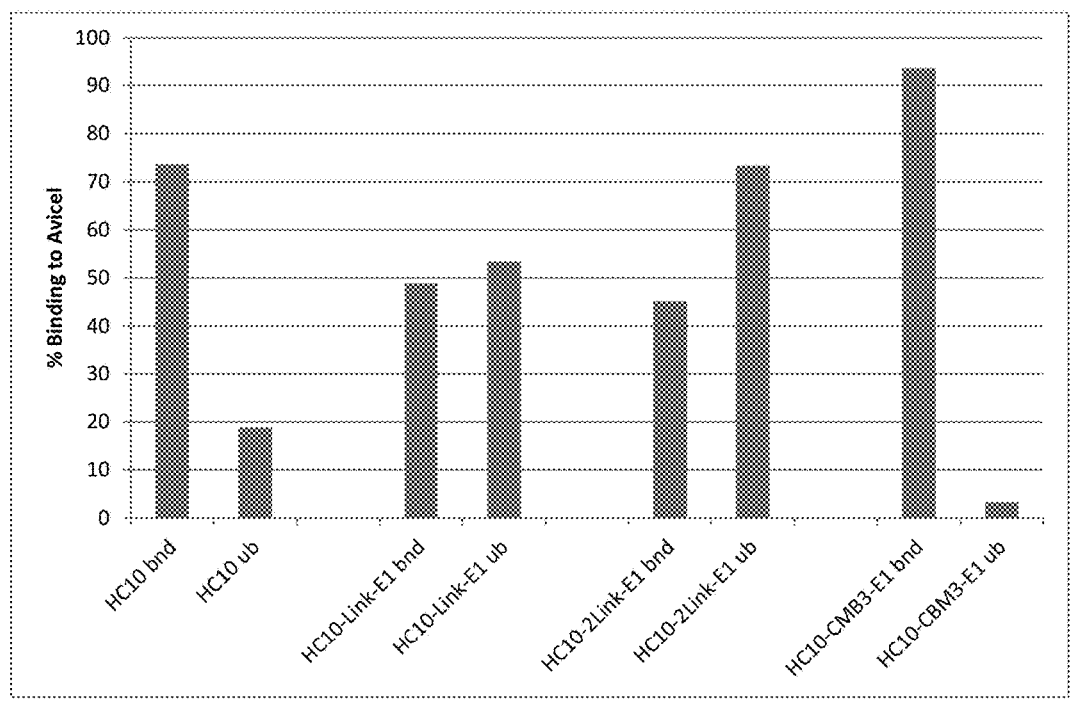
FIG. 9 shows the quantitation of enzyme binding results shown in FIG. 8 using imageJ software.

The multifunctional enzymes show different binding properties when compared to full length HC10. The HC10-Link-E1 and HC10-2 link-E1 constructs are not fully bound to the crystalline cellulose substrate, whereas the HC10 and HC10-cmb3-E1 constructs are almost entirely bound to the substrate (FIGS. 8 and 9). Without being bound by theory, it has been postulated that while catalytic domains can bind productively to cellulose, the primary role of CBMs is to effect the off-rate of enzyme disassociation from the substrate, rather than the actual on-rate (binding and catalytic module threading to the cellulose).

Imaging

Imaging by scanning electron microscopy (SEM) was performed using an FEI Quanta 400 FEG instrument under high vacuum operating at beam accelerating voltage of 20 keV with the Everhart-Thornley detector (secondary electron detector). Samples were prepared for imaging by freezing in liquid nitrogen followed by lyophilization. Dry samples were mounted on aluminum stubs using carbon tape, and conductive silver paint was applied to the sides of the samples to reduce sample charging, then sputter coated with 10 to 12 µm Iridium thickness. Four sample types were imaged for comparison examining at least 10 regions of interest (ROI) each in a zoom series format of various magnifications, ranging from 1000× to 50,000×. The samples included Avicel (PH101) as the control and Avicel digested with CelA+E1, HC10+E1, or HC10-CBM3-E1.

Lower magnification images demonstrate that all three enzymatic configurations have an effect on the physical size and fractionation of the Avicel sample as compared to the larger particle sizes characterized in the control Avicel (PH101) sample, which are nominally between 50 and 100 µm. In most fields of view, the average reduction in particle size appears to be in the 40-60 µm range, suggesting effective digestion in all cases (FIG. 13). Interestingly, the enzymatic mechanisms by which the Cel A+E1 and HC10-CBM3-E1 cocktails appear to digest cellulose are of a delamination and separation method where by S1 and S1 layers of the plant cell wall are wedged up from their native locations and systematically removed the particle's mass. On the more macro-molecular level (FIG. 14), the surface erosion patterns appear a bit more dramatic in the case of Cel A+E1 and HC10-CBM3-E1 as well, which may indicate some sub-surface cellulose digestion in combination with the delamination mechanism noted above.

Multifunctional Enzymes Activity

Figure 10:
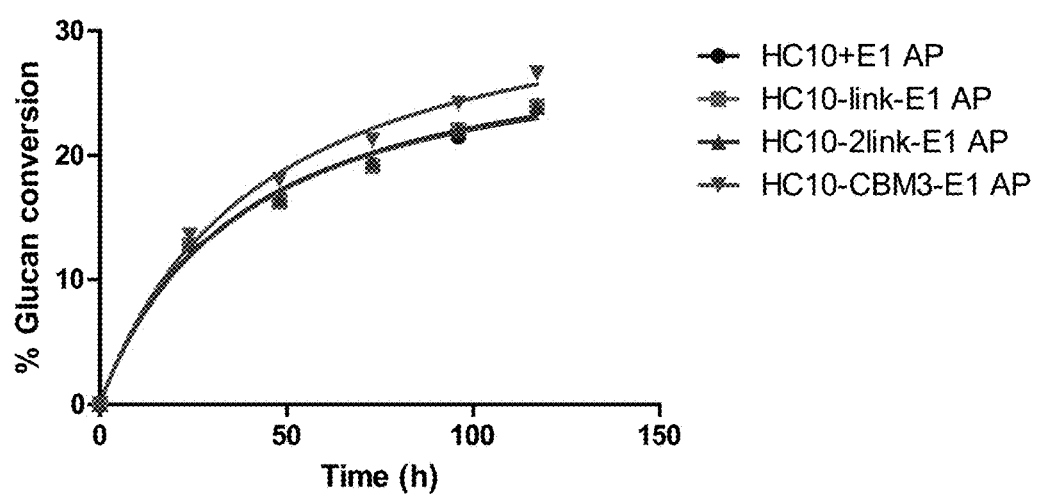
FIG. 10 shows the enzymatic performance of multifunctional enzymes compared to HC10 and unlinked HC10+E1 enzymes on alkaline peroxide pretreated corn stover.

Multifunctional enzymes were tested on a crystalline Avicel substrate at comparable equal active site loadings, which roughly correspond to equal mg/g biomass protein loadings. All multifunctional constructs tested outperform HC10 alone at a lower or near equal mg/g loading, and at roughly half the actual molar loading. As shown in FIG. 10, when compared to a synergistic mixture of HC10 with E1 added and compared on an equal number of active sites basis, the HC10-CBM3-E1 construct significantly outperforms the unlinked enzymes on Avicel, demonstrating that there is additional benefit provided by using a CBM3 under these conditions.

The multifunctional enzymes work equally well compared to the HC10+E1 synergistic mix on the DDR substrate. When tested on the AP treated substrate the HC10-CBM3-E1 construct outperforms the free enzyme control mixture of HC10+E1 (FIG. 10).

Multifunctional enzymes were compared on an equal active site basis to HC10 and HC10+E1 on the crystalline cellulose substrate Avicel. Once again, all of the multifunctional enzymes outperformed HC10 alone, and were roughly equal to the HC10+E1 mixture (FIG. 12). The HC10-Link-E1 and HC10-2 Link-E1 multifunctional enzymes perform as well as the free enzyme mix at high solids. Results indicate that the lack of a CBM does not appear to be problematic for the extent of conversion.

Figure 11:
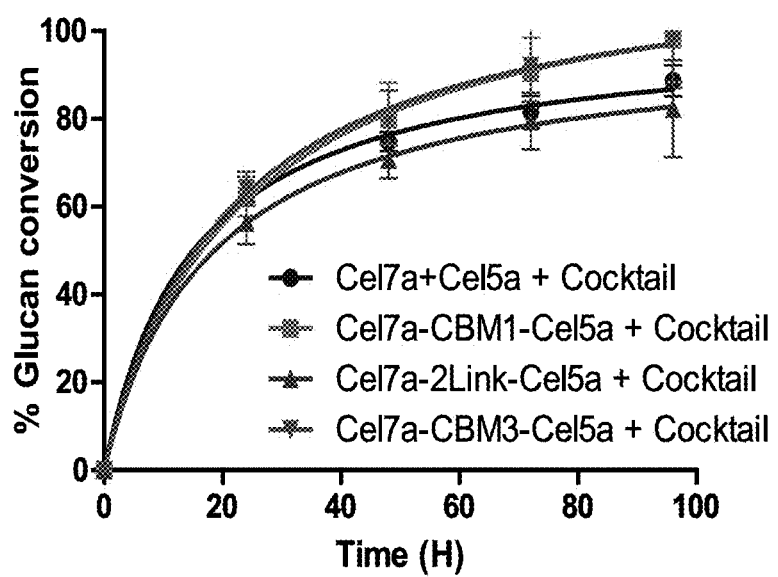
FIG. 11 depicts the enzymatic performance graphs of multifunctional enzymes. As depicted in FIG. 11, CBM3 linked C3 exhibits a 10% improvement in endpoint conversion as well as a 50% reduction in time to 90% target conversion.

As depicted in FIG. 11, C3 exhibits an unexpected improvement in activity with a 50% reduction in time to a 90% conversion of substrate. The C3 construct's improvement of a 50% reduction in time to achieve 90% target conversion is much more than the sum of the activities of the individual parts of the C3 construct. Also depicted in FIG. 11 is an overall 10% improvement in endpoint conversion of the C3 construct with respect to the free enzymes.

Transformation and Screening of *T. reesei* Clones

Twenty-four colonies were screened for HC10-2Link-E1 by transferring spores from individual colonies to 2 ml of MAG medium containing hygromycin. Based on Western Blotting, only one colony expressed the protein of the expected molecular weight (about 95.97 kDa). A small mycelial fragment from the positive clone was transferred to PDA agar containing hygromycin (PDH) to allow sporulation. A spore suspension was prepared from this colony and streaked on PDH plate containing Triton-X to obtain clonal isolates. Five independent colonies were then screened for expression of the HC10-2Link-E1 fusion cassette by Western Blotting. Clonal isolate #3 was selected as the purified clone for growing in fermenters for large-scale protein expression, purification and catalytic studies.

For identification of HC10-CBM3-E1, 58 clones were screened by Western Blotting using an antibody specific for *P. funiculosum* CBH1 by the same approach described above. Two transformants (#1 and #19) showed the presence of a protein of the expected molecular weight (about 113.18 kDa). One positive colony was further subjected to the clonal isolation procedure as described above. One isolate was further selected based on expression of the fusion protein, for large scale expression, purification and catalytic studies.

The HC10-CBM3-E1 plasmid construct was also transformed into another strain of *H. jecorina* (AST1116) to examine any strain specific effect on expression of this construct. Similar to strain QM9414, a low frequency of successful protein expressing transformants was observed. However, the level of expression of one of the clones was higher than that observed in any of the transformants from QM9414. Moreover, the clonal isolates obtained from clone A11 also showed higher protein expression levels. One of the clonal isolates was selected for large scale expression, purification and catalytic studies.

With respect to CBH1-Link-E1, 12 transformants from strain AST1116 were screened using the same approach described above. Two transformants showed bands of the expected molecular weight by Western Blotting, suggesting that these are the expressing clones. Clonal isolates for each of the two positive transformants were then generated. Based on Western Blotting, the clonal isolates originating from A1 transformant showed better expression levels than the A2 clones. One of these clonal isolates was thus further selected for large scale expression, purification and catalytic studies.

The multifunctional construct HC10-2Link-GH9cbm3 is transformed into strain AST1116 or QM9414 and selected for hygromycin resistant colonies. Transformants and clonal isolates are screened and selected using the procedures set forth above.

Fermentation

Transformed *Trichoderma reesei* cell culture was streaked on a Potato Dextrose Agar plate and allowed to grow 2-3 days until a well lawned plate of spores was achieved. A ~0.5 cm plug was extracted from the plate and deposited into 1 L of liquid growth media in a 2.8 L shake flask. The growth media consisted of Mandel's Growth Media with 5% glucose as the carbon source, and 0.5% tryptone added. The culture was grown at 28° C. with agitation for 24 hours, after which the entire 1 L was transferred to 7 L of the same media, in a bioreactor. The bioreactors were L working volume vessels manufactured by New Brunswick and controlled via New Brunswick's BioFlo310 system. The total of 8 L was grown with mixing at 300 rpm via dual down-flow marine style impellers, purged with 1.5 VVM of filtered air, kept at a strict 28° C., and pH controlled at 4.8. The acid and base used for pH control was HCl and KOH, respectively. The cell culture was grown for 48 hours, after which the entire culture broth was drained, filtered through nylon to remove all cell mass, and concentrated via tangential flow filtration with a 10,000 Dalton MWCO (GE Health Sciences). The concentrated broth was buffer exchanged into 20 mM Bis-Tris pH 6.5, and brought up to approximately 200 ml.

Fermentation broths (about 8 to about 10 L) were harvested and sequentially vacuum filtered through the following series: (1) Miracloth (EMD Biosciences), (2) 2 µM glass fiber filter, (3) 1.1 µM glass fiber, and (4) a 0.45 µM PES membrane. This filtered broth was then concentrated by tangential ultrafiltration with a 10,000 Da MWCO. Broths were roughly concentrated from 8 L to 150 mL. This volume was exchanged with at least 1 L of 20 mM Bis-Tris pH 6.5 buffer to remove residual peptides and other low molecular weight debris. This concentrate was then re-filtered to 0.2 µM and the filtrate was adjusted to 1.5 M (NH4)2SO4 for hydrophobic interaction chromatography (HIC) and then loaded onto a 26/10 Phenyl Sepharose Fast Flow column. For HIC, buffer (A) is 20 mM Bis-Tris pH 6.5 and buffer (B) is 20 mM Bis-Tris pH 6.5, 2M (NH4)2SO4. Buffers were run 80% B to 0 over 8 column volumes. Active fractions are identified by a pNP-lactose (pNPL) activity assay (pNPL at 2 mM in 50 mM acetate pH 5.0.) One hundred µL of pNPL added to each well of a 96-well plate. Twenty-five µL of each fraction were added and the plate incubated 30 min at 45° C. Reactions were quenched with 25 µL of 1 M NaCO3 and the absorbance at 405 nm (A405) was measured. Standard curve concentrations ranged from 0 to 250 µM pNP.

pNPL-active fractions were pooled and concentrated as needed. Protein was desalted and exchanged into 20 mM Bis-Tris pH 6.5 buffer. We next utilized a 10/100 anion exchange column packed with Source 15Q run at 0 to 50% 30 cv, the buffers were 20 mM Bis-Tris pH 6.5 and same buffer+1 M NaCl. pNP-lactose activity was followed again to identify active fractions. SDS-PAGE and Cel7A immunoblotting was performed to assess purity. The final stage of purification consisted of size exclusion chromatography (SEC) using 26/60 Superdex 75 column and 20 mM acetate pH 5.0 buffer containing 100 mM NaCl.

For single antibody Western blots immuno-detection of Cel7A was achieved using the SNAP i.d. Protein Detection System (Millipore Corp., Billerica Mass.). The PVDF membrane was blocked using SuperBlock PBS (Thermo Fisher Scientific Inc., Rockford, Ill.) for 20 min. Rabbit anti-Cel7A polyclonal IgG was used as the primary antibody (1:20,000 dilution of crude serum), with alkaline phosphatase-conjugated goat anti-rabbit IgG (Thermo Fisher Scientific Inc., Rockford, Ill.) as secondary. The alkaline phosphatase localization was visualized using BCIP/NBT (Life Technologies Corp., Carlsbad, Calif.).

Multifunctional Enzyme Purification

CelA purification—A hydrophobic affinity purified *C. bescii* broth enriched in CelA was utilized for the CelA mix data reported here, this is not the raw *C. bescii* exproteome, rather it is enriched in the hydrophobic components such as CelA that represents a the majority of the activity of the broth. For the experiments requiring pure CelA, CelA was tagged with 6xHis tag, and expressed in *C. bescii*. CelA was purified out of the *C. bescii* exoproteome using a 5 mL HisTrap fast flow column (GE) and was further purified using a Superdex 26/60 200 PG column.

Cel7A Production and Purification

The transformed *Trichoderma reesei* cell culture was streaked on a Potato Dextrose Agar plate and allowed to grow 2-3 days until a well lawned plate of spores was achieved. A 0.5 cm plug was extracted from the plate and deposited into 1 L of liquid growth media in a 2.8 L shake flask. The growth media consisted of Mandel's Growth Media with 5% glucose as the carbon source, and 0.5% tryptone added. The culture was grown at 28° C. with agitation for 24 hours, after which the entire 1 L was transferred to 7 L of the same media, in a bioreactor. The bioreactors were 15 L working volume vessels manufactured by New Brunswick and controlled via New Brunswick's BioFlo310 system. The total of 8 L was grown with mixing at 300 rpm via dual down-flow marine style impellers, purged with 1.5 VVM of filtered air, kept at a strict 28° C., and pH controlled at 4.8. The acid and base used for pH control was HCl and KOH, respectively. The cell culture was grown for 48 hours, after which the entire culture broth was drained, filtered through nylon to remove all cell mass, and concentrated via tangential flow filtration with a 10,000 Dalton MWCO (GE Health Sciences). The concentrated broth was buffer exchanged into 20 mM Bis-Tris pH 6.5, and brought up to ~200 ml.

*T. maratima* β-D-glucosidase and β-xylanase were purchased from Megazyme (Bray, Ireland) samples were desalted using a Hi-trap 26/10 (GE life sciences) desalting column before use to remove ammonium sulfate stabilizer.

Biomass Pre-Treatment DMR

Generation of cellulose at varying degrees of crystallinity: Amorphous cellulose and cellulose-I at varying degrees of crystallinity were prepared from cotton linters (CAS Number 9004-34-6; catalogue number 22183) obtained from Sigma-Aldrich. Briefly, 1 g of dry cellulose powder was added to 30 mL of ice-cold concentrated phosphoric acid. The slurry was allowed to react at 0° C. for 40 min with occasional stirring. After 40 min, 20 mL of ice-cold acetone was added to the slurry followed by stirring and filtration on a sintered glass crucible. The filtered sample was further washed three times each with 20 ml of ice-cold acetone and DI water. The resulting cellulose was freeze-dried. The cellulose-I samples at reduced crystallinity (PASC-CL, CI-44 and PASC-CL, CI-34) were prepared by varying the phosphoric acid concentration using the same method describe above.

X-Ray Diffraction Measurements

The crystallinity indexes (CI) of cellulose samples were measured by X-ray diffraction (XRD) by using a Rigaku (Tokyo, Japan) Ultima IV diffractometer with CuKα radiation having a wavelength λ(Kα1)=0.15406 nm generated at 40 kV and 44 mA. The diffraction intensities of dried samples placed on a quartz substrate were measured in the range of 8 to 42° 2θ using a step size of 0.02° at a rate of 2° min'. The crystallinity indexes of the cellulose samples were measured according to the amorphous subtraction method. A diffractogram of amorphous cotton linter cellulose sample mentioned above was subtracted from the other cellulose samples to remove the influence of the amorphous component in the diffractograms. The ratio of the integrated area of each subtracted diffractogram to the area of the original was then calculated and multiplied by 100 to give the CI value of the sample.

Compositional Analysis of Pretreated Solids

To determine the structural carbohydrates and lignin components of the pretreated solids, a compositional analysis was conducted.

Lignin extraction method: Steam explosion pretreatment of corn stover. Pretreatment of corn stover was conducted in a four-L steam explosion reactor at 180° C., 1 wt % $H_2SO_4$, for 3 min. The reactor is constructed of Hastelloy C-22 for corrosion resistance. A two-inch thick insulating jacket surrounds the steam jacket and temperature controlled electrical heating bands that encase all external surfaces of the reactor, limiting heat loss to the environment, and reducing condensation inside the reactor during pretreatment. The pre-warmed reactor was loaded with 500 g of acid impregnated and pressed corn stover (~43% solids), sealed with the top ball valve, and steam applied to both the top and bottom of the reactor interior to quickly heat (~5 to 10 s) the biomass to reaction temperature. The timer is started when the reactor contents measured by two thermocouples inside the reactor reach reaction temperature. The bottom ball valve is quickly opened at the desired experimental residence time and the pretreated solids are blown into a nylon HotFill® bag inside a 200-L flash tank. The bag is removed from the flash tank, labeled, sealed, and stored at 4° C. until ready for analysis. This allows collection of all steam and volatile components (furfural and acetic acid) in the slurry for more accurate component mass balance measurements.

Avicel Substrates Enzyme Digestions

Differentially pretreated substrates were digested at a total enzyme loading of 15 mg/g glucan. For CelA, digestions we utilized 11.5 mg/g of CelA broth, 3 mg/g E1, and 0.5 mg/g β-D-glucosidase as discussed in the enzyme purification section. For the second digestion set, the loadings for DACS and APCS were 10 mg/g CelA broth, 2 mg/g E1, 2 mg/g β-D-xylosidase and 0.5 mg/g β-D-glucosidase. For the CFCS substrate, it was necessary to lower the total loading to 5 mg/g glucan the composition in this case was: 4.25 mg/g glucan, 0.5 mg/g E1 and 0.25 mg/g beta glucosidase. CTec2 from Novozymes was used as a model fungal free enzyme system and was loaded at either 15 mg/g in all cases or 5 mg/g glucan for the CFCS substrate. CelA mix digestions were performed at 75° C. at pH 5.5 while the CTec2 based digestions were run at 55° C. pH 5.0. All digestions were conducted at a total initial solids loading of 1%.

Digestions were run continuously for 5 days with sampling at various time points. Enzymes were inactivated by boiling for 15 min after which samples were filtered through 0.45 mm Acrodisc syringe filters. The released sugars were analyzed by HPLC. Samples were injected at 20 μL volume and run on an Agilent 1100 HPLC system equipped with a BioRad Aminex HPX-87H 300 mm×7.8 mm column heated to 55° C. A constant flow of 0.6 mL/min was used with 0.1M $H_2SO_4$ in water as the mobile phase to give optimal sugar separation. Glucose, xylose, cellobiose and xylobiose were quantified against independent standard curves and converted to anhydrous glucan equivalent and the results are reported as anhydrous glucan converted. All experiments were performed in triplicate and the resulting extents of conversion are shown as percent glucan or xylan converted.

Differential Crystallinity Cellulose Digestions

Three differential crystallinity substrates were digested with CelA complemented with a *T. maritima* β-D-glucosidase. Total protein loading was 14.5 mg/g CelA and 0.5 mg/g β-D-glucosidase. Experiments were run in triplicate at 80° C. Cel7A from *T. reesei* and E1 from *A. cellulolyticus* were loaded at 7.25 mg/g each and 0.5 mg/g β-D-glucosidase. Experiments were run in triplicate at 50° C. All digestions were conducted at a total initial solids loading of 1%. Digestions were run continuously for 5 days with sampling at various time points. Enzymes were inactivated by boiling for 15 min after which samples were filtered through 0.45 mm Acrodisc syringe filters. The released sugars were analyzed by HPLC following the protocol described above.

SEM and TEM

Imaging of digestion of Avicel substrates by various constructs was performed by both TEM (FIG. 21) and SEM (FIG. 22). The different enzymes do appear to have different mechanisms of biomass degradation as seen in FIGS. 21 and 22. Cel7A-CBM1-Cel5A and to some extent Cel7A-Link-Cel5A by TEM appear to have a very diffuse digestion pattern (FIG. 21), and when viewed by SEM this looks like a smooth surface (FIG. 22). In contrast, the Cel7A-CBM3-Cel5A construct has a much more scalloped appearance, with particles that appear to flake off the surface of the Avicel. This is similar but distinct from CelA that has a pit-formation mechanism. No pit formation phenotype was detected by TEM for the Cel7A-CBM3-Cel5A construct (FIG. 21). However, the SEM deconstruction pattern does have some CelA like features. The other notable feature was that the C3 SEM digest showed a large amount of what appear to be cellulose nano-crystals (FIG. 22).

To evaluate the formation of cellulose nano-crystals DSC measurements were performed. The C3 construct does produce a fraction of cellulose nano-crystals.

TEM imaging of multifunctional digested substrates was performed to better understand their mechanism of action. Several novel themes emerged. TEM imaging to characterize both Cel7a from *T. reesei* and the hyperthemophillic CelA from *C. bescii* indicated that Cel7a digested Avicel had a unique tip sharpening morphology that was attributed to its processive digestion mechanism. CelA on the other hand had different mechanism that left blunt/scalloped ends and formed pits or cavities into the cellulose surface.

The multifunctional C1, C2, and C3 constructs were imaged in a similar fashion and the results are depicted in FIG. 21. The C1 and C2 constructs display an interesting nano-whisker morphology present around the edges of the material this is not seen with the original Cel7a digestions, furthermore the tip-sharpening morphology is present, but to a lesser degree than the Cel7a digestions. The C3 construct has a different morphology present, a flaking or fragmenting morphology is noted by the presence of small particles clinging to the surface of the particle, also a CelA like end disruption morphology is also present, however no CelA like cavities or pits were noted.

Biomass Substrate Microscopy

Digested, pretreated corn stover tissue was processed using microwave EM processing. Briefly, samples were fixed 2×6 min in 2.5% glutaraldehyde buffered in 0.1 M sodium cacodylate buffer (EMS, Hatfield, P S) under vacuum. The samples were dehydrated by treating with increasing concentrations of ethanol and heating in Pelco microwave oven for one min each dilution (i.e., 30%, 60%, 90%, and 3×100% ethanol). After dehydration, the samples were infiltrated with LR White resin (EMS, Hatfield, Pa.) by incubating at room temperature (RT) for several hours to overnight in increasing concentrations of resin (30%, 60%, 90%, 3×100% resin, diluted in ethanol). The samples were transferred to capsules and the resin polymerized by heating to 60° C. overnight in a vacuum oven.

Microtomy and Immuno-labeling—Resin-embedded samples were sectioned to ~60 nm with a Diatome diamond knife on a Leica EM UTC ultramicrotome (Leica, Wetzlar, Germany). Sections were collected on 0.5% Formvarcoated palladium/copper slot grids (SPI Supplies, West Chester, Pa.). Grids were placed on ~10 μp drops of 2.5% non-fat dry milk in 1× phosphate-buffered saline-0.1% Tween (PBST) for 30 min, then directly placed on ~10 lar, Germany). Section antibody probes diluted 1:50 in 1% milk PBST and incubated overnight at 4° C. Following a one min rinse with 1×PB ST and 3× one min rinses with nano-pure water, grids were placed on drops of buffered saline-0.1% Tween (PBST) for 30 min, the BioCell) diluted 1:500 in 1% milk PBST and incubated overnight at 4 diluted 1:500 in 1% milk PBST and incubated overnight at line-0.1% Tween (PBST) for nano-pure water.

Confocal Scanning Laser Microscopy (CSLM)—Semi-thin sectioned samples were positioned on glass microscope slides and stained with 0.1% acriflavine. Samples were excited at 488 nm and an emission range from 510-630 nm was captured. Images were captured using a 40×1.4 NA Plan Apo lenses on a Nikon C1 Plus microscope (Nikon, Tokyo, Japan), equipped with the Nikon C1 confocal system operated via Nikon's EZ-C1 software.

Transmission Electron Microscopy (TEM)—Grids were post-stained for three minutes with 2% aqueous uranyl acetate and two minutes with 1% $KMnO_4$ to selectively stain for lignins. Micrographs were captured with a four mega-pixel Gatan UltraScan 1000 camera (Gatan, Pleasanton, Calif.) on a FEI Tecnai G2 20 Twin 200 kV LaB6 TEM (FEI, Hilsboro, Oreg.).

Image Analysis—

Fiji (ImageJ) was used to rotate, crop, resize, and adjust contrast, brightness and white balance of images and to threshold images to aid in positively identifying gold nano-particles for quantitation.

Crystallinity Studies

We have also compared the C1 and C3 constructs on differential crystallinity materials. CelA is agnostic to cellulose crystallinity. C1 and C3 were tested on a high (66%) and low crystallinity (33%) substrates generated from cotton linters (see FIG. 18). The C3 construct is more effective on both the 66% and 33% crystallinity substrates. However, the impact of the higher crystallinity material is very clear in both the C1 and C3 cases, therefore we can conclude that we have not been able to "recapitulate" the crystalline agnostic property observed with CelA, where both the 66% and 33% materials converted equally well.

QCMD Experiments

QCMD experiments measure changes in both frequency and changes in dissipation, the change in frequency is inversely proportional to changes in mass, and therefore a positive change in the curve is equal to a decrease in mass, and a negative change in frequency corresponds to a increase in mass. All experiments were run in a high concentration of cellobiose (10 mM) to prevent catalytic action on the substrate.

As seen in FIG. 20, C3 raptor binds very rapidly and has a similar off rate (buffer wash started at 80 min) when compared to the C1 construct (C2 construct is similar to C1 and data is not shown). However, the C3 construct appears to loose mass in a non-catalytic manner when compared to C1 (rising curve before buffer rinse).

Furthermore, QCMD can measure changes in dissipation which are proportional to the "softness" of the material. In the case of the C3 construct we see a strong increase in the softness of the material when compared to the C1 construct or any other of the constructs tested. This novel property is one we have never before observed for any other cellulase and is unique to the C3 construct (FIG. 19). This novel mechanism may also account for the improved performance of the C3 construct.

One of the novel findings is that the C3 (Cel7a-CBM3-Cel5a) multifunctional construct has a significantly higher binding rate to cellulose, which may be partly responsible for its improved activity when compared to other constructs. Interestingly the other C1 (Cel7a-CBM1-Cel5a), and C2 (Cel7a-Link-Cel5a) constructs tested previously still perform as well as the pfCel7a module which has higher binding affinity than the multifunctionals.

Disclosed herein are improved multifunctional enzymes, such as Cel7a-CBM3-Cel5a (C3). Multifunctionals can be successfully engineered to work in fungal expression systems. They can have activity superior to that of their component enzymes (see FIG. 16). We have also discovered that there is a unique cellulose deconstruction mechanism that occurs with the CBM3 containing enzyme system. Moreover, this mechanism appears to be distinct from enzymes such as CelA.

When considering designing multifunctional enzymes, emergent properties of these systems cannot easily be predicted. Proximity synergy does not appear to confer much benefit to the Cel7A-CBM1-Cel5A or Cel7A-Link-Cel5A enzymes when compared to the binary free enzyme mixture of Ce17 and Ce15. However, a significant improvement is observed when the CBM3 is added in the case of the multifunctional. However, merely adding a CBM3 to Cel7A does not grant any improvement in the performance; rather, the opposite is seen in the case of the Cel7A-CBM3 construct. The activity and performance of the Cel7A-CBM3-Cel5A enzyme exhibits an unexpected synergistic improvement.

The Cel7A-CBM3-Cel5A enzyme does seem to bind Avicel a bit more tightly than the other multifunctional enzymes, and about as well as the native Cel7A-CBM1 system, however binding alone is unlikely to explain this enhancement in performance.

The QCM data provides us with the best evidence that something unique is occurring with the Cel7A-CBM3-Cel5A enzyme. Regardless of the domain composition of the other enzymes tested the combination of the CBM3 domain with the Cel5A and Cel7A domains appears to soften the cellulose surface as well as non-catalytically removed cellulose from the surface of the sensor.

We claim:

1. A non-naturally occurring enzyme having greater than 85% identity to SEQ ID NO: 6 and having greater than 50% reduction in conversion time for a glucan substrate when compared to a naturally occurring enzyme.

2. An isolated nucleic acid encoding a non-naturally occurring enzyme and having greater than 85% identity to SEQ ID NO: 5 wherein the enzyme has greater than 50% reduction in conversion time for a glucan substrate when compared to a naturally occurring enzyme.

3. The isolated nucleic acid molecule of claim 2, further comprising a promoter operably linked to the nucleic acid molecule.

4. The isolated nucleic acid molecule of claim 3, wherein the promoter allows expression of the nucleic acid in a filamentous fungal host cell.

5. An expression vector comprising the nucleic acid molecule of claim 2.

6. A host cell comprising the expression vector of claim 5 and expressing a recombinant polypeptide encoded by the nucleic acid molecule.

7. The host cell of claim 6, wherein the cell is a fungal cell.

8. An isolated enzyme polypeptide encoded by the nucleic acid molecule according to claim 2.

9. A method for degrading cellulose or lignocellulosic biomass, comprising contacting the cellulose or lignocellulosic biomass with the enzyme according to claim 1.

10. The method of claim 9 wherein the cellulose is degraded by the enzyme in about 50% of the time that it takes the isolated enzymes that comprise the enzyme to degrade the cellulose.

11. A method for producing a biofuel from lignocellulosic biomass, comprising:
a) contacting the lignocellulosic biomass with an enzyme according to claim 1 to generate sugars; and
b) converting the sugars to a biofuel by fermentation.

* * * * *

SEQUENCE LISTING

<160> NUMBER OF SEQ ID NOS: 6

<210> SEQ ID NO 1
<211> LENGTH: 2811
<212> TYPE: DNA
<213> ORGANISM: Artificial Sequence
<220> FEATURE:
<223> OTHER INFORMATION: Sequence is synthesized

<400> SEQUENCE: 1

| | | | | | |
|---|---|---|---|---|---|
| atgtctgcct | tgaactcttt | caatatgtac | aagagcgccc | tcatcttggg | ctccttgctg | 60 |
| gcaacagctg | gtgctcagca | aattggtact | tataccgctg | aaacccatcc | ctctctgagc | 120 |
| tggtctactt | gcaaatcggg | tggtagctgc | accacaaact | ccggtgccat | tacgttagat | 180 |
| gccaactggc | gttgggtcca | tggtgtcaat | accagcacca | actgctacac | tggcaacact | 240 |
| tggaatagcg | ccatctgcga | cactgatgca | tcctgtgccc | aggactgtgc | tctcgatggt | 300 |
| gctgactact | ctggcacgta | cggtatcact | acctccggca | actcattgcg | cctgaacttc | 360 |
| gttaccggtt | ccaacgtcgg | atctcgtact | tacctgatgg | ccgataacac | ccactaccaa | 420 |
| atcttcgatc | tgttgaacca | ggagttcacc | ttcaccgtcg | atgtctccca | cctcccttgc | 480 |
| ggtttgaacg | gtgccctcta | cttcgtgacc | atggatgccg | acggtggcgt | ctccaagtac | 540 |
| cccaacaaca | aggccggtgc | tcagtacggt | gttggatact | gtgactctca | atgccctcgt | 600 |
| gacttgaagt | tcatcgctgg | tcaggccaac | gttgagggct | ggacgccctc | cgccaacaac | 660 |
| gccaacactg | gaattggcaa | tcacggagct | tgctgcgcgg | agcttgatat | ctgggaggca | 720 |
| aacagcatct | cagaggcctt | gactcctcac | ccttgcgata | cacccggtct | atctgtttgc | 780 |
| actactgatg | cctgcggtgg | tacctacagc | tctgatcgtt | acgccggtac | ctgcgaccct | 840 |
| gatggatgtg | acttcaaccc | ttaccgcctt | ggtgtcactg | acttctacgg | ctccggcaag | 900 |
| accgttgaca | ccaccaagcc | ctttaccgtt | gtgactcaat | tcgtcactaa | cgacggtacc | 960 |
| tccaccggtt | ccctctccga | gatcagacgt | tactacgttc | agaacggcgt | tgtcatcccc | 1020 |
| cagccttcct | ccaagatctc | cggaatcagc | ggaaatgtca | tcaactccga | ctactgcgct | 1080 |
| gctgaaattt | ccacctttgg | cgggactgcc | tccttcagca | aacacggtgg | cttgacaaac | 1140 |
| atggccgctg | gtatggaagc | tggtatggtc | ttggtcatga | gtttgtggga | cgactacgcc | 1200 |
| gtcaacatgc | tctggctcga | cagcacctac | cctacaaacg | cgactggtac | ccccggtgcc | 1260 |
| gctcgtggta | cctgcgctac | cacttctggg | gaccccaaga | ccgttgaatc | acaatccggc | 1320 |
| agctcctatg | tcaccttctc | tgacattcgg | gttggtcctt | tcaattctac | gttcagcggt | 1380 |
| ggttctagca | ccgtggcag | cactactact | accgccagcc | gcaccaccac | cacctcggcc | 1440 |
| tcttccacct | ctacttccag | cacctctact | ggcactggag | gatccgtcgc | tggtcactgg | 1500 |
| ggtcagtgtg | gtggccaggg | ctggactggc | cctaccacct | gtgttagtgg | aaccacatgc | 1560 |
| accgtcgtga | acccttacta | ctctcaatgt | ttgggcgctg | caagctcaag | ctcgtccacg | 1620 |
| cgcgccgcgt | cgacgacttc | tcgagtatcc | cccacaacat | cccggtcgag | ctccgcgacg | 1680 |
| cctccacctg | gttctactac | taccagagta | cctccagtcg | gatcgggaaa | gctggctggc | 1740 |
| ggcggctact | ggcacacctc | cggtcgcgag | atactcgacg | caaataatgt | tcctgtccga | 1800 |
| atcgcgggga | ttaactggtt | cggattcgag | acgtgcaatt | acgttgtcca | tggcctttgg | 1860 |
| tcccgagatt | accgctcaat | gctcgaccag | atcaagtcgc | tcggttacaa | cacgattcgt | 1920 |
| ctaccgtatt | ctgacgacat | ccttaagccc | ggcaccatgc | caaatagcat | caatttttac | 1980 |
| caaatgaacc | aagacctgca | ggggcttact | tccctgcagg | tgatggacaa | gatcgttgcc | 2040 |

-continued

```
tacgccggcc agatcggact gcgtatcatc ctggaccgcc accggccgga ctgcagcggc    2100
cagtcggcct tgtggtacac gagcagcgtt tcggaggcca catggatttc cgacctgcag    2160
gctttggccc agcgctacaa gggaaaccca actgtcgtag gcttcgacct ccacaacgag    2220
ccccacgacc ccgcatgctg gggatgcggc gatccgtcga ttgactggag gctcgctgcc    2280
gaacgtgctg gtaacgctgt cttgtccgtg aacccaaacc ttctgatctt cgtcgaaggc    2340
gttcagtctt acaatggaga ttcgtactgg tggggcggaa accttcaggg cgctggccaa    2400
tacccggtcg ttctcaacgt tccgaaccgg cttgtttaca gcgcacacga ctacgccacg    2460
agcgtcggcc ctcaaacctg gttctccgac cctacattcc caacaacat gccaggaatc    2520 tggaacaaga attggggcta ccttttcaac cagaacatcg ctcccgtttg gctgggcgag    2580
tttggcacaa cgttgcagtc tacgacggac caaacatggc tgaagaccct cgtccagtat    2640
ctcaggccca ccgcgcagta tggtgcggac agctttcagt ggaccttctg gtcttggaac    2700
cccgattctg gcgacacagg cggtatcctg aaggatgatt ggcagacggt tgacacagtc    2760
aaggacggtt atctggcacc tatcaagtcc agcatcttcg accccgttta a              2811
```

<210> SEQ ID NO 2
<211> LENGTH: 936
<212> TYPE: PRT
<213> ORGANISM: Artificial Sequence
<220> FEATURE:
<223> OTHER INFORMATION: Sequence is synthesized

<400> SEQUENCE: 2

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Ser Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ala Asn Asn Ala Asn Thr Gly
    210                 215                 220
```

```
Ile Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
            245                 250                 255

Leu Ser Val Cys Thr Thr Asp Ala Cys Gly Thr Tyr Ser Ser Asp
        260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
290                 295                 300

Thr Lys Pro Phe Thr Val Val Thr Gln Phe Val Thr Asn Asp Gly Thr
305                 310                 315                 320

Ser Thr Gly Ser Leu Ser Glu Ile Arg Arg Tyr Tyr Val Gln Asn Gly
            325                 330                 335

Val Val Ile Pro Gln Pro Ser Ser Lys Ile Ser Gly Ile Ser Gly Asn
            340                 345                 350

Val Ile Asn Ser Asp Tyr Cys Ala Ala Glu Ile Ser Thr Phe Gly Gly
            355                 360                 365

Thr Ala Ser Phe Ser Lys His Gly Gly Leu Thr Asn Met Ala Ala Gly
        370                 375                 380

Met Glu Ala Gly Met Val Leu Val Met Ser Leu Trp Asp Asp Tyr Ala
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Thr Cys Ala Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
        450                 455                 460

Gly Gly Ser Thr Thr Thr Ala Ser Arg Thr Thr Thr Thr Ser Ala
465                 470                 475                 480

Ser Ser Thr Ser Thr Ser Ser Thr Ser Thr Gly Thr Gly Gly Ser Val
            485                 490                 495

Ala Gly His Trp Gly Gln Cys Gly Gly Gln Gly Trp Thr Gly Pro Thr
        500                 505                 510

Thr Cys Val Ser Gly Thr Thr Cys Thr Val Val Asn Pro Tyr Tyr Ser
        515                 520                 525

Gln Cys Leu Gly Ala Ala Ser Ser Ser Ser Thr Arg Ala Ala Ser
530                 535                 540

Thr Thr Ser Arg Val Ser Pro Thr Thr Ser Arg Ser Ser Ser Ala Thr
545                 550                 555                 560

Pro Pro Pro Gly Ser Thr Thr Thr Arg Val Pro Val Gly Ser Gly
                565                 570                 575

Lys Leu Ala Gly Gly Gly Tyr Trp His Thr Ser Gly Arg Glu Ile Leu
            580                 585                 590

Asp Ala Asn Asn Val Pro Val Arg Ile Ala Gly Ile Asn Trp Phe Gly
        595                 600                 605

Phe Glu Thr Cys Asn Tyr Val Val His Gly Leu Trp Ser Arg Asp Tyr
        610                 615                 620

Arg Ser Met Leu Asp Gln Ile Lys Ser Leu Gly Tyr Asn Thr Ile Arg
625                 630                 635                 640

Leu Pro Tyr Ser Asp Asp Ile Leu Lys Pro Gly Thr Met Pro Asn Ser
```

-continued

```
            645                 650                 655
Ile Asn Phe Tyr Gln Met Asn Gln Asp Leu Gln Gly Leu Thr Ser Leu
            660                 665                 670

Gln Val Met Asp Lys Ile Val Ala Tyr Ala Gly Gln Ile Gly Leu Arg
            675                 680                 685

Ile Ile Leu Asp Arg His Arg Pro Asp Cys Ser Gly Gln Ser Ala Leu
    690                 695                 700

Trp Tyr Thr Ser Val Ser Glu Ala Thr Trp Ile Ser Asp Leu Gln
705                 710                 715                 720

Ala Leu Ala Gln Arg Tyr Lys Gly Asn Pro Thr Val Val Gly Phe Asp
                725                 730                 735

Leu His Asn Glu Pro His Asp Pro Ala Cys Trp Gly Cys Gly Asp Pro
            740                 745                 750

Ser Ile Asp Trp Arg Leu Ala Ala Glu Arg Ala Gly Asn Ala Val Leu
            755                 760                 765

Ser Val Asn Pro Asn Leu Leu Ile Phe Val Glu Gly Val Gln Ser Tyr
    770                 775                 780

Asn Gly Asp Ser Tyr Trp Trp Gly Gly Asn Leu Gln Gly Ala Gly Gln
785                 790                 795                 800

Tyr Pro Val Val Leu Asn Val Pro Asn Arg Leu Val Tyr Ser Ala His
                805                 810                 815

Asp Tyr Ala Thr Ser Val Gly Pro Gln Thr Trp Phe Ser Asp Pro Thr
            820                 825                 830

Phe Pro Asn Asn Met Pro Gly Ile Trp Asn Lys Asn Trp Gly Tyr Leu
            835                 840                 845

Phe Asn Gln Asn Ile Ala Pro Val Trp Leu Gly Glu Phe Gly Thr Thr
    850                 855                 860

Leu Gln Ser Thr Thr Asp Gln Thr Trp Leu Lys Thr Leu Val Gln Tyr
865                 870                 875                 880

Leu Arg Pro Thr Ala Gln Tyr Gly Ala Asp Ser Phe Gln Trp Thr Phe
                885                 890                 895

Trp Ser Trp Asn Pro Asp Ser Gly Asp Thr Gly Gly Ile Leu Lys Asp
            900                 905                 910

Asp Trp Gln Thr Val Asp Thr Val Lys Asp Gly Tyr Leu Ala Pro Ile
            915                 920                 925

Lys Ser Ser Ile Phe Asp Pro Val
    930                 935

<210> SEQ ID NO 3
<211> LENGTH: 2703
<212> TYPE: DNA
<213> ORGANISM: Artificial Sequence
<220> FEATURE:
<223> OTHER INFORMATION: Sequence is synthesized.

<400> SEQUENCE: 3
atgtctgcct tgaactcttt caatatgtac aagagcgccc tcatcttggg ctccttgctg      60
gcaacagctg gtgctcagca aattggtact tataccgctg aaacccatcc ctctctgagc     120
tggtctactt gcaaatcggg tggtagctgc accacaaact ccgtgccat acgttagat       180 gccaactggc gttgggtcca tggtgtcaat accagcacca actgctacac tggcaacact     240
tggaatagcg ccatctgcga cactgatgca tcctgtgccc aggactgtgc tctcgatggt     300
gctgactact ctggcacgta cggtatcact acctccggca actcattgcg cctgaacttc     360
gttaccggtt ccaacgtcgg atctcgtact tacctgatgg ccgataacac ccactaccaa     420
```

```
atcttcgatc tgttgaacca ggagttcacc ttcaccgtcg atgtctccca cctcccttgc    480
ggtttgaacg gtgccctcta cttcgtgacc atggatgccg acggtggcgt ctccaagtac    540
cccaacaaca aggccggtgc tcagtacggt gttggatact gtgactctca atgccctcgt    600
gacttgaagt tcatcgctgg tcaggccaac gttgagggcg gacgccctc cgccaacaac     660 gccaacactg gaattggcaa tcacggagct tgctgcgcgg agcttgatat ctgggaggca    720
aacagcatct cagaggcctt gactcctcac ccttgcgata cacccggtct atctgtttgc    780
actactgatg cctgcggtgg tacctacagc tctgatcgtt acgccggtac ctgcgaccct    840
gatggatgtg acttcaaccc ttaccgcctt ggtgtcactg acttctacgg ctccggcaag    900
accgttgaca ccaccaagcc ctttaccgtt gtgactcaat cgtcactaa cgacggtacc     960 tccaccggtt ccctctccga gatcagacgt tactacgttc agaacggcgt tgtcatcccc   1020
cagccttcct ccaagatctc cggaatcagc ggaaatgtca tcaactccga ctactgcgct   1080
gctgaaattt ccacctttgg cgggactgcc tccttcagca acacggtgg cttgacaaac    1140 atggccgctg gtatggaagc tggtatggtc ttggtcatga gtttgtggga cgactacgcc   1200
gtcaacatgc tctggctcga cagcacctac cctacaaacg cgactggtac ccccggtgcc   1260
gctcgtggta cctgcgctac cacttctggg accccaaga ccgttgaatc acaatccggc    1320
agctcctatg tcaccttctc tgacattcgg gttggtcctt tcaattctac gttcagcggt   1380
ggttctagca ccggtggcag cactactact accgccagcc gcaccaccac cacctcggcc   1440
tcttccacct ctacttccag cacctctact ggcactggag gatccggcgc tgcaagctca   1500
agctcgtcca cgcgcgccgc gtcgacgact tctcgagtat ccccacaac atcccggtcg    1560 agctccgcga cgcctccacc tggttctact actaccagag tacctccagt cggatcggga   1620
aagctggctg gcggcggcta ctggcacacc tccggtcgcg agatactcga cgcaaataat   1680
gttcctgtcc gaatcgcggg gattaactgg ttcggattcg agacgtgcaa ttacgttgtc   1740
catggccttt ggtcccgaga ttaccgctca atgctcgacc agatcaagtc gctcggttac   1800
aacacgattc gtctaccgta ttctgacgac atccttaagc ccggcaccat gccaaatagc   1860
atcaattttt accaaatgaa ccaagacctg cagggcttta cttccctgca ggtgatggac   1920
aagatcgttg cctacgccgg ccagatcgga ctgcgtatca tcctggaccg ccaccggccg   1980
gactgcagcg gccagtcggc cttgtggtac acgagcagcg tttcggaggc cacatggatt   2040
tccgacctgc aggctttggc ccagcgctac aagggaaacc caactgtcgt aggcttcgac   2100
ctccacaacg agccccacga ccccgcatgc tggggatgcg gcgatccgtc gattgactgg   2160
aggctcgctg ccgaacgtgc tggtaacgct gtcttgtccg tgaacccaaa ccttctgatc   2220
ttcgtcgaag gcgttcagtc ttacaatgga gattcgtact ggtggggcgg aaaccttcag   2280
ggcgctggcc aatacccggt cgttctcaac gttccgaacc ggcttgttta cagcgcacac   2340
gactacgcca cgagcgtcgg ccctcaaacc tggttctccg accctacatt ccccaacaac   2400
atgccaggaa tctgaacaa gaattggggc tacctttca accagaacat cgctcccgtt     2460
tggctgggcg agtttggcac aacgttgcag tctacgacgg accaaacatg gctgaagacc   2520
ctcgtccagt atctcaggcc caccgcgcag tatggtgcgc acagctttca gtggaccttc   2580
tggtcttgga accccgattc tggcgacaca ggcggtatcc tgaaggatga ttggcagacg   2640
gttgacacag tcaaggacgg ttatctggca cctatcaagt ccagcatctt cgaccccgtt   2700
taa                                                                 2703
```

<210> SEQ ID NO 4
<211> LENGTH: 900
<212> TYPE: PRT
<213> ORGANISM: Artificial Sequence
<220> FEATURE:
<223> OTHER INFORMATION: Sequence is synthesized.

<400> SEQUENCE: 4

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
                20                  25                  30

Ala Glu Thr His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Ser Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ala Asn Asn Ala Asn Thr Gly
    210                 215                 220

Ile Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Phe Thr Val Val Thr Gln Phe Val Thr Asn Asp Gly Thr
305                 310                 315                 320

Ser Thr Gly Ser Leu Ser Glu Ile Arg Arg Tyr Tyr Val Gln Asn Gly
                325                 330                 335

Val Val Ile Pro Gln Pro Ser Ser Lys Ile Ser Gly Ile Ser Gly Asn
            340                 345                 350

Val Ile Asn Ser Asp Tyr Cys Ala Ala Glu Ile Ser Thr Phe Gly Gly
        355                 360                 365
```

```
Thr Ala Ser Phe Ser Lys His Gly Gly Leu Thr Asn Met Ala Ala Gly
    370                 375                 380
Met Glu Ala Gly Met Val Leu Val Met Ser Leu Trp Asp Asp Tyr Ala
385                 390                 395                 400
Val Asn Met Leu Trp Leu Asp Ser Thr Tyr Pro Thr Asn Ala Thr Gly
                405                 410                 415
Thr Pro Gly Ala Ala Arg Gly Thr Cys Ala Thr Thr Ser Gly Asp Pro
                420                 425                 430
Lys Thr Val Glu Ser Gln Ser Gly Ser Ser Tyr Val Thr Phe Ser Asp
                435                 440                 445
Ile Arg Val Gly Pro Phe Asn Ser Thr Phe Ser Gly Gly Ser Ser Thr
    450                 455                 460
Gly Gly Ser Thr Thr Thr Thr Ala Ser Arg Thr Thr Thr Thr Ser Ala
465                 470                 475                 480
Ser Ser Thr Ser Thr Ser Ser Thr Ser Thr Gly Thr Gly Gly Ser Gly
                485                 490                 495
Ala Ala Ser Ser Ser Ser Ser Thr Arg Ala Ala Ser Thr Thr Ser Arg
                500                 505                 510
Val Ser Pro Thr Thr Ser Arg Ser Ser Ser Ala Thr Pro Pro Pro Gly
    515                 520                 525
Ser Thr Thr Thr Arg Val Pro Pro Val Gly Ser Gly Lys Leu Ala Gly
    530                 535                 540
Gly Gly Tyr Trp His Thr Ser Gly Arg Glu Ile Leu Asp Ala Asn Asn
545                 550                 555                 560
Val Pro Val Arg Ile Ala Gly Ile Asn Trp Phe Gly Phe Glu Thr Cys
                565                 570                 575
Asn Tyr Val Val His Gly Leu Trp Ser Arg Asp Tyr Arg Ser Met Leu
                580                 585                 590
Asp Gln Ile Lys Ser Leu Gly Tyr Asn Thr Ile Arg Leu Pro Tyr Ser
                595                 600                 605
Asp Asp Ile Leu Lys Pro Gly Thr Met Pro Asn Ser Ile Asn Phe Tyr
    610                 615                 620
Gln Met Asn Gln Asp Leu Gln Gly Leu Thr Ser Leu Gln Val Met Asp
625                 630                 635                 640
Lys Ile Val Ala Tyr Ala Gly Gln Ile Gly Leu Arg Ile Ile Leu Asp
                645                 650                 655
Arg His Arg Pro Asp Cys Ser Gly Gln Ser Ala Leu Trp Tyr Thr Ser
                660                 665                 670
Ser Val Ser Glu Ala Thr Trp Ile Ser Asp Leu Gln Ala Leu Ala Gln
                675                 680                 685
Arg Tyr Lys Gly Asn Pro Thr Val Val Gly Phe Asp Leu His Asn Glu
    690                 695                 700
Pro His Asp Pro Ala Cys Trp Gly Cys Gly Asp Pro Ser Ile Asp Trp
705                 710                 715                 720
Arg Leu Ala Ala Glu Arg Ala Gly Asn Ala Val Leu Ser Val Asn Pro
                725                 730                 735
Asn Leu Leu Ile Phe Val Glu Gly Val Gln Ser Tyr Asn Gly Asp Ser
                740                 745                 750
Tyr Trp Trp Gly Gly Asn Leu Gln Gly Ala Gly Gln Tyr Pro Val Val
                755                 760                 765
Leu Asn Val Pro Asn Arg Leu Val Tyr Ser Ala His Asp Tyr Ala Thr
    770                 775                 780
Ser Val Gly Pro Gln Thr Trp Phe Ser Asp Pro Thr Phe Pro Asn Asn
```

```
                785              790                795              800
Met Pro Gly Ile Trp Asn Lys Asn Trp Gly Tyr Leu Phe Asn Gln Asn
                    805              810                815

Ile Ala Pro Val Trp Leu Gly Glu Phe Gly Thr Thr Leu Gln Ser Thr
                820              825                830

Thr Asp Gln Thr Trp Leu Lys Thr Leu Val Gln Tyr Leu Arg Pro Thr
                    835              840                845

Ala Gln Tyr Gly Ala Asp Ser Phe Gln Trp Thr Phe Trp Ser Trp Asn
    850              855                860

Pro Asp Ser Gly Asp Thr Gly Gly Ile Leu Lys Asp Trp Gln Thr
865              870                875                880

Val Asp Thr Val Lys Asp Gly Tyr Leu Ala Pro Ile Lys Ser Ser Ile
                    885              890                895

Phe Asp Pro Val
            900

<210> SEQ ID NO 5
<211> LENGTH: 3174
<212> TYPE: DNA
<213> ORGANISM: Artificial Sequence
<220> FEATURE:
<223> OTHER INFORMATION: Sequence is synthesized.

<400> SEQUENCE: 5
atgtctgcct tgaactcttt caatatgtac aagagcgccc tcatcttggg ctccttgctg       60
gcaacagctg gtgctcagca aattggtact tataccgctg aaacccatcc ctctctgagc      120
tggtctactt gcaaatcggg tggtagctgc accacaaact ccggtgccat acgttagat       180 gccaactggc gttgggtcca tggtgtcaat accagcacca actgctacac tggcaacact      240
tggaatagcg ccatctgcga cactgatgca tcctgtgccc aggactgtgc tctcgatggt      300
gctgactact ctggcacgta cggtatcact acctccggca actcattgcg cctgaacttc      360
gttaccggtt ccaacgtcgg atctcgtact tacctgatgg ccgataacac ccactaccaa      420
atcttcgatc tgttgaacca ggagttcacc ttcaccgtcg atgtctccca cctcccttgc      480
ggtttgaacg gtgccctcta cttcgtgacc atggatgccg acggtggcgt ctccaagtac      540
cccaacaaca aggccggtgc tcagtacggt gttggatact gtgactctca atgccctcgt      600
gacttgaagt tcatcgctgg tcaggccaac gttgagggc ggacgccctc cgccaacaac      660
gccaacactg gaattggcaa tcacggagct tgctgcgcgg agcttgatat ctgggaggca      720
aacagcatct cagaggcctt gactcctcac ccttgcgata cacccggtct atctgtttgc      780
actactgatg cctgcggtgg tacctacagc tctgatcgtt acgccggtac ctgcgaccct      840
gatggatgtg acttcaaccc ttaccgcctt ggtgtcactg acttctacgg ctccggcaag      900
accgttgaca ccaccaagcc ctttaccgtt gtgactcaat cgtcactaa cgacggtacc      960 tccaccggtt ccctctccga gatcagacgt tactacgttc agaacggcgt tgtcatcccc     1020
cagccttcct ccaagatctc cggaatcagc ggaaatgtca tcaactccga ctactgcgct     1080
gctgaaattt ccacctttgg cgggactgcc tccttcagca aacacggtgg cttgacaaac     1140
atggccgctg gtatggaagc tggtatggtc ttggtcatga gtttgtggga cgactacgcc     1200
gtcaacatgc tctggctcga cagcacctac cctacaaacg cgactggtac ccccggtgcc     1260
gctcgtggta cctgcgctac cacttctggg gaccccaaga ccgttgaatc acaatccggc     1320
agctcctatg tcaccttctc tgacattcgg gttggtcctt tcaattctac gttcagcggt     1380
```

```
ggttctagca ccggtggcag cactactact accgccagcc gcaccaccac cacctcggcc    1440
tcttccacct ctacttccag cacctctact ggcactggag gatccgttgc aggtggacag    1500
attaaagtgc tctatgcaaa taaggaaacc aattcaacaa cgaacacgat tcgcccgtgg    1560
ctgaaagtcg tgaatacggg gtccagttca atcgatctct cccgcgtcac tatccgctac    1620
tggtacaccg tagatggcga taaagcacaa tccgcaattt cggattgggc ccagatcggt    1680
gctagcaacg taacttttaa atttgtcaag ctgagtagcc cggttagtgg ggccgactat    1740
tatctggaga tcggtttcaa aagtggagcc ggccagctcc aggccggtaa agacacggga    1800
gaaatacaga tccgctttaa taaatccgac tggagcaatt ataaccaggg gaacgattgg    1860
agctggatgc aatccatgac ctcttacggt gaaaatgtaa aggtcaccgc atatatagat    1920
ggcgtactcg tctggggcca agaaccttcc ggagcgggcg ctgcaagctc aagctcgtcc    1980
acgcgcgccg cgtcgacgac ttctcgagta tcccccacaa catcccggtc gagctccgcg    2040
acgcctccac ctggttctac tactaccaga gtacctccag tcggatcggg aaagctggct    2100
ggcggcggct actggcacac ctccggtcgc gagatactcg acgcaaataa tgttcctgtc    2160
cgaatcgcgg ggattaactg gttcggattc gagacgtgca attacgttgt ccatggcctt    2220
tggtcccgag attaccgctc aatgctcgac cagatcaagt cgctcggtta caacacgatt    2280
cgtctaccgt attctgacga catccttaag cccggcacca tgccaaatag catcaatttt    2340
taccaaatga accaagacct gcaggggctt acttccctgc aggtgatgga caagatcgtt    2400
gcctacgccg ccagatcgg actgcgtatc atcctggacc gccaccggcc ggactgcagc    2460
ggccagtcgg ccttgtggta cacgagcagc gtttcggagg ccacatggat ttccgacctg    2520
caggctttgg cccagcgcta aagggaaac ccaactgtcg taggcttcga cctccacaac    2580
gagccccacg accccgcatg ctggggatgc ggcgatccgt cgattgactg gaggctcgct    2640
gccgaacgtg ctggtaacgc tgtcttgtcc gtgaacccaa accttctgat cttcgtcgaa    2700
ggcgttcagt cttacaatgg agattcgtac tggtggggcg gaaaccttca gggcgctggc    2760
caatacccgg tcgttctcaa cgttccgaac cggcttgttt acagcgcaca cgactacgcc    2820
acgagcgtcg gccctcaaac ctggttctcc gaccctacat tccccaacaa catgccagga    2880
atctggaaca agaattgggg ctacctttc aaccagaaca tcgctcccgt ttggctgggc    2940
gagtttggca aacgttgca gtctacgacg gaccaaacat ggctgaagac cctcgtccag    3000
tatctcaggc ccaccgcgca gtatggtgcg gacagctttc agtggacctt ctggtcttgg    3060
aaccccgatt ctggcgacac aggcggtatc ctgaaggatg attggcagac ggttgacaca    3120
gtcaaggacg gttatctggc acctatcaag tccagcatct cgaccccgt ttaa           3174
```

<210> SEQ ID NO 6
<211> LENGTH: 1057
<212> TYPE: PRT
<213> ORGANISM: Artificial Sequence
<220> FEATURE:
<223> OTHER INFORMATION: Sequence is synthesized.

<400> SEQUENCE: 6

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45
```

-continued

```
Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
 65                  70                  75                  80

Trp Asn Ser Ala Ile Cys Asp Thr Asp Ala Ser Cys Ala Gln Asp Cys
                 85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ala Asn Asn Ala Asn Thr Gly
    210                 215                 220

Ile Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Phe Thr Val Val Thr Gln Phe Val Thr Asn Asp Gly Thr
305                 310                 315                 320

Ser Thr Gly Ser Leu Ser Glu Ile Arg Arg Tyr Tyr Val Gln Asn Gly
                325                 330                 335

Val Val Ile Pro Gln Pro Ser Ser Lys Ile Ser Gly Ile Ser Gly Asn
            340                 345                 350

Val Ile Asn Ser Asp Tyr Cys Ala Ala Glu Ile Ser Thr Phe Gly Gly
        355                 360                 365

Thr Ala Ser Phe Ser Lys His Gly Gly Leu Thr Asn Met Ala Ala Gly
    370                 375                 380

Met Glu Ala Gly Met Val Leu Val Met Ser Leu Trp Asp Asp Tyr Ala
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Thr Cys Ala Thr Thr Ser Gly Asp Pro
            420                 425                 430

Lys Thr Val Glu Ser Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
    450                 455                 460

Gly Gly Ser Thr Thr Thr Thr Ala Ser Arg Thr Thr Thr Thr Ser Ala
```

```
                465                 470                 475                 480
        Ser Ser Thr Ser Thr Ser Ser Thr Ser Thr Gly Thr Gly Gly Ser Val
                        485                 490                 495

Ala Gly Gly Gln Ile Lys Val Leu Tyr Ala Asn Lys Glu Thr Asn Ser
                        500                 505                 510

Thr Thr Asn Thr Ile Arg Pro Trp Leu Lys Val Val Asn Thr Gly Ser
                        515                 520                 525

Ser Ser Ile Asp Leu Ser Arg Val Thr Ile Arg Tyr Trp Tyr Thr Val
                        530                 535                 540

Asp Gly Asp Lys Ala Gln Ser Ala Ile Ser Asp Trp Ala Gln Ile Gly
        545                 550                 555                 560

Ala Ser Asn Val Thr Phe Lys Phe Val Lys Leu Ser Ser Ser Val Ser
                        565                 570                 575

Gly Ala Asp Tyr Tyr Leu Glu Ile Gly Phe Lys Ser Gly Ala Gly Gln
                        580                 585                 590

Leu Gln Ala Gly Lys Asp Thr Gly Glu Ile Gln Ile Arg Phe Asn Lys
                        595                 600                 605

Ser Asp Trp Ser Asn Tyr Asn Gln Gly Asn Asp Trp Ser Trp Met Gln
                        610                 615                 620

Ser Met Thr Ser Tyr Gly Glu Asn Val Lys Val Thr Ala Tyr Ile Asp
        625                 630                 635                 640

Gly Val Leu Val Trp Gly Gln Glu Pro Ser Gly Ala Gly Ala Ala Ser
                        645                 650                 655

Ser Ser Ser Ser Thr Arg Ala Ala Ser Thr Thr Ser Arg Val Ser Pro
                        660                 665                 670

Thr Thr Ser Arg Ser Ser Ala Thr Pro Pro Gly Ser Thr Thr
                        675                 680                 685

Thr Arg Val Pro Pro Val Gly Ser Gly Lys Leu Ala Gly Gly Gly Tyr
                        690                 695                 700

Trp His Thr Ser Gly Arg Glu Ile Leu Asp Ala Asn Asn Val Pro Val
        705                 710                 715                 720

Arg Ile Ala Gly Ile Asn Trp Phe Gly Phe Glu Thr Cys Asn Tyr Val
                        725                 730                 735

Val His Gly Leu Trp Ser Arg Asp Tyr Arg Ser Met Leu Asp Gln Ile
                        740                 745                 750

Lys Ser Leu Gly Tyr Asn Thr Ile Arg Leu Pro Tyr Ser Asp Asp Ile
                        755                 760                 765

Leu Lys Pro Gly Thr Met Pro Asn Ser Ile Asn Phe Tyr Gln Met Asn
        770                 775                 780

Gln Asp Leu Gln Gly Leu Thr Ser Leu Gln Val Met Asp Lys Ile Val
        785                 790                 795                 800

Ala Tyr Ala Gly Gln Ile Gly Leu Arg Ile Ile Leu Asp Arg His Arg
                        805                 810                 815

Pro Asp Cys Ser Gly Gln Ser Ala Leu Trp Tyr Thr Ser Ser Val Ser
                        820                 825                 830

Glu Ala Thr Trp Ile Ser Asp Leu Gln Ala Leu Ala Gln Arg Tyr Lys
                        835                 840                 845

Gly Asn Pro Thr Val Val Gly Phe Asp Leu His Asn Glu Pro His Asp
                        850                 855                 860

Pro Ala Cys Trp Gly Cys Gly Asp Pro Ser Ile Asp Trp Arg Leu Ala
        865                 870                 875                 880

Ala Glu Arg Ala Gly Asn Ala Val Leu Ser Val Asn Pro Asn Leu Leu
                        885                 890                 895
```

-continued

```
Ile Phe Val Glu Gly Val Gln Ser Tyr Asn Gly Asp Ser Tyr Trp Trp
            900                 905                 910

Gly Gly Asn Leu Gln Gly Ala Gly Gln Tyr Pro Val Val Leu Asn Val
        915                 920                 925

Pro Asn Arg Leu Val Tyr Ser Ala His Asp Tyr Ala Thr Ser Val Gly
    930                 935                 940

Pro Gln Thr Trp Phe Ser Asp Pro Thr Phe Pro Asn Asn Met Pro Gly
945                 950                 955                 960

Ile Trp Asn Lys Asn Trp Gly Tyr Leu Phe Asn Gln Asn Ile Ala Pro
            965                 970                 975

Val Trp Leu Gly Glu Phe Gly Thr Thr Leu Gln Ser Thr Thr Asp Gln
            980                 985                 990

Thr Trp Leu Lys Thr Leu Val Gln Tyr Leu Arg Pro Thr Ala Gln Tyr
        995                 1000                1005

Gly Ala Asp Ser Phe Gln Trp Thr Phe Trp Ser Trp Asn Pro Asp
    1010                1015                1020

Ser Gly Asp Thr Gly Gly Ile Leu Lys Asp Asp Trp Gln Thr Val
    1025                1030                1035

Asp Thr Val Lys Asp Gly Tyr Leu Ala Pro Ile Lys Ser Ser Ile
    1040                1045                1050

Phe Asp Pro Val
    1055
```